United States Patent [19]
Skillicorn et al.

[11] Patent Number: 5,808,306
[45] Date of Patent: Sep. 15, 1998

[54] X-RAY DETECTOR

[75] Inventors: Brian Skillicorn, Saratoga; Giovanni Pastrone, Los Gatos, both of Calif.

[73] Assignee: Cardiac Mariners, Inc., Los Gatos, Calif.

[21] Appl. No.: 703,044

[22] Filed: Aug. 26, 1996

Related U.S. Application Data

[63] Continuation of Ser. No. 387,292, Feb. 10, 1995, Pat. No. 5,550,378, which is a continuation-in-part of Ser. No. 375,501, Jan. 17, 1995, abandoned, which is a continuation of Ser. No. 42,742, Apr. 5, 1993, abandoned.

[51] Int. Cl.⁶ .............................. G01T 1/20; G01T 1/208
[52] U.S. Cl. .......................... 250/367; 250/369; 378/205
[58] Field of Search ..................... 250/366, 367, 250/368, 369, 370.09, 370.11; 378/197, 205

[56] References Cited

U.S. PATENT DOCUMENTS

| | | |
|---|---|---|
| 4,435,830 | 3/1984 | Suzuki et al. .......................... 378/197 |
| 4,802,195 | 1/1989 | Wojcienchowski et al. ....... 378/208 X |

*Primary Examiner*—Edward J. Glick
*Attorney, Agent, or Firm*—Lyon & Lyon LLP

[57] ABSTRACT

The detector of the present invention comprises a plurality of densely packed x-ray detectors arranged into an array. Each detector preferably comprises a scintillator element which is optically coupled to a photodetector element, preferably with a fiber optic link. Each photodetector element is preferably optically separate from adjacent photodetector elements. The detector array preferably includes integral alignment means to align the scintillator elements with the photodetector elements. The scintillator array elements are preferably formed from materials which possess a fast response and a minimum afterglow time.

21 Claims, 44 Drawing Sheets

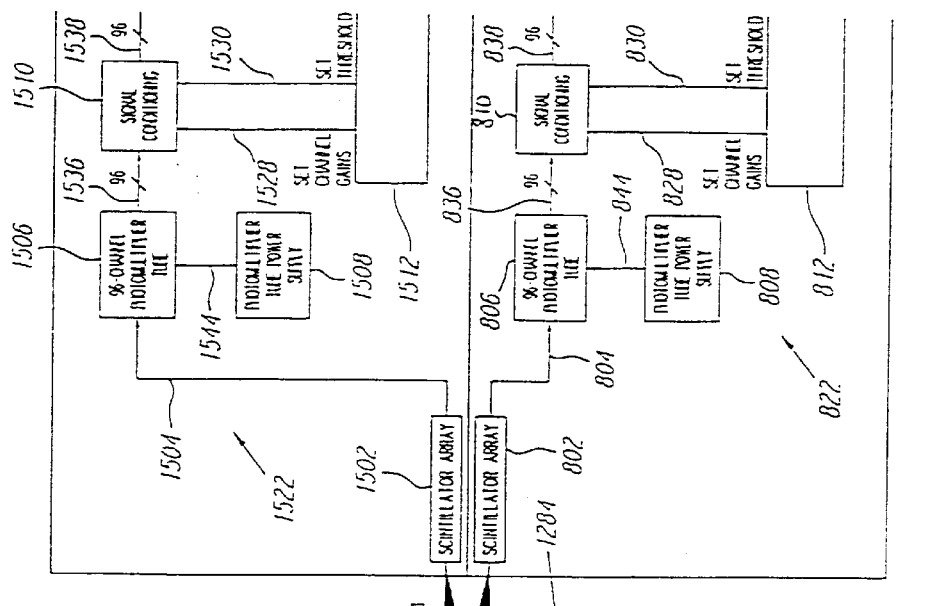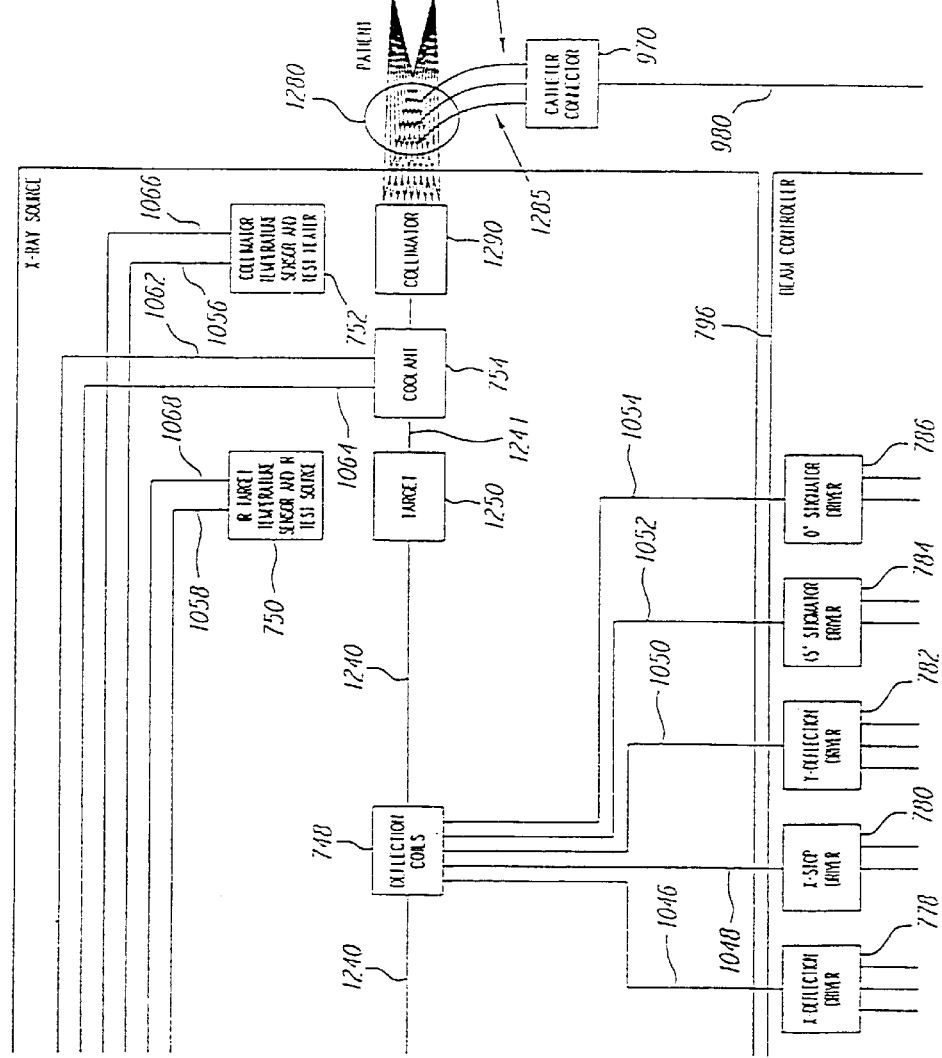
FIG. 15
FIG. 16
FIG. 17
| FIG. 16 | FIG. 17 |

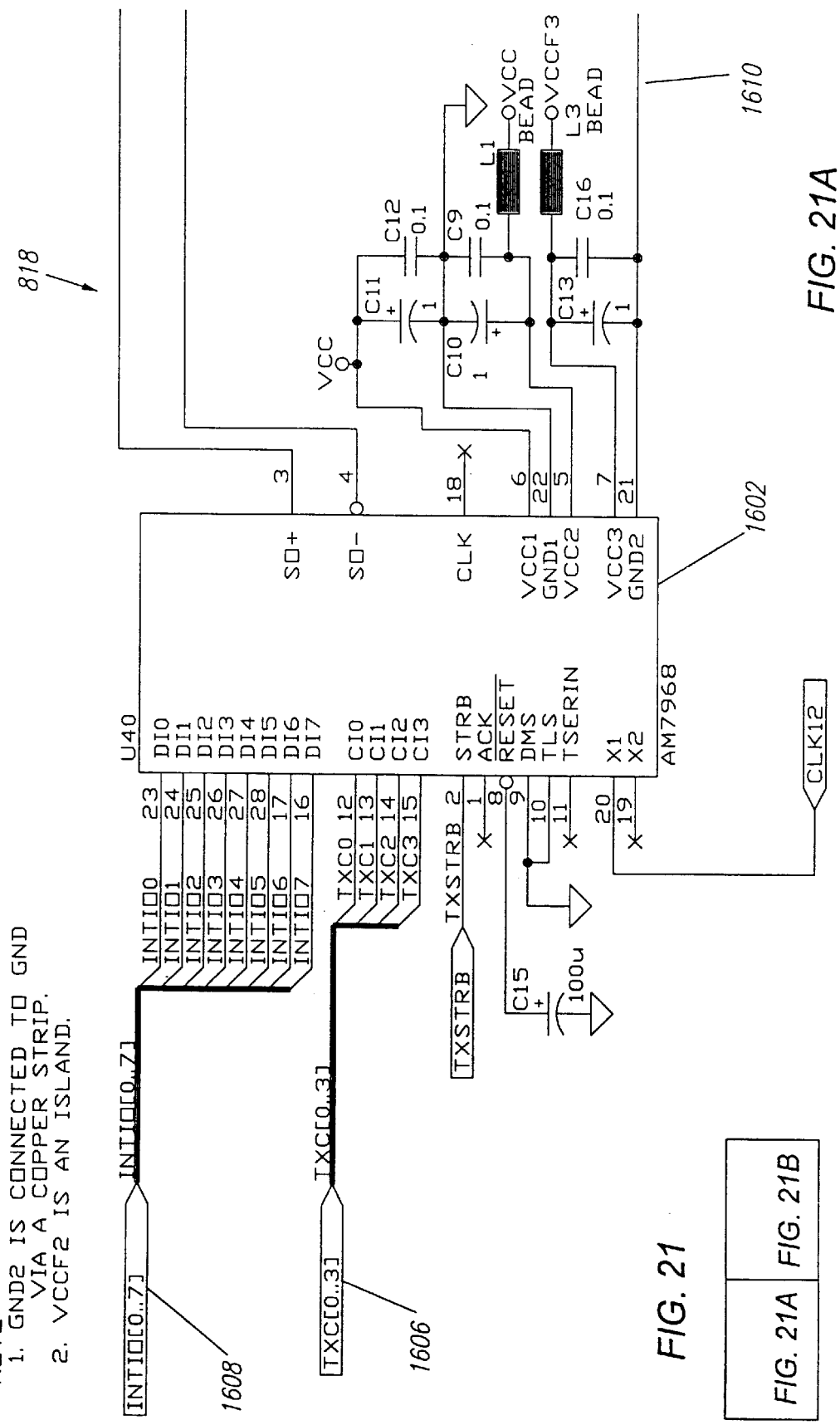

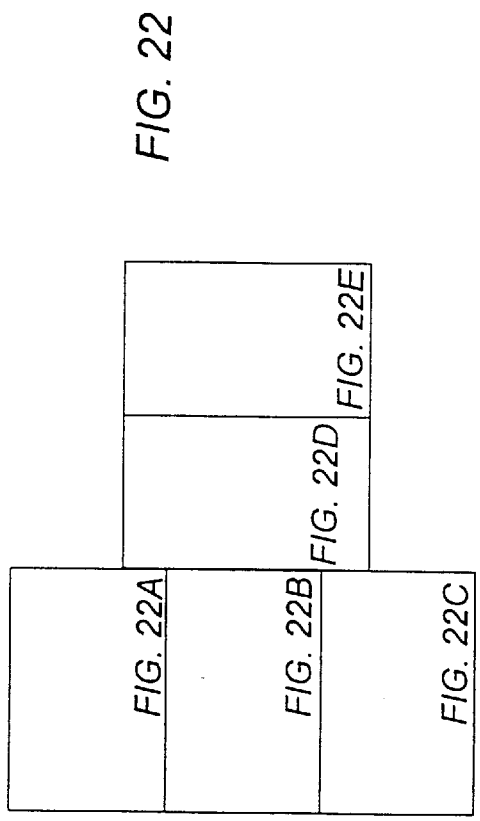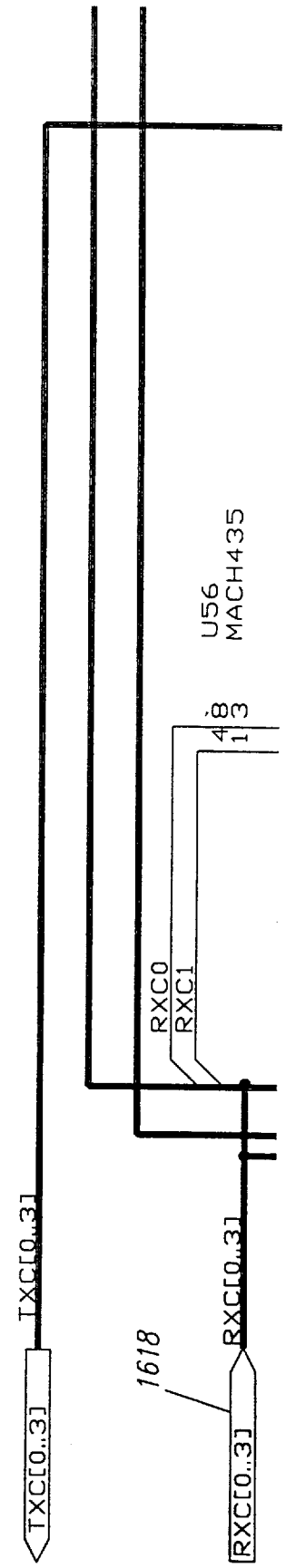

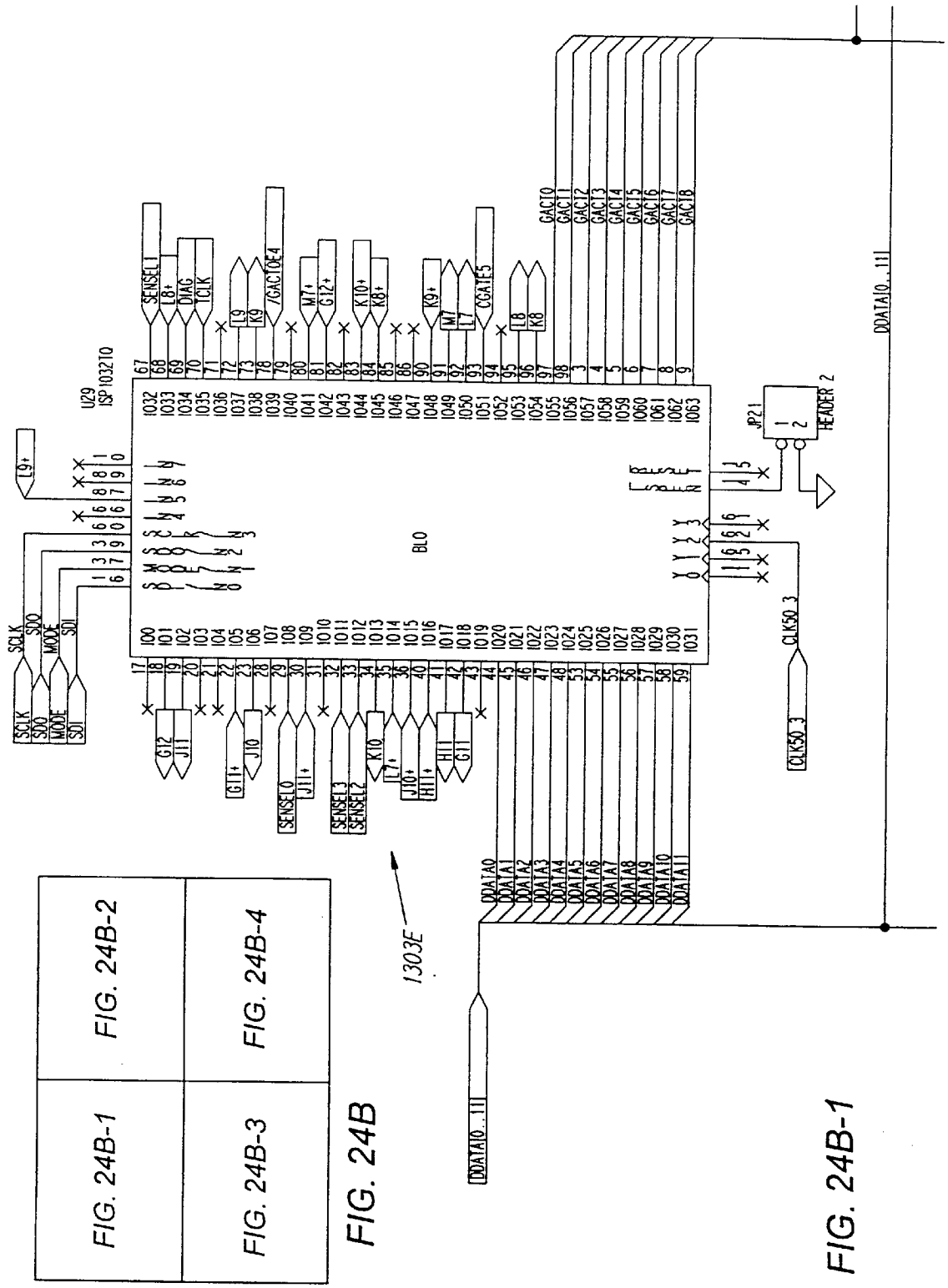

| FIG. 27A | FIG. 27B | FIG. 27C |

| FIG. 27D |

X-RAY DETECTOR

CROSS-REFERENCE TO RELATED APPLICATIONS

This application is a continuation of U.S. patent application Ser. No. 08/387,292, filed Feb. 10, 1995, which issued as U.S. Pat. No. 5,550,378. U.S. patent application Ser. No. 08/387,292 is a continuation-in-part of U.S. patent application Ser. No. 08/375,501, filed Jan. 17, 1995, now abandoned, which is a continuation of U.S. patent application Ser. No. 08/042,742, filed Apr. 5, 1993, now abandoned; and, of International Patent Application Ser. No. PCT/US94/03737, filed Apr. 5, 1994, which designated the United States from which priority is claimed under the provisions of 35 U.S.C. §§ 120 and 365, all of which are incorporated herein by reference in their entirety. The reader is referred to copending U.S. patent application Ser. No. 08/386,884, and copending U.S. patent application Ser. No. 08/386,861, both filed Feb. 10, 1995 concurrently with this application, the disclosures of which are incorporated herein by reference in their entirety.

BACKGROUND OF THE INVENTION

1. Field of the Invention

The present invention pertains generally to the field of radiation imaging. More specifically, the present invention pertains to the field of detectors for scanning beam x-ray imaging systems.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modern medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. An example of a known fluoroscopy system is U.S. Pat. No. 2,730,566 issued to Bartow, et. al. entitled "Method and Apparatus for X-Ray Fluoroscopy."

Reverse-geometry scanning-beam x-ray imaging systems are also known. In such systems, an x-ray tube generates an electron beam which is focussed upon a small spot on the relatively large anode (transmission target) of the tube, inducing x-ray radiation emission from that spot. The electron beam is deflected (electromagnetically or electrostatically) in a scanning pattern over the anode. A small x-ray detector is placed at a distance from the anode of the x-ray tube. The detector typically converts x-rays which strike it into an electrical signal in proportion to the detected x-ray flux. When an object is placed between the x-ray tube and the detector, x-rays are attenuated by the object in proportion to the x-ray density of the object. While the x-ray tube is in the scanning mode, the signal from the detector is inversely proportional to the x-ray density of the object.

The spatial resolution and the signal-to-noise ratio of x-ray images formed by known reverse-geometry scanning x-ray imaging systems are dependent, to a large extent, upon the size of the sensitive area of the detector. If the detector aperture is increased in area, more of the diverging rays are detected, effectively increasing sensitivity and improving the signal-to-noise ratio. At the same time, however, the larger detector aperture reduces attainable spatial resolution as the "pixel" size (measured at the plane of the object to be imaged) becomes larger. This is necessarily so because most objects to be imaged in medical applications (e.g., structures internal to the human body) are some distance from the x-ray source. In the known systems, therefore, the detector aperture size has been selected so as to effect a compromise between resolution and sensitivity, it not being previously possible to maximize both resolution and sensitivity simultaneously.

Examples of known reverse-geometry scanning-beam x-ray systems include those described in U.S. Pat. No. 3,949,229 to Albert; U.S. Pat. No. 4,032,787 to Albert; U.S. Pat. No. 4,057,745 to Albert; U.S. Pat. No. 4,144,457 to Albert; U.S. Pat. No. 4,149,076 to Albert; U.S. Pat. No. 4,196,351 to Albert; U.S. Pat. No. 4,259,582 to Albert; U.S. Pat. No. 4,259,583 to Albert; U.S. Pat. No. 4,288,697 to Albert; U.S. Pat. No. 4,321,473 to Albert; U.S. Pat. No. 4,323,779 to Albert; U.S. Pat. No. 4,465,540 to Albert; U.S. Pat. No. 4,519,092 to Albert; and U.S. Pat. No. 4,730,350 to Albert.

Accordingly there is a need for an x-ray detector which contains a large enough detection area to provide high detection sensitivity while containing sufficiently sized detection elements to maintain increased spatial resolution.

SUMMARY OF THE INVENTION

The detector of the present invention comprises a plurality of densely packed x-ray detectors preferably arranged into an array. Each detector preferably comprises a scintillator element which is optically coupled to a photodetector element, preferably with a fiber optic link. The detector array preferably includes integral alignment means to align the scintillator elements with the photodetector elements. The scintillator array elements are preferably formed from materials which possess a fast response and a minimum afterglow time.

These and many other objects and advantages of the present invention will become apparent to those of ordinary skill in the art from a consideration of the drawings and the description of the invention contained herein. The principles of the present invention may be employed in any application, medical or industrial.

BRIEF DESCRIPTION OF THE DRAWINGS

FIG. 15 is a layout arrangement plan for FIGS. 16–17.

FIG. 16–17 are a partial functional block diagram comprising a preferred dual multi-detector array for a scanning-beam imaging system.

FIG. 20 and 21 are a layout arrangement plan for FIGS. 20A–E and 21A–B respectively.

FIGS. 20A–E and 21A–B comprise schematics of the preferred real time eye optical to electrical and electrical to optical conversion circuitry.

FIG. 22 is a layout arrangement plan for FIGS. 22A–E.

FIGS. 22A–E are schematics of the controller for the image reconstruction engine and gain & alignment circuitry.

FIGS. 23A–B are diagrams showing the preferred input sensor connectors between the photomultiplier tube and the signal conditioning circuits in the Real-time eye.

FIGS. 24A-1 to 4 and 24B-1 to 4 comprise schematics of the preferred octant counters.

DESCRIPTION OF THE PREFERRED EMBODIMENTS

Figure 1:
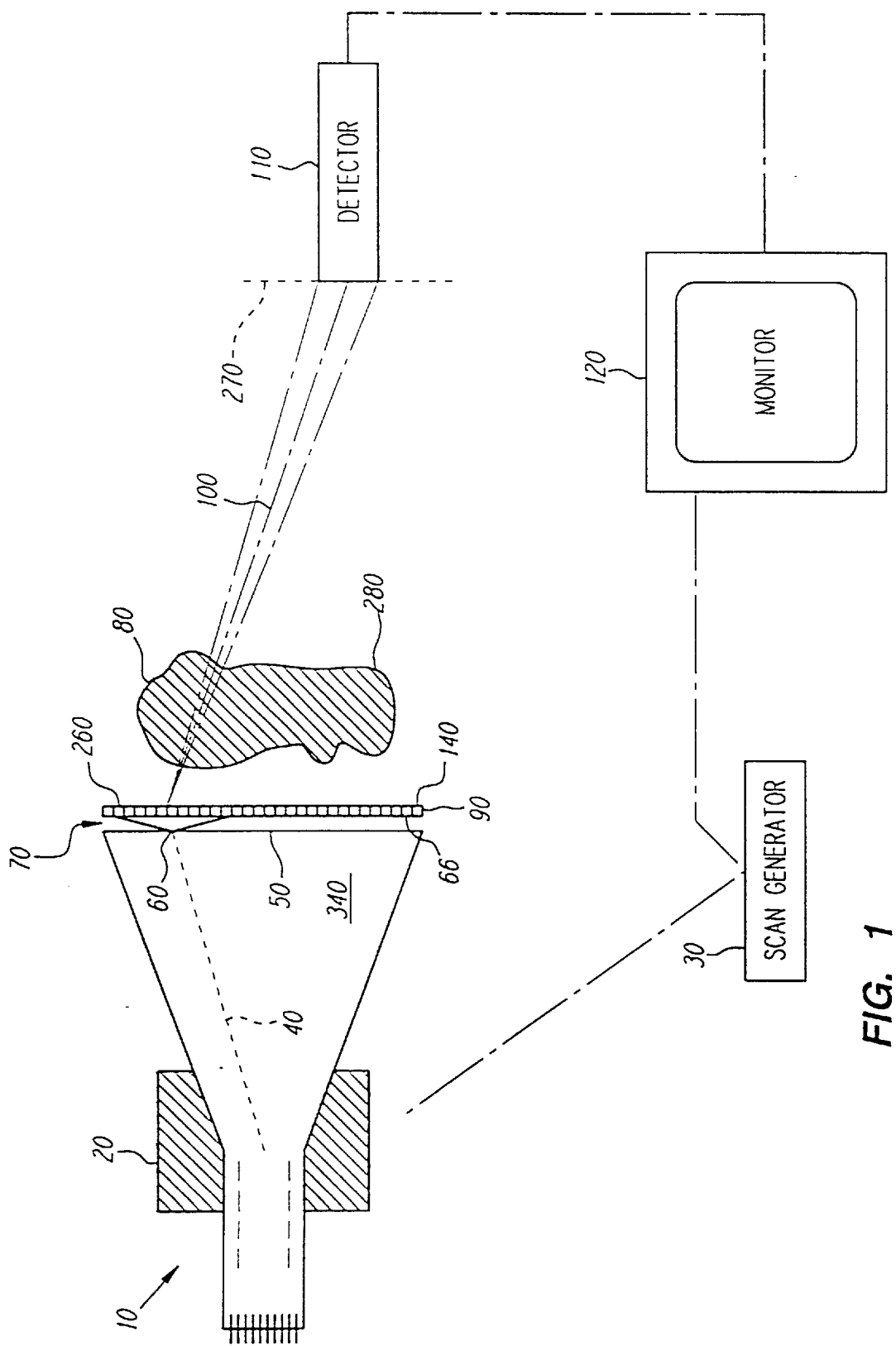
FIG. 1 is a diagram showing the basic components of a preferred scanning-beam x-ray imaging system.

Turning to FIG. 1, an embodiment of a presently preferred multi-detector array 110 employed in a reverse geometry scanning-beam x-ray imaging system is diagrammed. The preferred x-ray source 10, preferably a scanning beam x-ray tube, is more fully described in copending patent application Ser. No. 08/386,864, which has been incorporated herein by reference in its entirety. An electron beam 40 generated within x-ray source 10 is scanned across a grounded anode target 50 within x-ray source 10 in a predetermined pattern. For example, the predetermined pattern may be a raster scan pattern, a serpentine (or "S" shaped) pattern, a spiral pattern, a random pattern, a gaussian distribution pattern centered on a predetermined point of the anode target, or such other pattern as may be useful to the task at hand.

As electron beam 40 strikes anode target 50 at point 60, a cascade of x-rays 70 is emitted and travel outside of x-ray source 10 toward the object 80 to be investigated. To optimize system performance of the presently preferred embodiment, a cone of x-ray photons should be generated that will diverge in a manner that will just cover the multi-detector array 110.

This is preferably accomplished by placing a collimation grid 90 between the anode target 50 of the scanning x-ray source 10 and the multi-detector array 110, and more preferably between the anode target 50 and the object 80 to be imaged. Collimation grid 90, containing a grid of x-ray transmissive apertures 140, is designed to permit passage of only those x-ray pencil beams 100 whose axes lie in a path that directly intercepts multi-detector array 110. Thus, as electron beam 40 is scanned across anode target 50, at any given moment there is only a single x-ray pencil beam 100 which passes through object 80 to multi-detector array 110. The preferred collimation grid is described more fully in copending U.S. patent application Ser. No. 08/386,861, which has been incorporated herein by reference in its entirety.

The output of multi-detector array 110 is processed and displayed on monitor 120 as luminance values. Image processing techniques can be used to produce a computer driven image on an appropriate display or photographic or other medium. The preferred image processing techniques are described more fully in copending patent application Ser. No. 08/386,861, which has been incorporated herein by reference in its entirety.

To achieve resolutions of several line pairs per millimeter or more at the object plane, as are required in some medical applications, the spatial resolution limit in known x-ray imaging systems, particularly reverse-geometry systems, is in large part determined by the size of the single non-segmented detector. Generally speaking, a small non-segmented detector can provide high spatial resolution while a large non-segmented detector provides high collection efficiency. It has in part been this trade off that has been a problem in developing low dosage x-ray imaging systems.

By fabricating a multi-detector array 110 having a large area subdivided into multiple smaller detector array elements, a large capture area is achieved, and when using the image reconstruction methods described in copending U.S. patent application Ser. No. 08/386,861, which has been incorporated herein by reference in its entirety, simultaneously retaining an image resolution that is comparable to the size of a single small detector element without increasing x-ray intensity an/or exposure time.

The preferred detector element employs a scintillator to convert x-ray photon energy to light energy. The light energy is then detected and converted to an electrical signal by means of a photomultiplier, photo diode, CCD or similar device.

The scintillator used to detect the x-ray photons preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

In the preferred x-ray imaging system in which the multi-detector 110 is used, which is described more fully in copending U.S. patent application Ser. No. 08/386,861, which has been incorporated herein by reference in its entirety, image information must be obtained in a very short time period, therefore the preferred detector element comprises a scintillator which has a fast response and a minimum afterglow time. Afterglow is the phenomenon wherein the scintillator continues to emit light after the stimulating incident x-rays have ceased.

Plastic scintillators, such as organic loaded polystyrene, are suitable from a standpoint of speed in that they have the required fast response and minimum afterglow characteristics. However, plastic scintillators have a relatively small x-ray photon interaction cross section so that their linear x-ray absorption coefficients are also small in value. The consequence is that a considerable thickness is required to absorb x-ray photons. For 100 keV x-rays, a typical plastic scintillator should be about 28 cm (11 in) thick to capture 99% of the incident x-rays.

The preferred scintillator materials are: (1) YSO (cerium doped yttrium oxyorthosilicate) (2) LSO (cerium doped lutetium oxyorthosilicate) and (3) BGO (bismuth germanate). All three are available from Airtron (Litton Industries) of Charlotte, North Carolina. YSO and LSO are the preferred materials with YSO more preferred on the basis of cost. LSO has a higher stopping power for x-rays so it is the first preference for use with higher voltage x-ray sources, since a length shorter than that of YSO can be employed to stop x-rays of similar energies. BGO must be heated to about 100°C. in order to achieve the required light output decay period of about 50 nanoseconds. These scintillators typically provide high quantum efficiencies. For 100 keV x-rays, the preferred length for YSO is 0.5 cm.

According to a presently preferred embodiment, the scintillators are coated on 5 sides with aluminum which is preferably applied by evaporation in vacuo. The uncoated side is that from which the scintillation light emerges to a light detector. In an alternative embodiment, the scintillators are coated on 5 sides with titanium dioxide paint. In both these embodiments, the coatings reflect the scintillation light internally within the scintillator crystal so that it is prevented from escaping except from the uncoated side thus providing a high light transfer efficiency to the light detector means which is optically coupled to the uncoated side.

Figure 2:
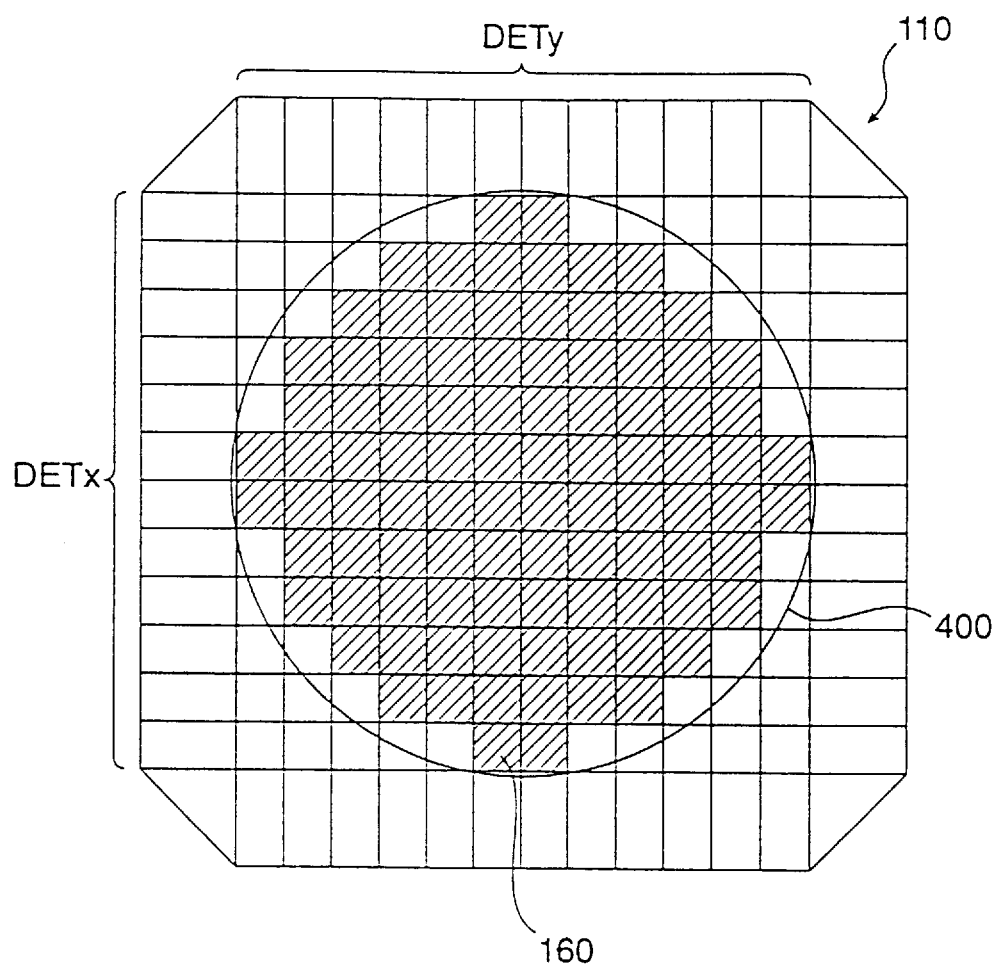
FIG. 2 is a diagram of the preferred arrangement of 96 scintillator elements to form a pseudo-circular array.

According to one embodiment of the present invention, multi-detector array 110 comprises at its input face a pseudo-round array of 96 densely packed scintillators including two rows of 12 and two columns of 12 at its horizontal and vertical midplanes (FIG. 2). A square 5-by-5 and a square 3-by-3 array are also contemplated as is a non-square array of scintillators filling a circle about the center of the multi-detector array.

Figure 3:
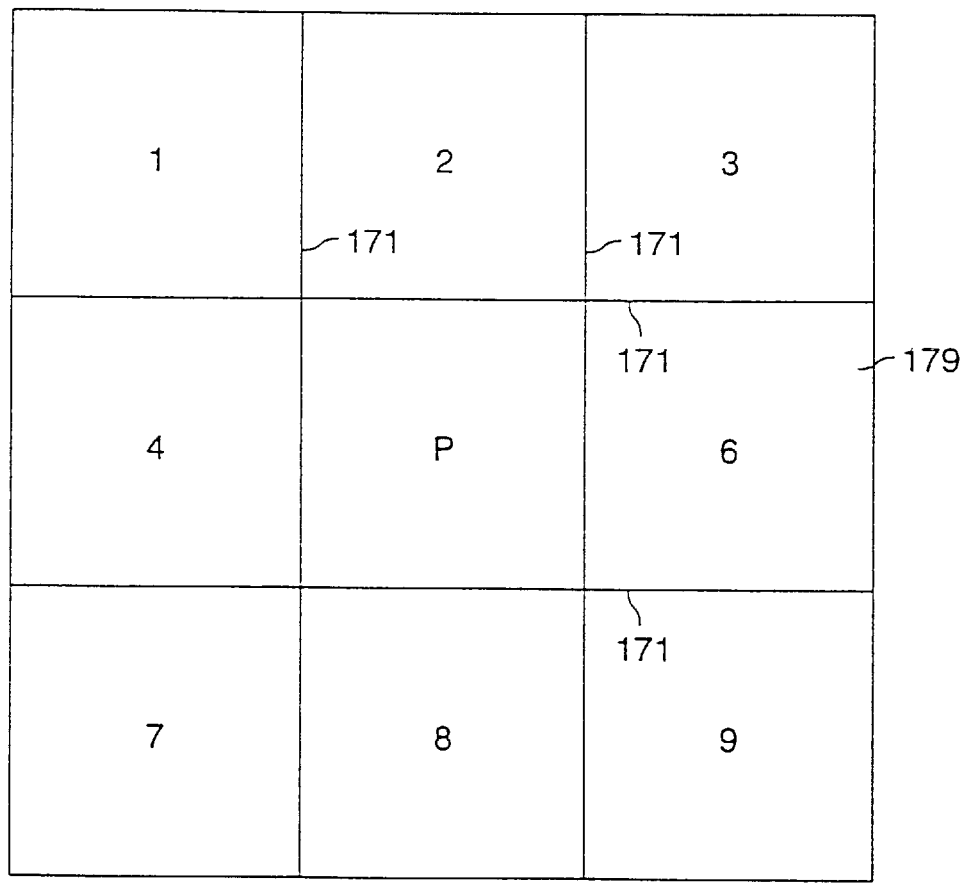
FIG. 3 is a diagram of a 3×3 multi-detector array.

X-ray photons striking any one scintillator 170 should contribute to the final x-ray image with the spatial position reference that corresponds to the position of that one scintillator only. Light or x-rays striking a scintillator which couples into adjacent scintillators may cause a degradation of image quality. Such cross-talk between scintillators can be caused by some or all of the following mechanisms: direct light transmission, scattered incident x-rays, x-rays entering near to the scintillator edge which have an angle of incidence greater than zero and fluorescent x-rays generated within the scintillator material. This problem is preferably addressed by placing septa 171 between neighboring scintillators which are made out of a material which is opaque to light and which greatly attenuates x-rays. An example of a preferred positioning of septa 171 is shown in FIG. 3. While the x-ray collection efficiency may be reduced by the finite thickness of septa 171, which will intercept some x-ray photons, the quality of the final x-ray image is not affected to any substantial degree. Preferred materials for septa 171 are those with a high atomic number such as gold, platinum, tantalum, tungsten or lead. In the preferred embodiment described in detail later, the septum material is tungsten loaded epoxy. The thickness of septa 171 is preferably in the range 0.005 cm (0.002") to 0.013 cm (0.005"). The choice of thickness and material for septa 171 is dependant to some degree on the choice of scintillator material. The predominant fluorescent x-rays from YSO are emitted with an energy of about 15keV and will be adequately stopped by septa at the low end of the quoted thickness range whereas the predominant x-rays from LSO have an energy of about 54 keV and a greater septum thickness will be required.

Figure 4:
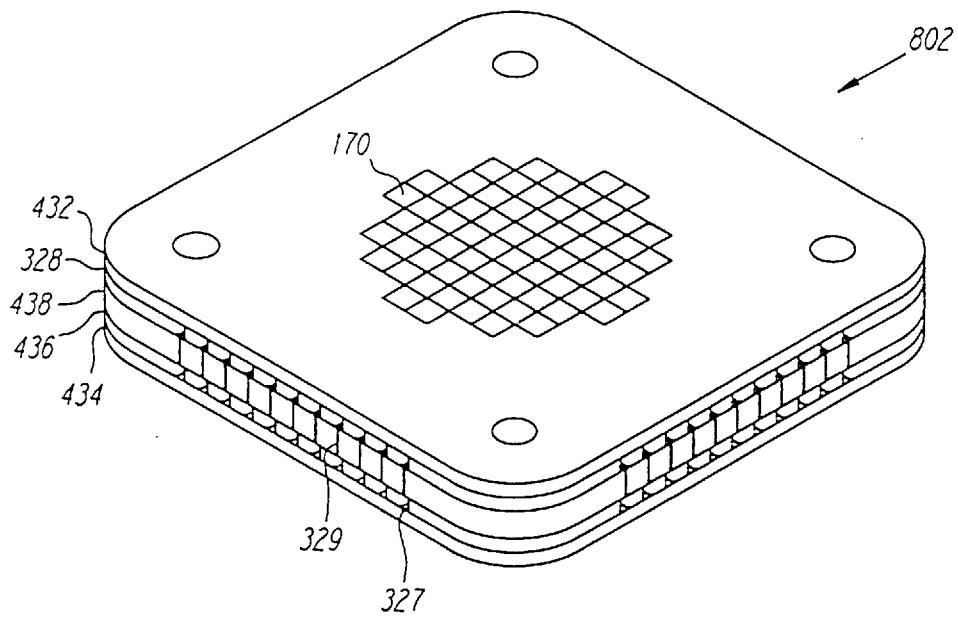
FIG. 4 is an orthogonal view of a preferred scintillator assembly.
Figure 5:
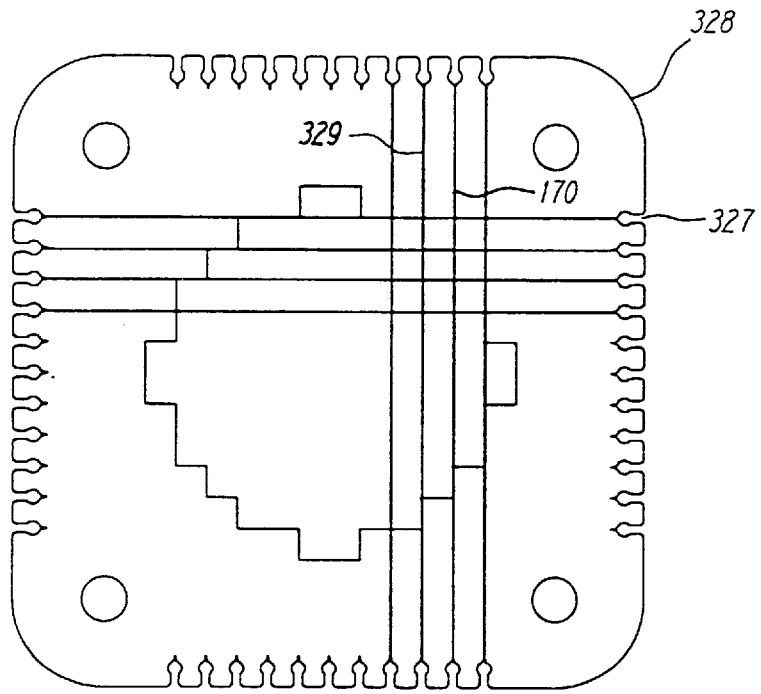
FIG. 5 diagrams a preferred wireframe for the scintillator assembly of FIG. 4.

FIG. 4 is a representation of the preferred scintillator assembly 802 comprising a scintillator array 112, end-plates 432 and 434, wireframes 328 and 436, and spacer 438. Wireframe 328, best shown in FIG. 5, is preferably a sheet of stainless steel which measure approximately 1.125 inches on each side. A pseudo-circular pattern with a diameter of approximately 0.719 inches is cut in the center of wireframe 328. Eleven notches 327, approximately 0.06 inches in depth, are evenly spaced along the center 0.60 in. section on each edge of wireframe 328. Wireframe 436 is identical to top wireframe 328.

To construct the scintillator assembly 802, a spacer 438 is disposed between wireframes 328 and 436. Spacer 438 is preferably a flat piece of metal with a circular opening in its center corresponding to the circle defined by the scintillator array 112. Wires 329 are stretched from a notch 327 on one edge of wireframe 328 to the notch on its directly opposite edge, and then are wrapped around the spacer 438 to the corresponding notches on wireframe 436. When a wire 329 has been stretched through every notch 327 on both wireframes, 96 square sections will be created in the pseudo-circular hole that was formed in wireframes 328 and 436.

An x-ray sensitive scintillator element 170 is placed into each of these square sections within the wireframe arrangement to form the scintillator array 112. The scintillator elements 170 are preferably cut to a square horizontal cross-section. The length of the individual scintillator elements 170 are preferably about 0.5 cm and the exterior faces are preferably 0.135 cm×0.135 cm. The scintillator elements 170 are preferably YSO, but other materials may also be used as discussed above. The stretched wires 329 help to align the placement of the scintillator elements 170. A composition of tungsten loaded epoxy is preferably used to fill the space between and around the scintillator elements 170 and to fill the gaps created by the wires 329 when stretched across the wireframes 328 and 436.

In another embodiment, a frame equal in depth to the scintillator length and preferably 1.25" square incorporates integral septa to form preferably 96 square section holes into which the scintillators are inserted and held in place by means of preferably epoxy adhesive. The frame is preferably made by the electrical discharge machining process. In another embodiment the aforementioned frame is built up out of thin lamina which incorporate preferably 96 square section holes. Each lamination would be preferably 0.05 cm thick and would be made by a chemical etching process. In yet another embodiment, the aforementioned frame is machined with a pseudo-circular hole and with two 90° sets of milled slots in its edges, each slot preferably slightly wider than the septum material thickness and spaced apart by a distance equal to the scintillator spacing. Strips of septum material preferably equal in width to the scintillator length and preferably 1.00" long are inserted into the milled slots to form the septa. Each strip of septum material preferably has slots, slightly wider than the material thickness, which are spaced apart by a distance equal to the scintillator spacing and which extend half way across the strip width. The x-axis strips consequently mesh with the y-axis strips in the manner of an egg crate to form 96 square section holes into which the scintillators are inserted and secured by preferably epoxy adhesive.

In the preferred embodiment the output face of the scintillator assembly 802 is lapped to produce a flat polished surface after insertion of scintillators elements 170.

Figure 6:
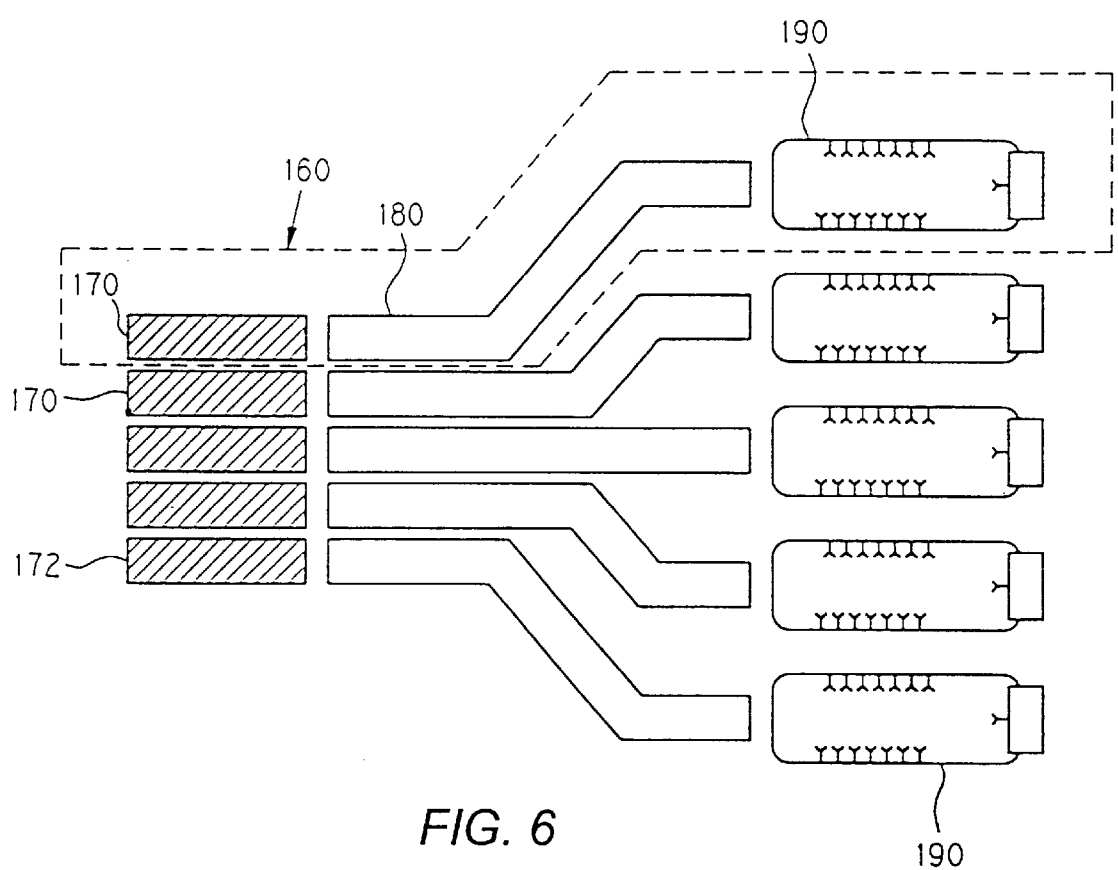
FIG. 6 is a functional representation of one row or column of detector elements for a 5×5 multi-detector array.

According to one presently preferred embodiment of the detector element 160 (FIG. 6), each scintillator element 170 is preferably in contact with a light pipe or fiber optic link 180 which optically couples each scintillator element 170 with a corresponding photomultiplier tube channel 190 or solid state detector. A suitable coupling medium is preferably applied between each end of the fiber optic link 180 to ensure low transmission losses at the interfaces.

Figure 7:
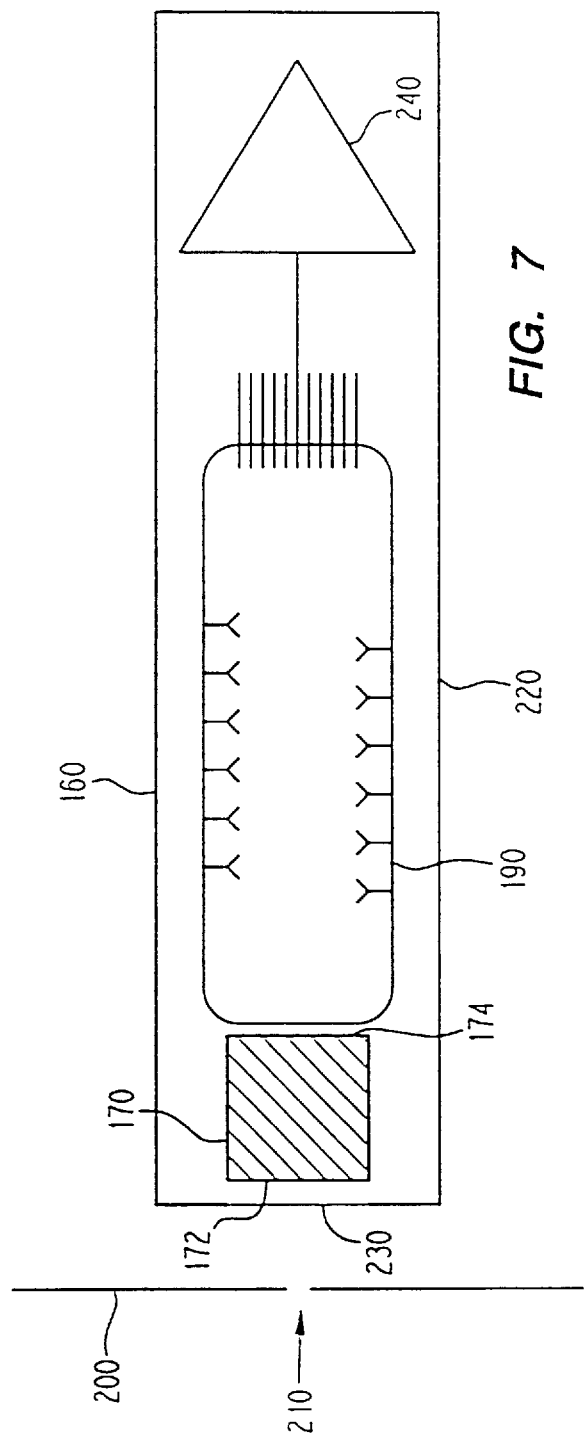
FIG. 7 depicts one embodiment of a detector element.

Alternatively, scintillators 170 may be located in close physical proximity to their corresponding photodetectors, as shown in FIG. 7, eliminating the need for a fiber optic link. In the embodiment shown in FIG. 7, an x-ray opaque sheet 200 with apertures 210 corresponding to each detector element 160 is disposed in front of multi-detector array 110. Each detector element 160 is enclosed in a light tight enclosure 220 which may also be x-ray opaque. A light blocking window 230, preferably made of a thin aluminum sheet, is located at the front of light tight enclosure 220. Light blocking window 230 is x-ray transmissive. Within light tight enclosure 220 is a scintillator element 170 in close proximity to a photomultiplier tube 190 which is preferably electrically connected to a pre-amplifier 240.

Alternatively the scintillator array can be placed in direct or close contact with an array of photo diodes, avalanche photo diodes, vacuum avalanche photo diodes, photo transistors or charge coupled devices to achieve a rugged and compact detector. Where solid state devices, particularly CCDs, are used, cooling, such as with a Peltier-type cooler, or the like, may be employed to increase the signal-to-noise ratio of the device. Alternatively the scintillator array could be coupled optically or be in direct or close contact with one or more position sensitive optical detectors, preferably a multi-channel photomultiplier tube or a segmented anode microchannel plate image intensifier, which provide an output signal which identifies the position coordinates of the light source as well as its amplitude.

Figure 8:
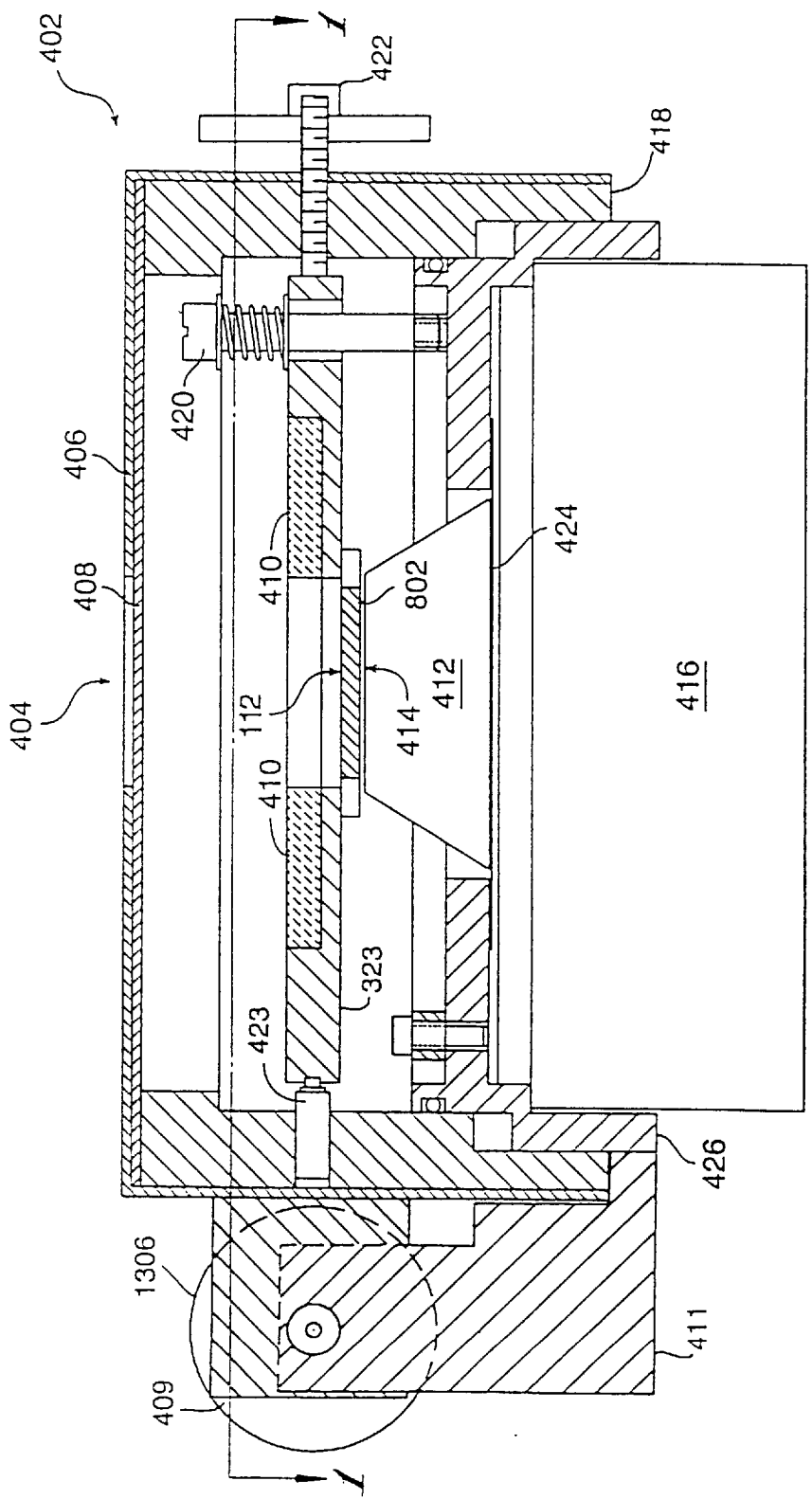
FIG. 8 is a partial cross-sectional representation of one embodiment of a multi-detector array assembly.

Referring to FIG. 8, one embodiment of a multi-detector array assembly 402 comprises a scintillator assembly 802, a multi-channel photomultiplier tube 416, a fiber optic link 412, integral alignment means, and an outer detector housing 418. Multi-detector array assembly 402 preferably contains a light tight outer detector housing 418 to minimize any noise which may be generated by stray light. X-rays enter the multi-detector array assembly 402 through an x-ray window 404 in lead shield 406. X-ray window 404 is preferably circular and about 1.91 cm (0.75 in) in diameter to permit a directed beam of x-rays to strike the scintillator array 112 while attenuating scattered x-rays. A light shield 408 is preferably employed to shield the assembly from ambient light. The light shield 408 may be made of a thin sheet of aluminum or beryllium chosen to attenuate light without substantially attenuating the x-rays, and is preferably 0.0125 cm thick.

Figure 9:
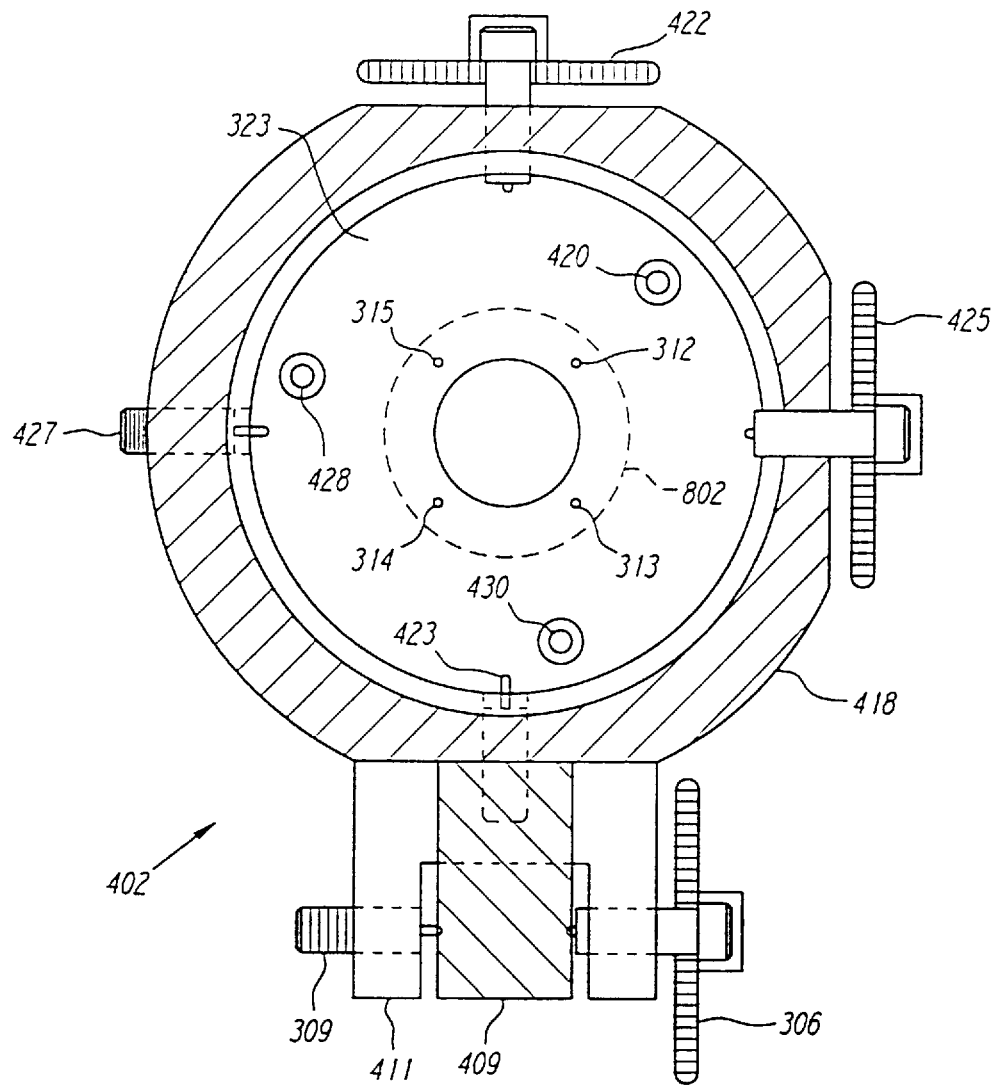
FIG. 9 is a top view representation taken along plane 1—1 of the multi-detector array assembly of FIG. 8.

Scintillator assembly 802 is preferably positioned such that the pseudo-circular scintillator array 112 is substantially aligned with the x-ray window 404. As shown in FIG. 9, scintillator assembly 802, which is outlined in phantom, is preferably attached to adjuster plate 323 with attachment screws 312, 313, 314 and 315. If BGO scintillators are employed, then a heating element 410, preferably a resistive heating element designed to keep the scintillator assembly 820 at an operating temperature of about 100° C., is positioned on the adjuster plate 323. The preferred scintillator assembly 802 is described more fully in connection with the detailed description of FIGS. 4 and 5.

An optical link, preferably a fiber optic imaging taper 412, directs light photons emerging out of the bottom 414 of the scintillator assembly 802 to a multi-channel photomultiplier tube (PMT) 416. The preferred fiber optic imaging taper 412 is available from Collimated Holes of Campbell, Calif., and has a circular input aperture diameter of approximately 2.03 cm (0.8 in) and a circular output aperture diameter of approximately 3.38 cm (1.33 in). Fiber optic imaging taper 412 matches each scintillator crystal pitch dimension (0.06") to that of the PMT 416(0.10"), i.e., it has a magnification of 1.667 times. High viscosity optical coupling fluid available from Dow Corning (Type 200) with a refractive index approximately matching that of the glass may be used at the two faces of the taper as an optical coupling medium to maximize the light transfer efficiency from the scintillator crystals 170 to the fiber optic imaging taper 412 and from the fiber optic imaging taper 412 to the PMT input face 424.

Figure 10:
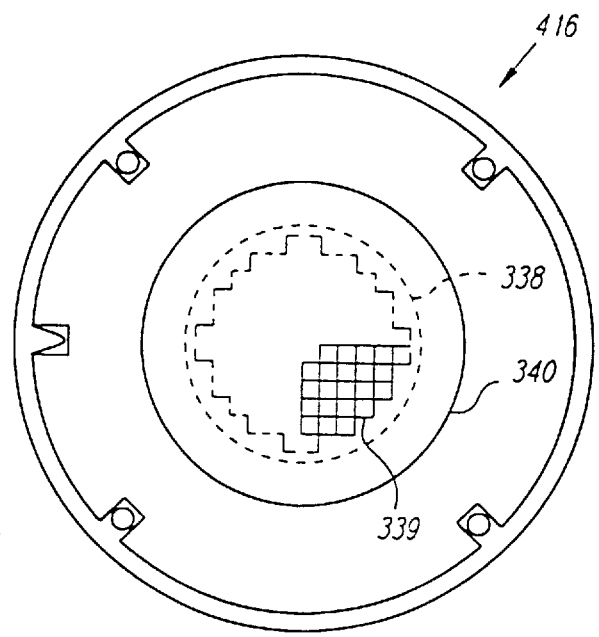
FIG. 10 is a top view of a preferred 96-channel photomultiplier tube.
Figure 11:
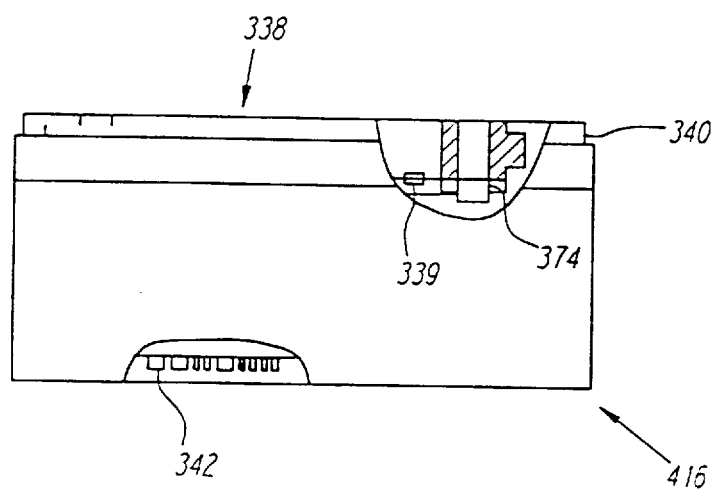
FIG. 11 is a partial cross-sectional side view of the photomultiplier tube of FIG. 10.

The preferred PMT 416 is a 96-channel tube (one channel corresponding to each scintillator crystal 170) model number XP 1724A available from the Philips Corporation. As shown in FIGS. 10 and 11, it preferably has a fiber optic face plate 340 so that the spatial arrangement of the scintillator array 112 is accurately carried through to the PMT photocathode located in the PMT on the other face of the faceplate. 96 photocathode elements 339 are arranged in a pseudo-circular array in the center of the front face of PMT 416. Each photocathode element is preferably square in shape with dimensions of 2.54 mm×2.54 mm. An x-ray photon striking one of the scintillators 170 produces many light photons, some of which are coupled to the PMT photocathode. This produces a corresponding electron pulse at the photocathode and the pulse is amplified in one channel of the PMT dynode structure up to approximately 1,000,000 times.

The pseudo-circular array of 96 photocathode elements creates a light-sensitive circular area 338 on the PMT 416 with a diameter of 30.5 mm. It is this light sensitive area 338 that interfaces with the tapered fiber optic bundle 412. Each PMT photocathode element 339 has a corresponding electrical output connector 342. When light photons reach the PMT 416, the photocathode elements 339 generates signals which are amplified by the dynode structure and output at PMT connectors 342.

Referring again to FIG. 9, three positioning screws 306, 422, and 425 are provided for linear and rotational alignment of the scintillator assembly 802 relative to the PMT 416. Adjuster plate 323 is attached to PMT mount 426 with three shoulder screws 420, 428, and 430 through alignment holes with diameters larger than the diameter of the shoulder screws. Shoulder screws 420, 428, and 430 are spring loaded (shown in FIG. 8) so that adjuster plate 323 is fixed because of the tension applied by the shoulder screw springs, but can be further manipulated for positioning purposes.

Attached to the side of detector housing 418 is y-axis positioning screw 422. Spring loaded return pin 423 is located on the side of detector housing 418 directly opposite y-axis positioning screw 422 and biasing the adjuster plate against the y-axis positioning screw 422. Rotation of y-axis positioning screw 422 will move the adjuster plate 323 along the y-axis, causing a corresponding shift in the y-axis position of the attached scintillator array 112. Similarly, x-axis positioning screw 425 and spring loaded return pin 427 operate in an identical manner to adjust the x-axis positioning of the scintillator array 112.

To adjust the rotational positioning of the scintillator array 112, a tongue 409 of outer detector housing 418 is positioned between rotational positioning screw 306 and spring loaded return pin 309. The tongue 409 is placed between the ends of rotational bracket 411, and is biased by the tension of the loaded return pin 309 against rotational positioning screw 306. Adjusting the rotational positioning screw 306 will cause a rotational shift in the tongue 409 of the outer detector housing 418, causing a corresponding shift in the attached adjuster plate 323, which results in an adjustment of the scintillator array 112 with respect to the PMT 416.

Figure 12:
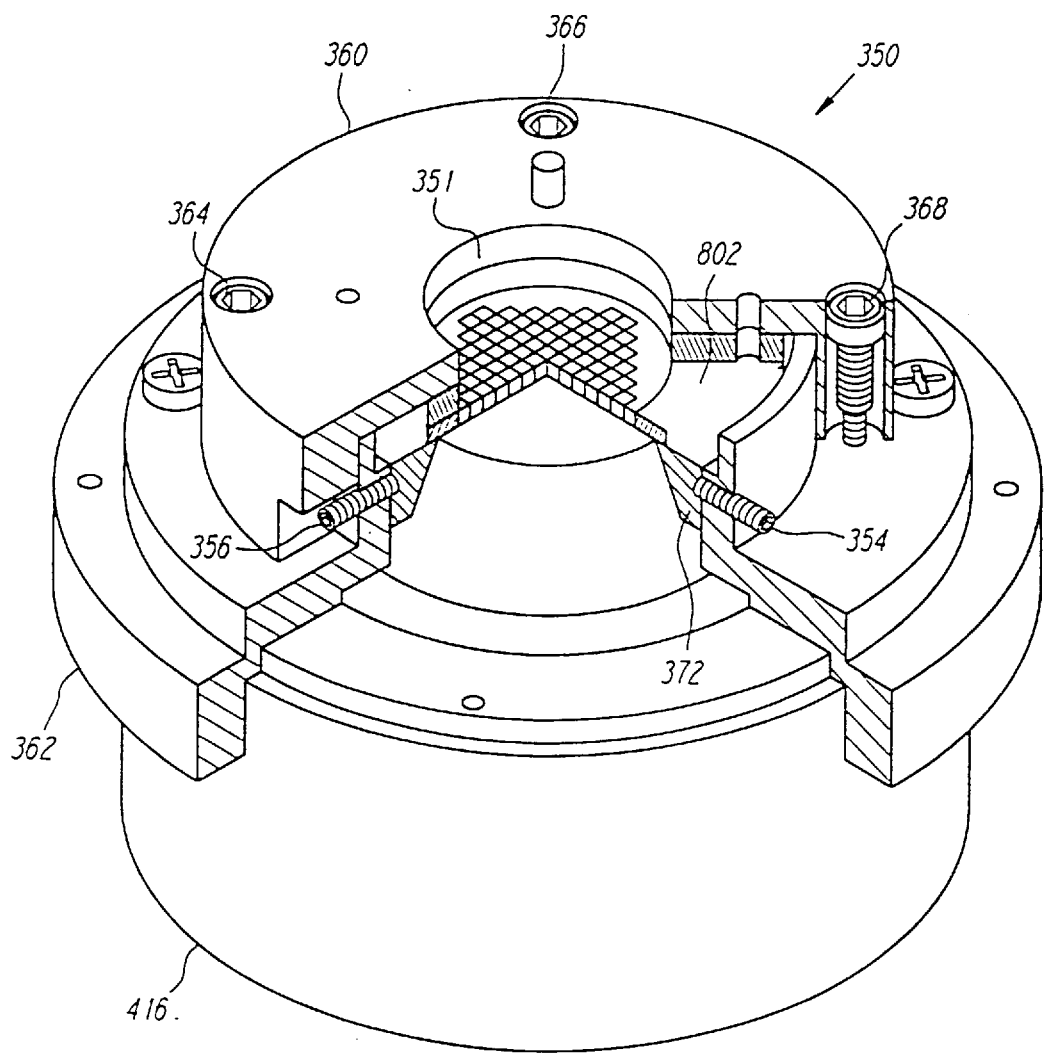
FIG. 12 is a partial cross-sectional perspective view of another embodiment of a multi-detector array assembly.
Figure 13:
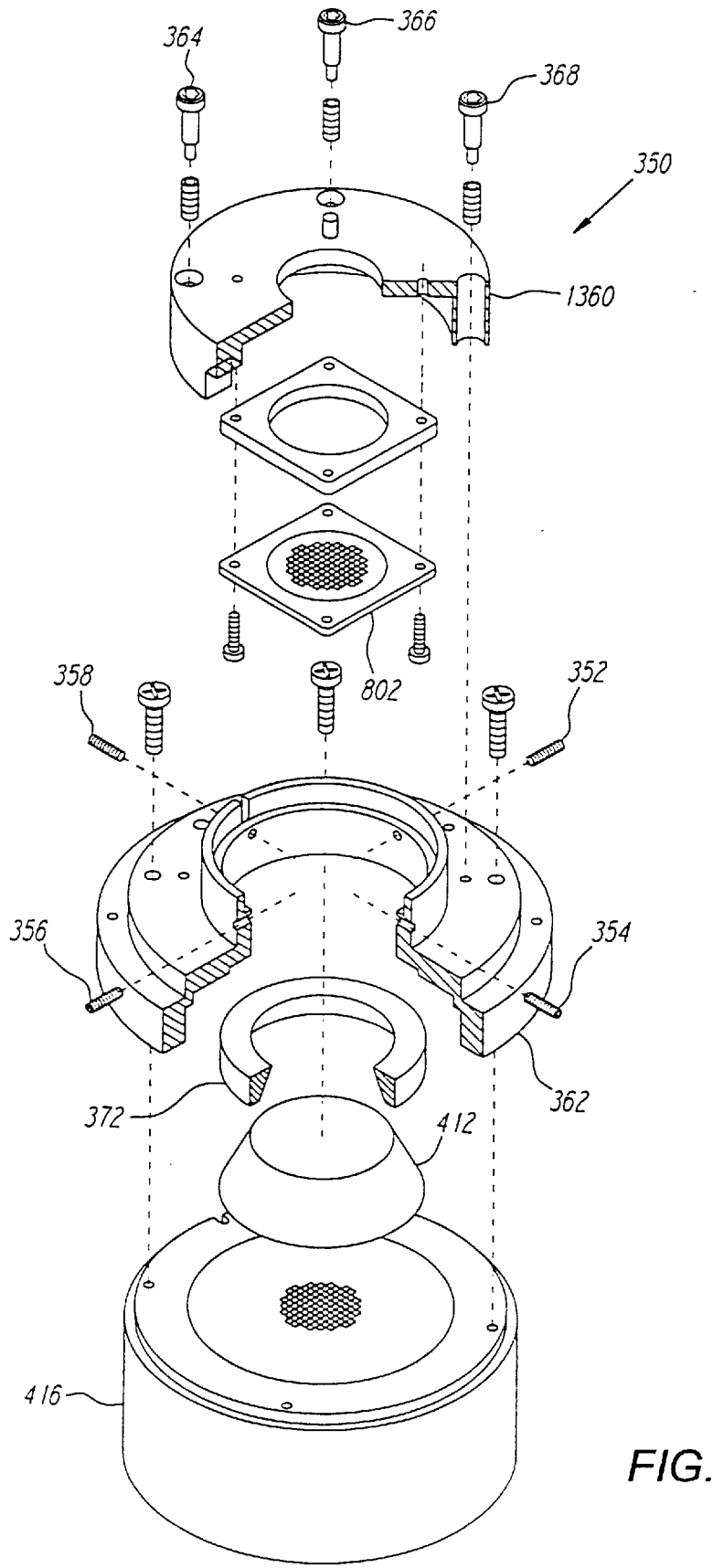
FIG. 13 is an exploded view of the multi-detector array assembly of FIG. 12.

Another embodiment of a multi-detector array assembly 350 depicted with alternate alignment means is shown in FIGS. 12 and 13. X-rays enter through a circular x-ray window 351, preferably 1.91 cm in diameter, which is located in an x-ray opaque detector housing 360. A light shield (not shown) can be disposed adjacent the x-ray window to shield the assembly from ambient light. A scintillator assembly 802, preferably the scintillator assembly described more fully in connection with the detailed description of FIGS. 4 and 5, is rigidly bolted to the interior surface of the detector housing 360. Detector housing 360, with the scintillator assembly 802 rigidly attached, is attached to the PMT mount 362 with four shoulder screws 364, 366, 368, and 370 (370 not shown) through alignment holes with diameters larger than the diameter of the shoulder screws. Shoulder screws 364, 366, 368, and 370 are spring loaded so that detector housing 360 moves axially, because of the tension applied by the shoulder screw springs, to maintain the scintillator assembly 802 in contact with fiber optic imaging taper 412 and to maintain the fiber optic imaging taper 412 in contact with the input face of the PMT 416.

Adjustment collar 372, preferably formed with a cylindrical outer surface and a tapered inner surface, is positioned within the upper aperture of PMT mount 362. Fiber optic imaging taper 412, preferably inserted along the inner tapered surface of the adjustment collar 320, is mounted between the scintillator array 112 and the input face of the PMT 416. The preferred fiber optic imaging taper 412 was described more fully in connection with the detailed description of FIG. 8. PMT 416, preferably the photomultiplier tube described more fully in connection with the detailed description of FIGS. 10 and 11, is rigidly bolted into the lower stepped opening of PMT mount 312.

Four alignment screws 352, 354, 356, and 358 are preferably employed to align the fiber optic imaging taper 412 within the multi-detector array assembly 350. The alignment screws are disposed within four apertures equidistantly placed through the upper walls of the PMT mount 362. The alignment screws are positioned such that they form solid contact with the adjustment collar 372, which is yoked around the fiber optic imaging taper 412. A viscous silicon optical-coupling medium is applied along the two faces of the fiber optic imaging taper 412. To effect the alignment of the fiber optic imaging taper 412, alignment screws 352, 354, 356, and 358 are manipulated such that pressure is applied to the alignment collar 372 in the required alignment direction. This repositions the alignment collar 372, forming a corresponding repositioning of the fiber optic imaging taper 412.

Figure 14:
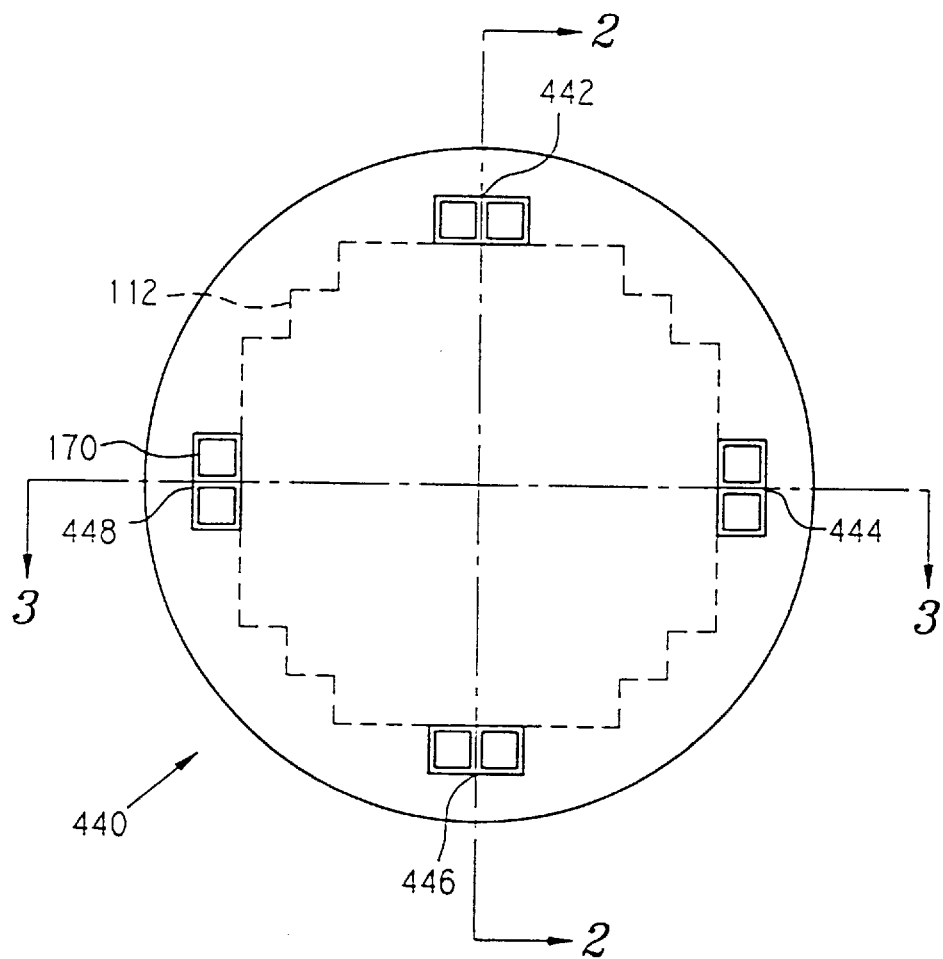
FIG. 14 is a top view of a preferred x-ray alignment shield.

According to one method to optimally align the scintillator elements 170 in relation to their corresponding photomultiplier tube elements 339, an x-ray shield 440, formed of an x-ray opaque material and containing x-ray transmissive windows, is disposed before the input face of the scintillator array 112. As shown in FIG. 14, the preferred x-ray shield 440 is a circular disc formed of lead with four equally sized x-ray transmissive windows (442, 444, 446, and 448), equidistantly spaced along the outer perimeter, such that each x-ray transmissive window corresponds to an equivalent number and placement of scintillator elements 170 along the outer edge of the preferred scintillator array 112 (outlined in dashed lines). For the purposes of the explanation below, the line 2—2 will be referred to as the y-axis and the line 3—3 will be referred to as the x-axis.

An x-ray source is positioned such that an even spread of x-rays is directed at the x-ray shield 440. Suitable measurement means are connected to the output leads of the PMT 416 to measure the electrical signals produced by the specific PMT channels which correspond to scintillator elements 170 located adjacent to the x-ray transmissive windows 442, 444, 446, and 448. Such measurement means may comprise, for example an amplifier and a comparator to count the number of light photons detected by the PMT 416, employing photon counting circuitry described more fully in copending patent application Ser. No. 08/386,861,, which has been incorporated herein by reference in its entirety. Suitable means are preferably employed to amplify and balance the output signals from the PMT channels, as described more fully in copending U.S. patent application Ser. No. 08/386,861, which has been incorporated herein by reference in its entirety.

The alignment procedure is initiated by a directed emission of x-rays spread evenly across the face of the x-ray shield 440. If the scintillator elements are optimally aligned with their corresponding PMT channels along the y-axis, then the output signals from the PMT channels which correspond to the scintillator elements 170 adjacent to x-ray windows 442 and 446 should be maximized. To effect a y-axis alignment, the scintillator array 112 is positionally adjusted along the y-axis in the manner described more fully in connection with FIGS. 12 and 13, and after each adjustment, another directed emission of x-rays is evenly spread across the face of x-ray shield 440. This process repeats until maximum levels of output signals are measured for the PMT channels corresponding to the y-axis scintillator elements 170 adjacent x-ray windows 442 and 446. Similarly, the x-axis alignment process involves the manipulation of the scintillator array 112 along the x-axis, in the manner more fully described in connection with FIGS. 8–9, until further beams of x-rays directed at the x-ray shield 440 produce maximum levels of output signals measured for the PMT channels corresponding to the x-axis scintillator elements 170 adjacent x-ray windows 444 and 448.

Once the scintillator array 112 is optimally aligned along the x and y axes, the next step is to rotationally align the scintillator array 112. As with the x and y alignment, the process is initiated by an even spread of x-rays directed at the outer face of x-ray shield 440. When the scintillator array 112 is rotationally adjusted to the optimal positioning, then the level of visible light transferred to the PMT 416 should be at a maximum. Therefore, the scintillator array 112 is manipulated rotationally in the manner described in connection with FIGS. 8–9, and a directed beam of x-rays are emitted after each adjustment, until any further rotational manipulations would result in less visible light being detected by the PMT 416. If necessary, the y-axis and x-axis alignment procedures can be repeated after the rotational adjustments have been made to correct x or y-axis misalignments introduced by the rotational adjustments.

An alternate alignment method comprises the use of a high-power microscope to optimally align the scintillator elements 170 with their corresponding photomultiplier tube channels. According to this method, the input faces of the scintillator elements 170 are polished as well as the output faces. The multi-detector array assembly 350, is mounted to an alignment stand and a microscope is placed along the input face of the scintillator crystal array 112. To effect the optimal alignment, the microscope is initially positioned over the input face of one of the scintillator elements 170 along the outer perimeter of the scintillator array 112. The positioning screws within the multi-detector array 350 are manipulated, in the manner described in connection with FIG. 9, such that fiber optic imaging taper 412 is repositioned relative to the scintillator array 112. The positioning screws are manipulated until the photomultiplier tube channel corresponding to the observed scintillator element 170 is optically centered in relation to the scintillator element 170. The process is then repeated with another scintillator element 170 along the outer perimeter of the scintillator array 112 directly opposite the just aligned scintillator element 170. The above process is repeated until all the scintillator elements 170 along the outer perimeter of the scintillator array 112 are properly aligned.

Figure 17:
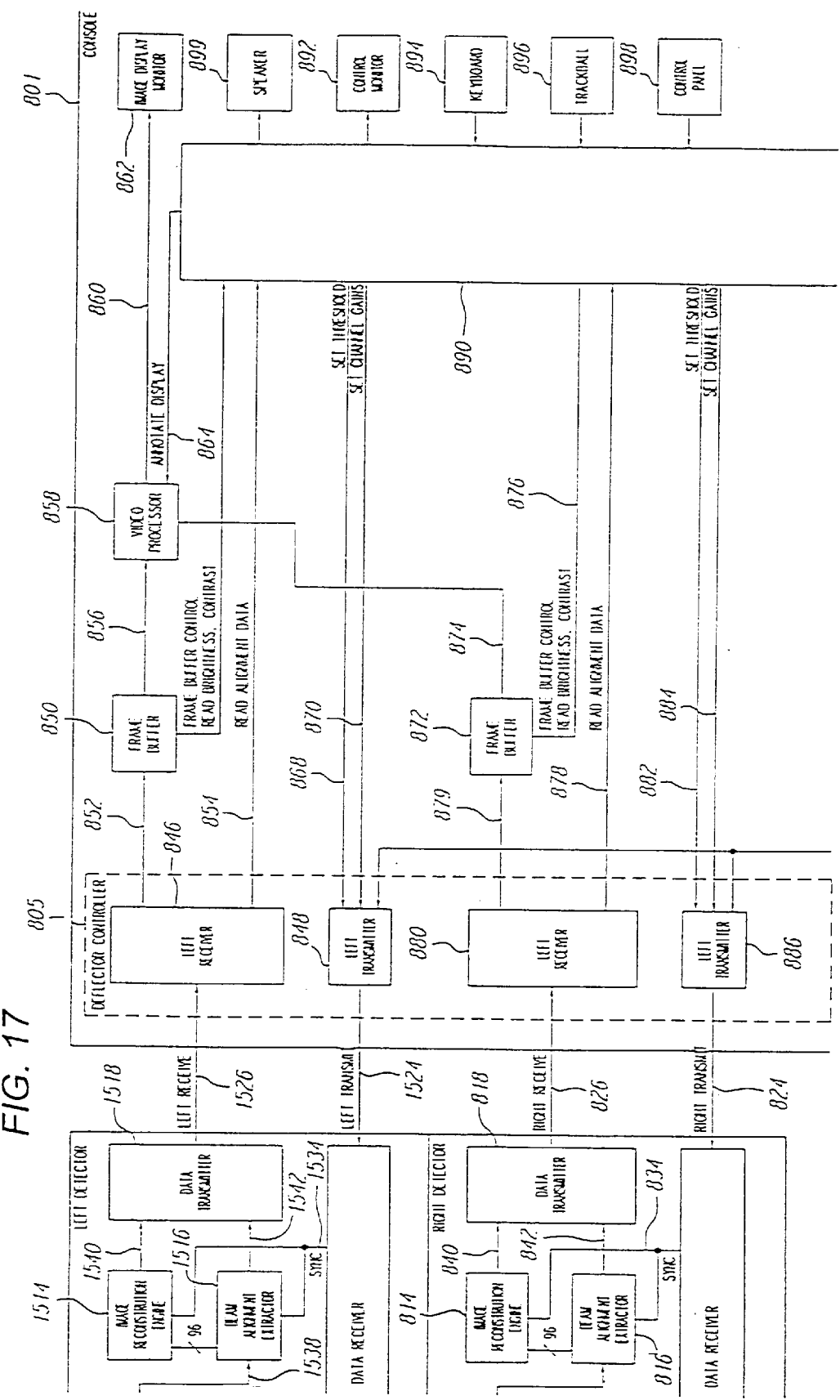

FIGS. 16–17 functionally diagram preferred right 822 and left 1522 detectors of the present invention. Since both detectors function in a similar fashion, only the right detector 822 will be discussed in detail. The components bearing a number having the same last two digits perform the same function.

Scintillator array 802 preferably comprises ninety-six elements and in response to x-ray photons generates visible light energy which is transmitted to photomultiplier tube 806 comprising ninety-six channels via a tapered fiber-optic bundle 804. The photomultiplier tube 806 converts the received light energy into electrical signals which are sent to signal conditioner 810 via 96 separate electrical connections 836. These signals are referred to herein as raw partial image pixel information. The multi-detector array preferably comprises a scintillator array 802, fiber-optic taper 804 and photomultiplier tube 806. It should be noted that while the preferred embodiment includes 96 channels, more or less than that number are within the spirit and scope of the present invention. Photomultiplier tube 806 is powered by photomultiplier tube power supply 808.

Signal conditioner 810 is preferably comprised of 48 circuit boards. Each circuit board comprises two sets of signal conditioning amplifier circuits, with each signal conditioning amplifier circuit feeding its output to a corresponding discriminator. Thus 96 sets of signal conditioning amplifier circuits and discriminators are employed, with each set paired to a corresponding photomultiplier tube channel. The signal conditioner 810 outputs ninety-six separate signals for every step of the electron beam. This information is referred to as the partial image pixel information.

The outputs of the signal conditioners are preferably input into the beam alignment extractor 816. Beam alignment extractor 816 processes the information from each position of the electron beam on the target and sends processed alignment data to data transmitter 818. Clock signals are sent to the beam alignment extractor from data receiver 812.

Beam alignment extractor 816 sends the partial image pixel information from signal conditioner 810 to image reconstruction engine 814. For diagnostic purposes, the partial image pixel information sent from signal conditioner 810 may be modified by the beam alignment extractor 816 before it is sent to the image reconstruction engine 814. Image reconstruction engine 814 processes the partial image pixel information and sends image pixel data to data transmitter 818. The image reconstruction engine 814 receives clock signals from data receiver 812 via electrical connection 834.

The detector controller 805 for the detectors 822 and 1522 preferably transmits and receives optical signals to and from the detectors. Right receiver 880 receives image pixel data and beam alignment data from the right detector 822 through high-speed fiber-optic cable 826. Right detector 822 transmits this data through a data transmitter 818, which preferably includes circuitry for conversion of the signals from image reconstruction engine 814 and beam alignment extractor 816 into a serial signal. This serial signal is converted into light pulses using an LED. Right receiver 880 also comprises a light detector and related circuitry for receiving and decoding the light pulse from a serial signal into parallel signals. The beam alignment data is transmitted to control computer 890. The image pixel data is preferably transmitted to frame buffer 872. The left receiver 846 operates in a similar fashion to receive image pixel data and beam alignment data from the left detector 1522.

Right transmitter 886 comprises circuitry for converting parallel signals into serial signals. Right transmitter 886 receives, among other signals, signals to set channel gains and threshold levels from control computer 890. Right transmitter 886 also receives clock signals from a beam deflection lookup table. These signals are converted into serial signals which are then transmitted as light pulses to the right detector 822 through high-speed fiber-optic cable 824. Right data receiver 812, which contains a light detector and circuitry to convert light pulses into parallel signals receives these signals. The signal to set channel gain is transmitted to the signal conditioner 810 through wire 828. The left transmitter 848 operates in a similar manner to communicate control signals to the left detector 1522.

Image pixel data transmitted to right frame buffer 872 is subsequently transmitted to video processor 858 where in a stereoscopic system, it is preferably combined with image pixel data from left frame buffer 850. Brightness and contrast information are transmitted from the right frame buffer 872 and from the left frame buffer 850 to control computer 890. This information is used to set the output of the x-ray source for optimal image quality and x-ray exposure control. Control computer 890 transmits information to the video processor 858 for annotation of the image display. The output of video processor 858 is preferably sent to image display monitor 862 where the image is displayed.

The electron beam 40 in x-ray source 10 is preferably precisely aligned such that it will illuminate the area on the target layer at the exact point at which the axis of the collimator hole intersects the target layer. When no object is interposed between the target 50 and the multi-detector array 110, such a precisely aligned electron beam will result in a near symmetrical distribution of x-ray intensity across the face of detector elements 360 of the multi-detector array 110, within the pseudo-circle 400. An electron beam which is not so precisely aligned may create a non-symmetrical distribution of x-ray intensities across the face of the detector elements 160 of the multi-detector array 110.

Alignment of the electron beam behind the collimator holes is preferably accomplished with a 2-step process. An initial alignment procedure is preferably performed to approximate the correct positioning of the electron beam 40. The initial alignment procedure is preferably followed by a fine alignment procedure that optimizes the position of the center of the electron beam profile relative to the collimator holes.

The first step of the preferred initial alignment procedure is comprised of locating the electron beams using a-priori knowledge related to the physical, electrical and magnetic properties of the scanning system. The relative spacing of the electron beam positions may be reasonably correct at this point, but the absolute positions of the electron beams may not be because of the difficulty in indexing the electron beam position array to the collimator holes, and because of small cumulative errors. Therefore, a "dithering" process is preferably employed whereby several measurements are made by making small adjustments of the index position for a whole array of electron beam positions. Typically, 25 measurements are made where the index point is moved in a 5 by 5 x-y grid. The total size of the grid is approximately the spacing of one collimator hole. The data collected for each measurement consists of the total intensity measured by the multi-detector array for each of the collimator holes.

The collected data for a give collimator hole will preferably be an array of 25 values. Many of the values will indicate that little or no x-ray flux impinged upon the multi-detector array, but several will indicate that at least part of the electron beam produced x-rays that impinge upon the multi-detector array. An approximate optimum beam position location is determined by mathematically fitting a multi-dimensional surface to the illuminated data.

Thus, approximate optimum beam positions are determined by this procedure. These positions are refined using the fine alignment method described below.

To initiate the fine alignment procedure, initial x-deflection values and y-deflection values are preferably computed for each collimator aperture, employing the initial alignment procedure described above. Using these computed initial deflection values the electron beam is scanned across the target, momentarily stopping at each of the computed locations corresponding to the computed x and y deflection values. The partial image pixel information obtained from each detector element for each x-ray pencil beam generated by stopping at each computed location is analyzed for even distribution of the x-ray intensity over several frames. (A complete scan of the target is referred to as a frame.) If the analysis results in a determination that the distribution of x-ray intensity is not even, new x-deflection values and/or y-deflection values are calculated and the alignment procedure is repeated to ensure optimal distribution.

The preferred way of analyzing the distribution of x-ray flux across the face of the multi-detector array is to compare the average intensity of the x-ray rays detected by selected areas of the face of the multi-detector array. This is preferably accomplished by dividing the preferred ninety-six detector element multi-detector array into eight areas comprising substantially the same number of detector elements.

Figure 18:
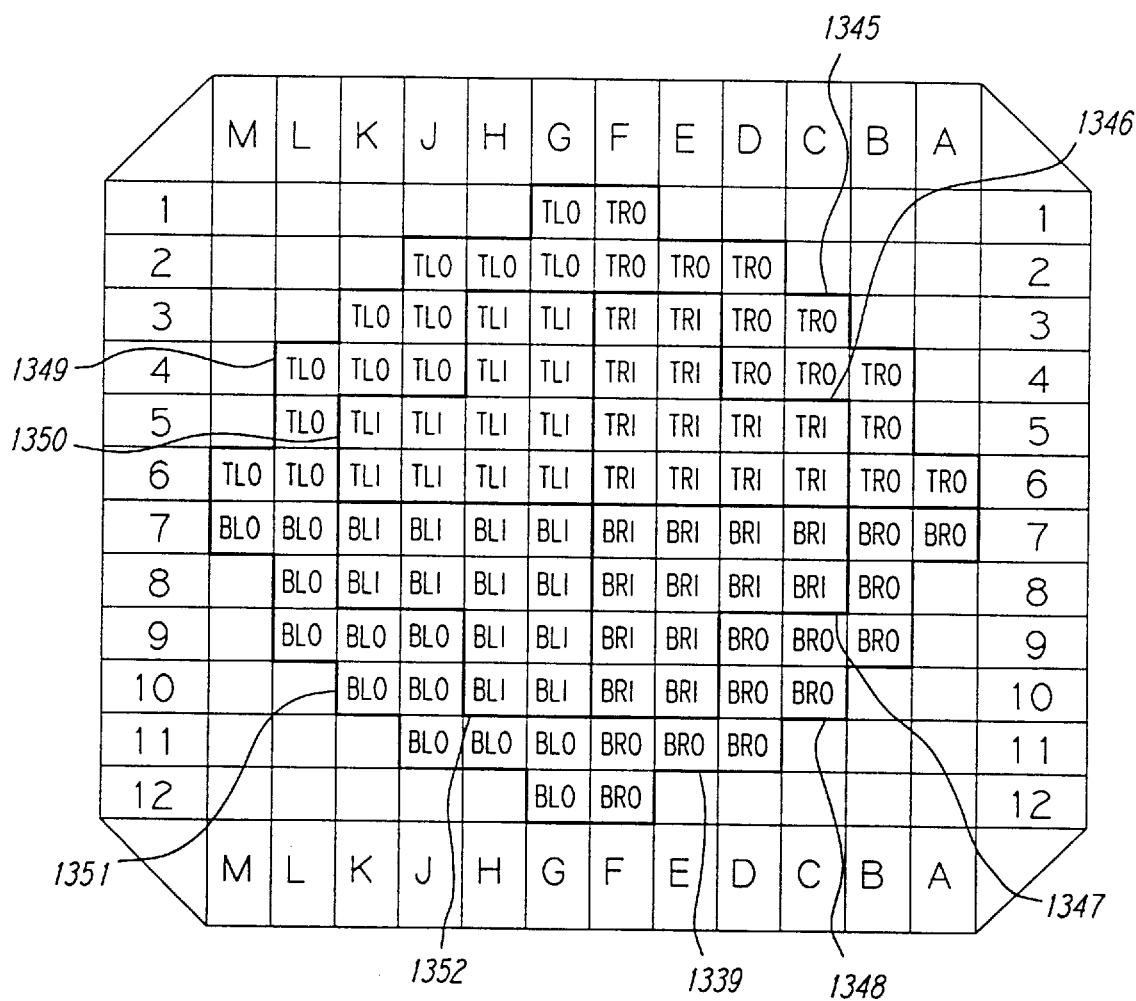
FIG. 18 is a diagram showing the preferred beam alignment octant arrangement.

FIG. 18 is a representational diagram of the face of a multi-detector array divided into eight areas. Each of the eight areas is referred to as an "octant." The eight octants are identified as the top right outer octant ("TRO") 1345, top right inner octant ("TRI") 1346, top left outer octant ("TLO") 1349, top left inner octant ("TLI") 1350, bottom right inner octant ("BRI") 1347, bottom right outer octant ("BRO") 1348, bottom left outer octant ("BLO") 1351, and bottom left inner octant ("BLI") 1352.

In the preferred embodiment, the 96 detector elements 1339 are evenly divided among the eight octants. Therefore each octant contains 12 detector elements 1339. However, it is contemplated that other arrangements may be used in the present invention. For example, an alternative arrangement could consist of 13 detector elements 1339 associated with each inner octant, with 11 detector elements 1339 associated with each outer octant.

The beam alignment calculations are preferably determined separately for the x-axis 1662 and the y-axis 1660. The preferred sequence of steps to determine the proper beam alignment along the y-axis 1660 are as follows. The process begins when an x-ray pencil beam from a single collimator aperture strikes the scintillator elements of multi-detector array 110.

The total intensity values for each octant is summed by counting the number of x-ray photons which are received by each detector element 1339 associated with each octant. For example, arbitrarily selecting the variable V to refer to the sum of the photon counts in a particular area, $V_{TRO}$ is the sum of all the photon counts in the TRO octant 1345. Similarly, $V_{TRI}$ is the sum for the TRI octant 1346, $V_{TLO}$ for TLO octant 1349, $V_{TLI}$ for TLI octant 1350, $V_{BLO}$ for BLO octant 1351, $V_{BLI}$ for BLI octant 1352, $V_{BRI}$ for BRI octant 1347, and $V_{BLO}$ for BLO octant 1348. The intensity values for each octant, for each x-ray pencil beam from each collimator aperture for each of a predetermined number of succeeding frames, is accumulated. The presently preferred embodiment uses the octant values from 100–120 frames to perform the beam calculations. Thus, there are a total of eight octant values for each beam/aperture combination.

The accumulated values for the octants in the top and bottom halves of the PMT array are then separately summed. Thus the top octant accumulated value is $A_{top} = V_{TRO} + V_{TRI} + V_{TLI} + V_{TLO}$. The bottom octant accumulated is $V_{bottom} = V_{BRO} + V_{BRI} + V_{BLI} + V_{BLO}$.

Next the top octant accumulated value is compared to the bottom octant accumulated value. This comparison produces a y-axis alignment factor ($AF_{y-axis}$) which is a measure of the accuracy of the x-ray beam alignment with respect to a particular aperture along the y-axis. The formula to determine the $AF_{y\ axis}$ is:

$$AF_{y-axis} = \frac{V_{-top} - V_{bottom}}{V_{-top} + V_{bottom}} \qquad \text{EQ. 7}$$

If the electron beam is properly aligned with the aperture under analysis along the y-axis, the accumulated intensity values for the top and the bottom octants should be the same. Thus when $V_{top}$ is equal to $V_{bottom}$, $AF_{y-axis} = 0$ and the beam is properly aligned along the y-axis for the aperture under analysis.

If the electron beam was positioned to favor the top half of the multi-detector array, then $V_{top}$ will be greater than $V_{bottom}$. This results in $AF_{y-axis} > 0$. If the electron beam is positioned to favor the bottom half of the multi-detector array, then $V_{top}$ will be less than $V_{bottom}$. This results in $AF_{y-axis} < 0$. The value of $AF_{y-axis}$ generally indicates the amount the y-deflection value should change to optimize the alignment.

The method to determine the optimal electron beam alignment along the x-axis is similar. For this calculation, the accumulated values for the left and right octants are separately summed. Thus the right octant accumulated value is $V_{right} = V_{TRO} + V_{TRI} + V_{BRO} + V_{BRI}$. The left octant accumulated value is $V_{left} = V_{TLO\ +\ VTLI} + V_{BLO} + V_{BLI}$. The formula to determine the x-axis alignment factor ($AF_{y-axis}$) is:

$$AF_{x\text{-}axis} = \frac{V_{right} - V_{left}}{V_{right} + V_{left}} \qquad \text{EQ. 8}$$

Calculations almost identical to those used for the y-axis alignment are used to determine the optimal alignment of the electron beam along the x-axis.

The x-axis and y-axis alignment factors are transmitted to the control computer 890. Control computer 890 processes these alignment factors to determine the amount of correction required at the x-ray source 798 to optimally align the x-ray pencil beam. The control computer 890 next updates the beam deflection lookup tables.

By adjusting the electron beam's positioning on the target 1250, x-rays are emitted from the target at a different position relative to the collimator grid aperture. The x-ray pencil beams passing through the collimator grid aperture would then illuminate the multi-detector array at a corrected optimally aligned position.

This alignment may be performed whenever the system is activated, at preset intervals or continuously.

While the previous discussion explores alignment calculations along the x and y axes, other octant calculation methods are also contemplated within the boundaries of this aspect of invention. For example, angular alignment calculations may be performed by comparing the accumulated value of the top right octants with the values of the bottom left octants and the top left octants with the bottom right octants.

Figure 19:
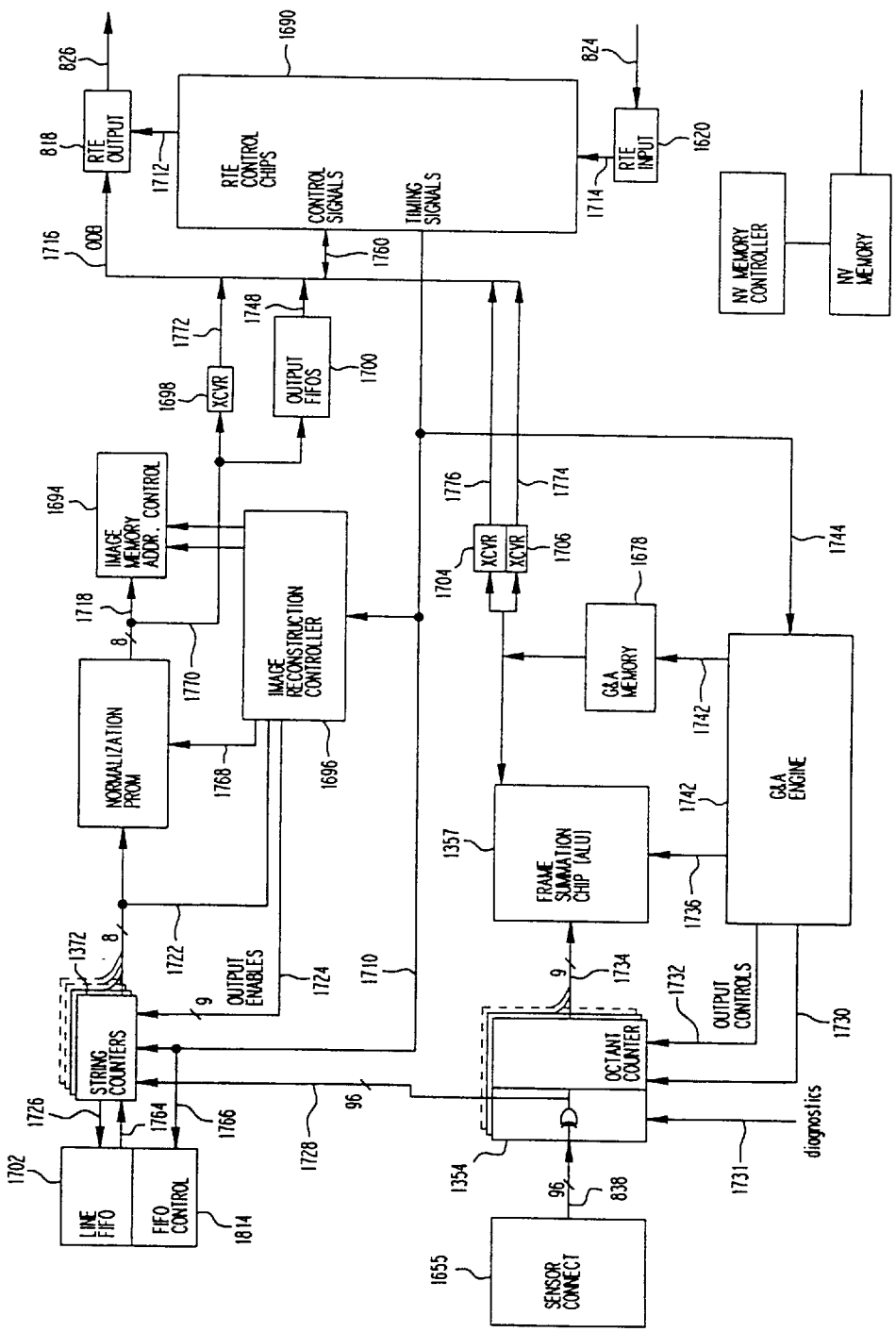
FIG. 19 comprises a partial functional block diagram of an image reconstruction engine.
Figure 20A:
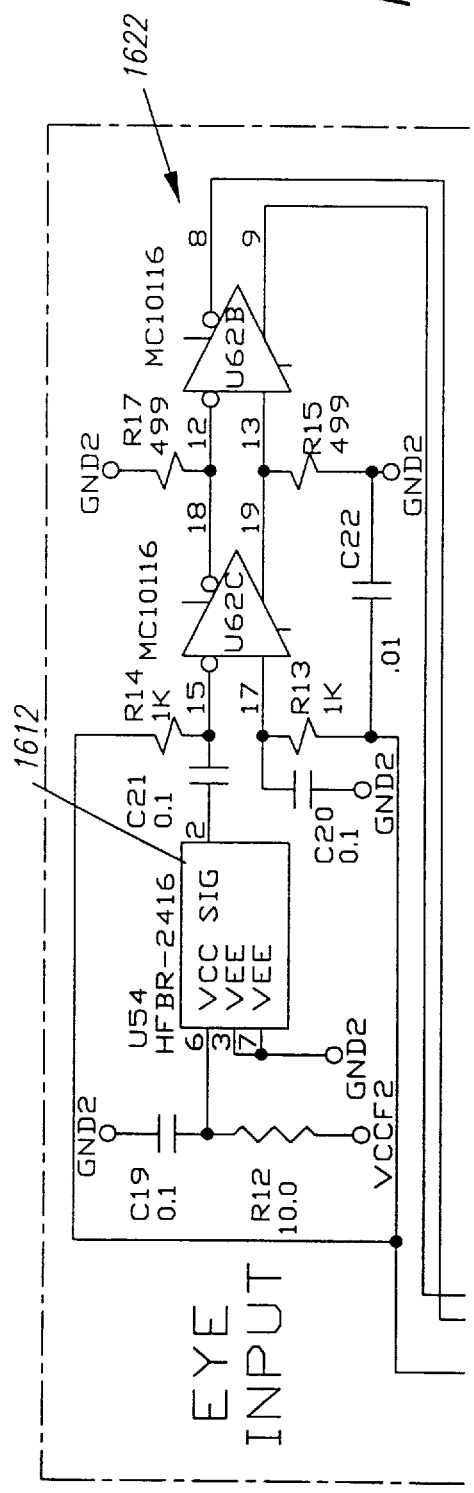
Figure 20B:
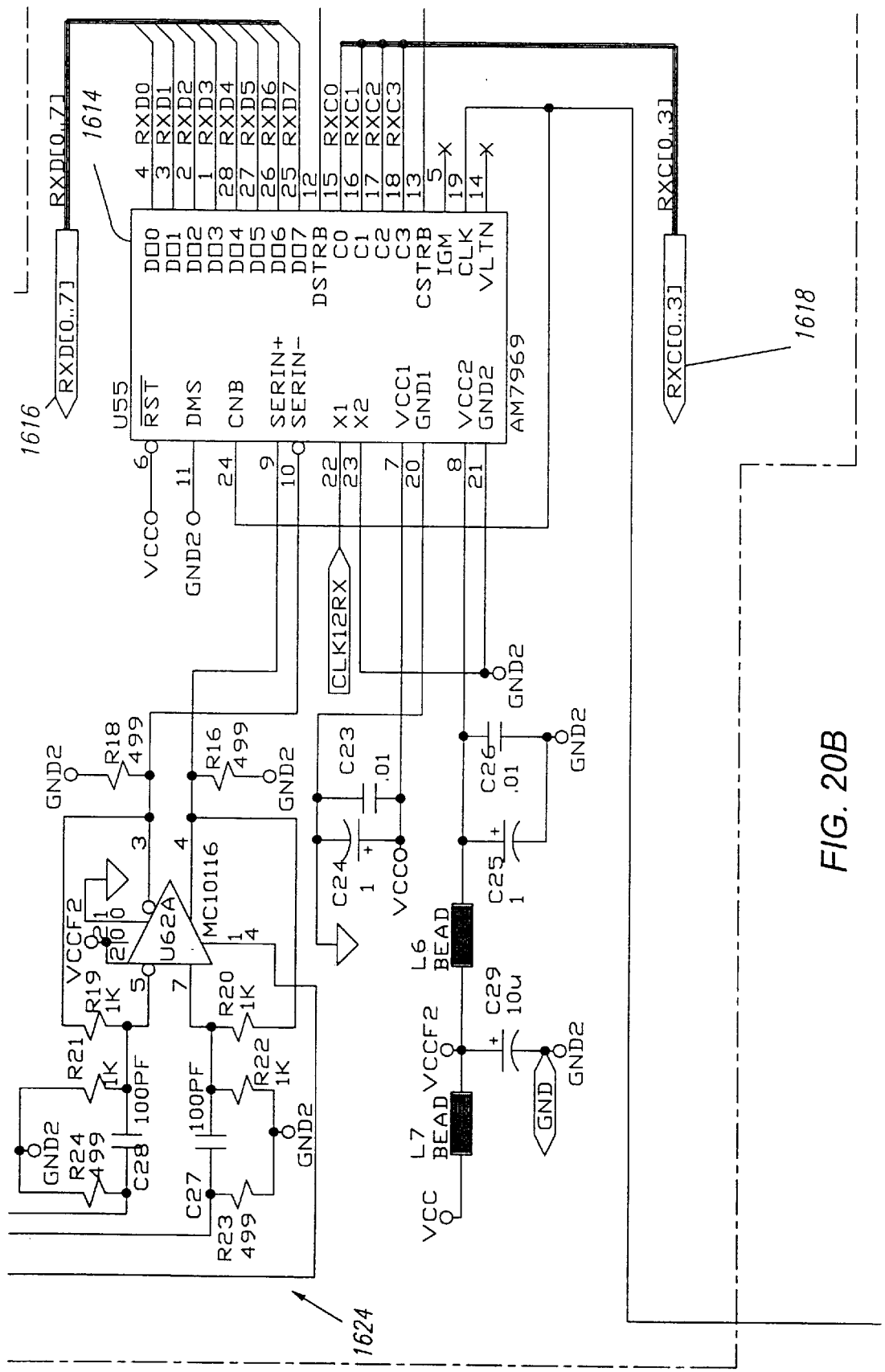
Figure 20C:
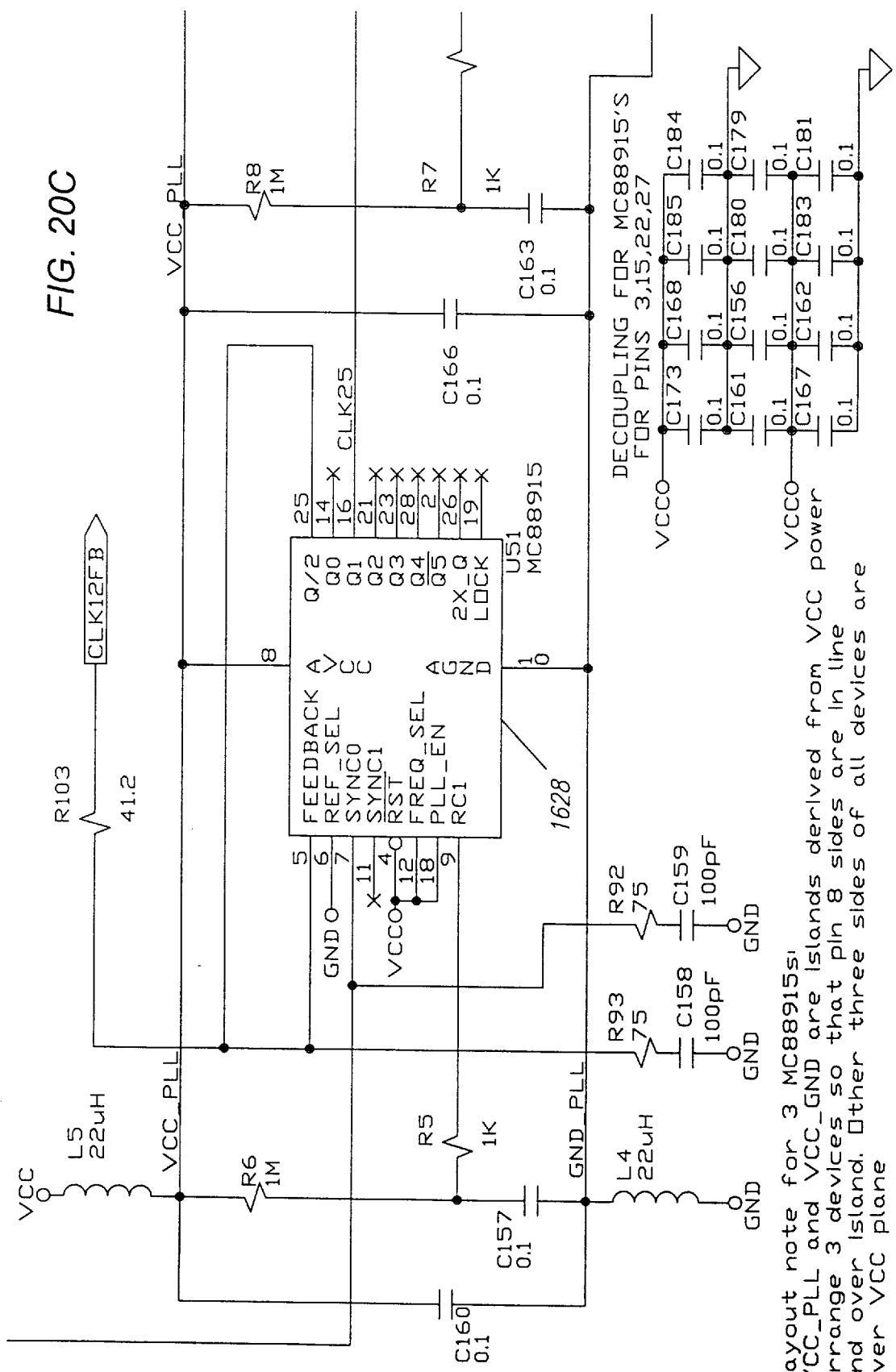
Figure 20D:
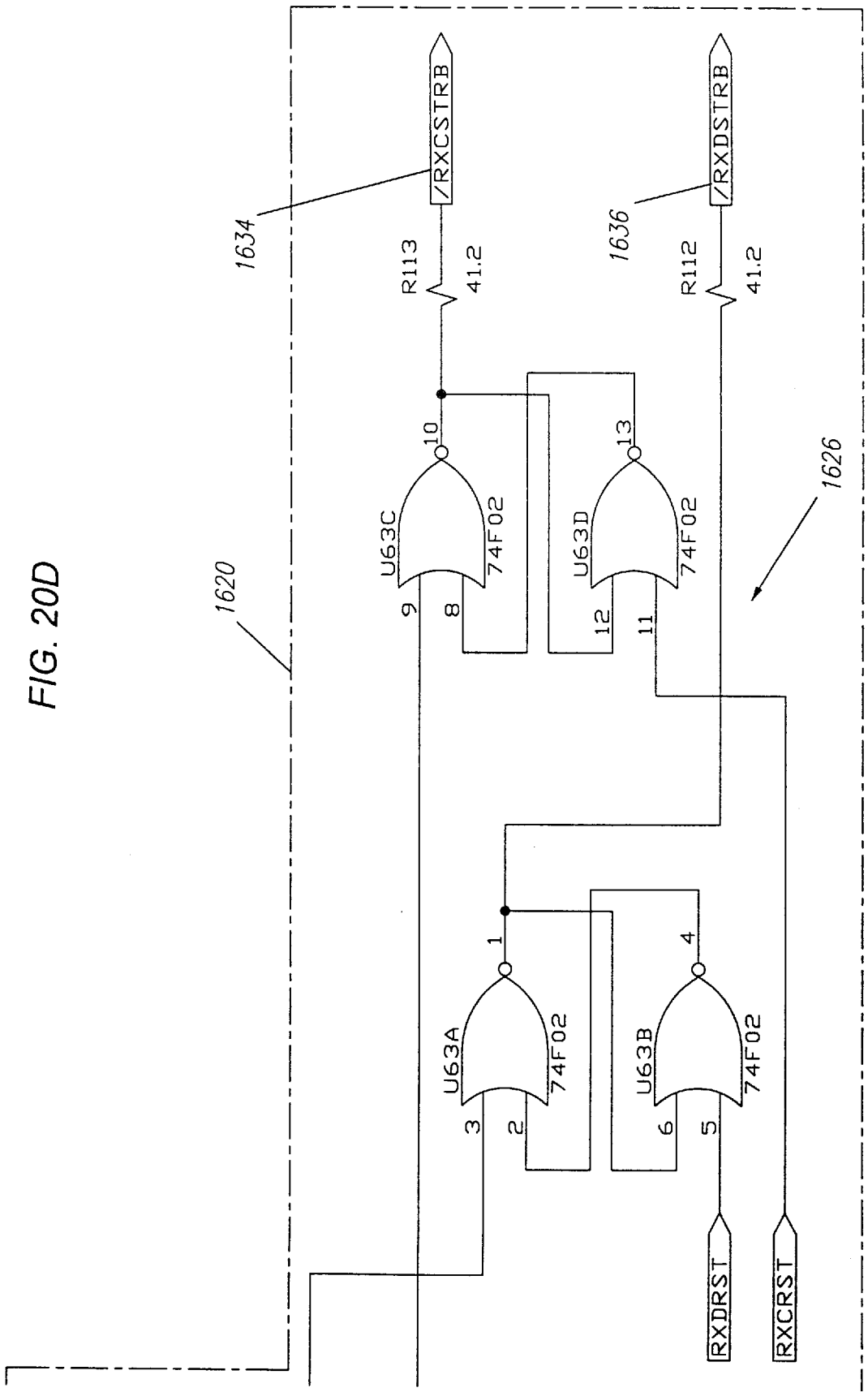
Figure 20E:
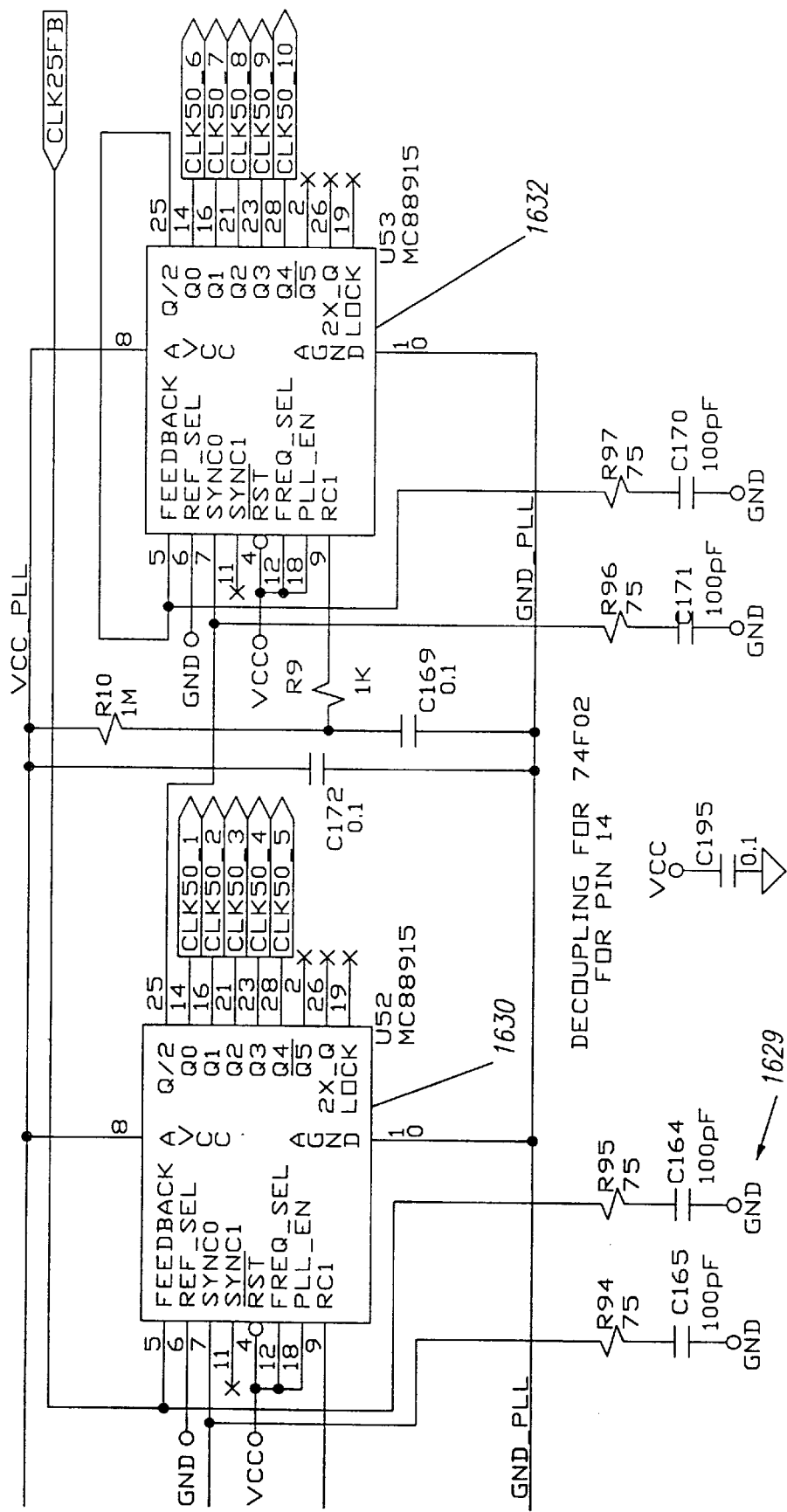

FIG. 19 is a block diagram of the circuitry for the beam alignment extractor and image reconstruction engine. The output signals of the signal conditioner 810 are input, via connectors 1655, to the beam alignment extractor.

The conditioned partial image pixel signals from each detector element for each step of the electron beam are input to RTE octant counters 1354. There are preferably eight RTE octant counters. Each of the octant counters receives the conditioned partial image pixel signals from one of the eight octants. Each RTE octant counter 1354 splits the conditioned partial image pixel signals into two essentially identical signals. One set of the conditioned partial image pixel signals is used to analyze the optimal alignment of the electron beam. The other set is transmitted to the image reconstruction engine ultimately to be used to reconstruct the image of the object being investigated.

Each RTE octant counter 1354 then processes the input conditioned image pixel signals to obtain a total photon count for its corresponding octant. In sequential order, the RTE octant counters 1354 next transmit the total photon sum for each octant to the frame-summation chip 1357. This process is controlled and outputs to the frame summation chip are enabled by control signals communicated to the RTE octant counters 1354 from the gain & alignment engine 1674.

The frame-summation chip 1357 is an arithmetic logic unit ("ALU"). For each photon count input from a RTE octant counter 1354, the frame-summation chip 1357 also inputs an accumulated octant value from the gain & alignment memory 1678. This accumulated octant value corresponds to the sum of the photon counts from one or more previous frames for the same octant and for the same aperture on the collimator which was illuminated to produce the present photon count. The frame summation chip 1357 adds the photon count to the accumulated octant value to produce a new octant value, which is then stored at the gain & alignment memory 1678.

The gain & alignment engine 1674 controls the operation of the octant counters 13S4, frame-summation chip 1357 and gain & alignment memory 1678. After approximately 100–120 frames of information have been collected at the gain & alignment memory 1678, the gain & alignment engine 1674 communicates instructions to the gain & alignment memory 1678 to output the beam alignment information, which is transmitted through transceivers 1704 and 1706 to the RTE output circuits 818.

The string counters 1372 input partial image pixel signals from the RTE octant counters 1354. The string counters 1372 process partial image pixel values to reconstruct data values for complete image pixels.

During the image reconstruction process, partially constructed image pixel values are stored by the string counters 1372 at the line FIFO ("first in first out") chips 1702. After 166 items of partial image pixel values are input into a line FIFO chip 1702, each successive item stored at that line FIFO chip 1702 will cause the line FIFO chip 1702 to transmit the then earliest stored string data value back to the string counters 1372. Line FIFO 1702 receives timing signals from the RTE control chips.

The string counters 1372 transmit data values for complete image pixels to the normalization PROM 1692. The normalization PROM adjusts this data value based upon the number of active detector elements which contribute partial image pixel information for that image pixel. The normalization PROM 1692 receives control signals from the image reconstruction controller 1696 through electrical connection 1768.

Normalization PROM 1692 outputs normalized image pixel information to the output FIFOs 1700 through electrical connection 1746. Three lines of normalized image pixel information are stored at the output FIFOs 1700 before the normalized image pixel data is transmitted to the RTE output circuit.

The normalized image pixel information from the normalization PROM 1692 is also input to the image memory unit 1694. The normalized image pixel information for the entire image is stored and properly ordered at the image memory unit 1694. The control computer can access this image data through transceiver 1698.

The image reconstruction controller transmits the control signals which operate the components of the image reconstruction engine. Control and addressing signals are communicated to the image memory unit 1694 on electrical connections 1758 and 1756. Control signals are sent, via electrical connection 1768, to the normalization PROM. The image reconstruction controller 1696 communicates control signals, via electrical connection 1724, to the string counters 1372.

Control information from the control computer 890 are input to the real-time eye through RTE input circuit 1620, which receives light pulses from high-speed fiber-optic cable 824. The RTE input circuit 1620 comprises a light detector and circuitry which detects and demodulates the light pulses into electrical signals which contain the control information from the control computer 890. The control information is sent from RTE input circuit 1620 to the RTE control chips 1690 through electrical connection 1714.

The RTE control chips 1690 send timing signals to the RTE circuitry through electrical bus connection 1710. The RTE control chips 1690 send control signals to the RTE circuitry through electrical bus connection 1760. RTE output circuit 818 sends image reconstruction and gain & alignment information to the control computer 890 through highspeed fiber-optic cable 826. RTE output circuit 818 comprises a high radiance LED and circuitry which converts electrical signals into light pulses.

Turning to FIGS. 20A–E, a detailed diagram is presented of the RTE input circuit 1620. RTE input circuit 1620 receives light pulses from right transmitter 880. Light pulses are detected and converted to an electrical signal by the fiber-optic receiver 1612. The electrical signal is filtered and shaped by circuits 1622 and 1624. The electrical signal is then input to the taxi chip 1614, a standard AM7969 chip available from AMD Corp, which functions as a serial to parallel converter. The electrical input signal was necessarily in a serial format because of its transmission through a fiber-optic cable. Four bits of control signals and eight bits of data signals are output from taxi chip 1614. While the present description of FIGS. 20A–E is directed to the RTE input circuit 1620 of the data receiver 812, a similar circuit exists for other components of the present invention which receives light pulses through fiber-optic cables.

Phase locked loop (PLL) circuit 1629, located in data receiver 812, receives and locks onto a master 12.5 MHz clock 15 signal that is generated in the programmable scan controller. This master clock signal drives both the taxi chip 1614 in the data receiver 812 and the taxi chip 1602 in the data transmitter 818 to generate an output at a clock rate of 12.5 MHz. MC88915 clock doublers 1628, 1630, and 1632 are used to quadruple the 12.5 MHz clock signal to a 50 MHz frequency. Timing circuit 1626 uses this 50 MHz clock to synchronize taxi chip 1614 with the other components of the beam alignment extractor and image reconstruction circuitry. Timing circuit 1626 generates a data strobe signal which is transmitted via electrical connection 1636. Timing circuit 1626 generates a control strobe signal which is transmitted via electrical connection 1634.

Figure 21B:
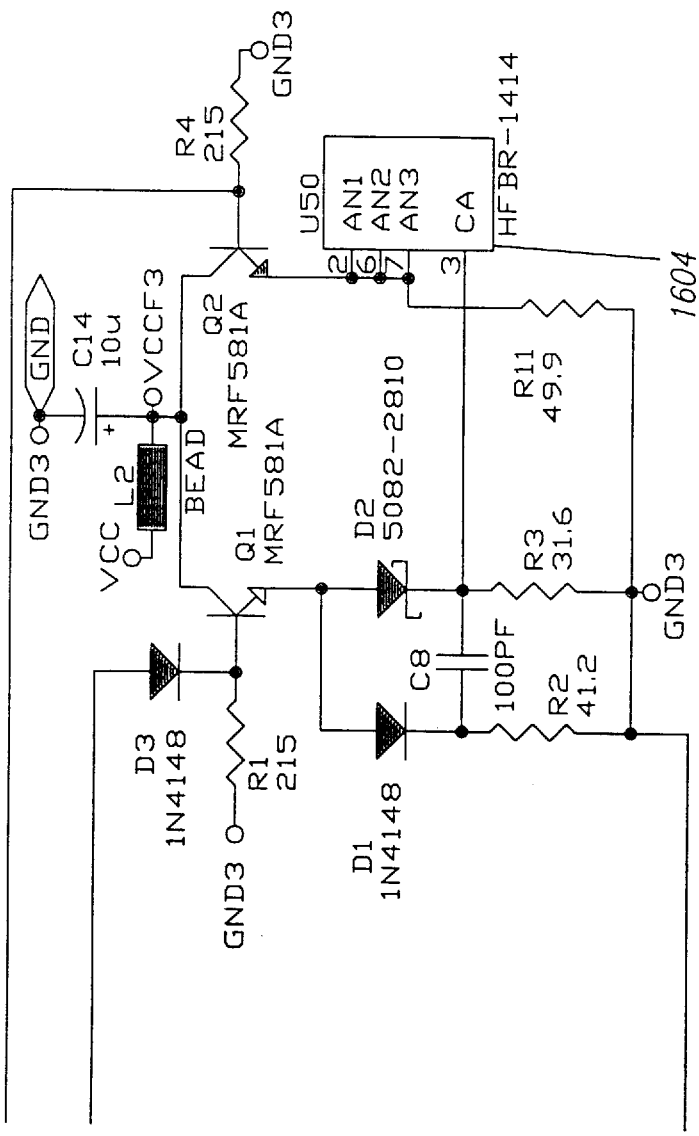
Figure 22B:
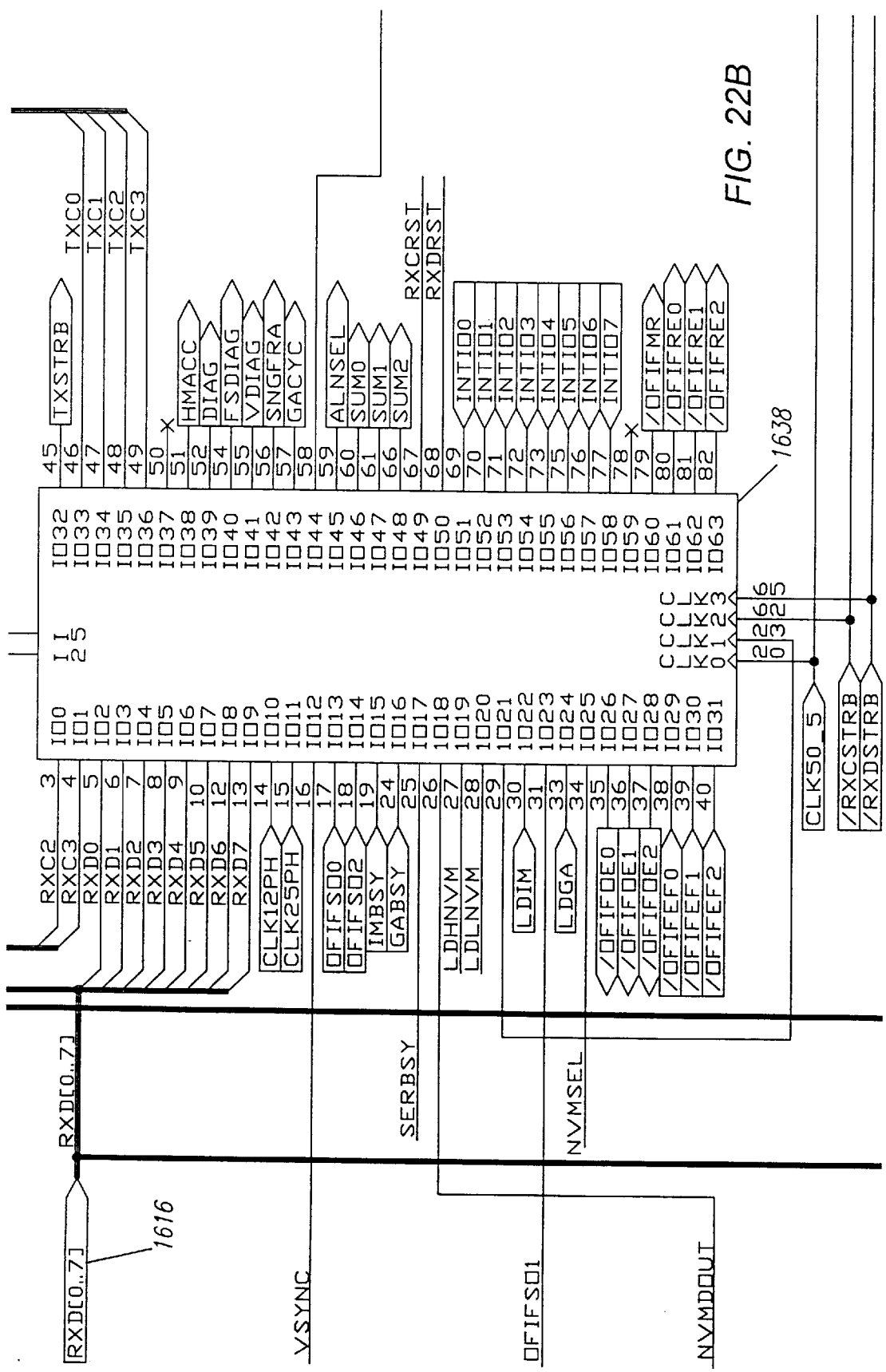
Figure 22C:
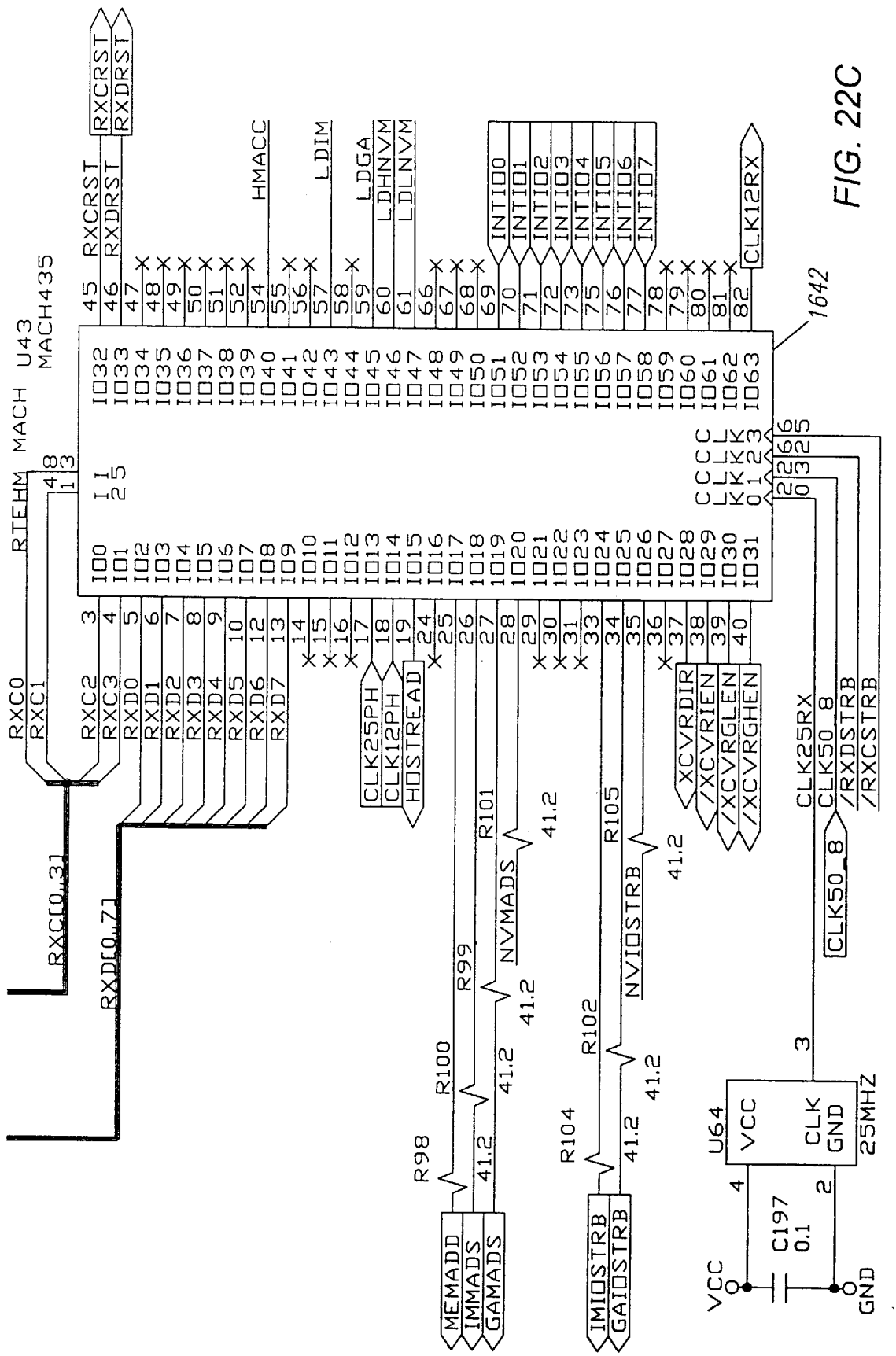
Figure 22D:
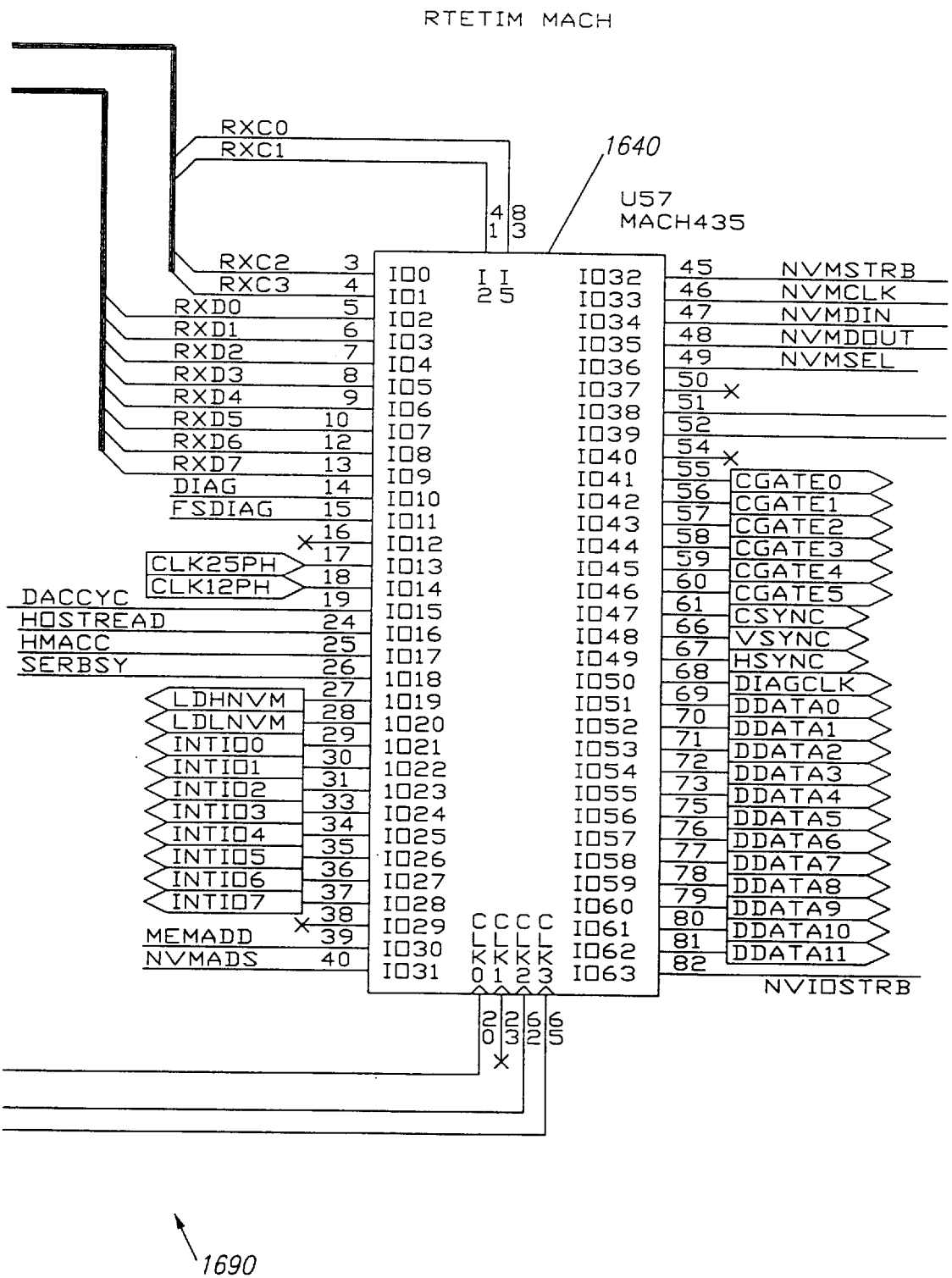
Figure 22E:
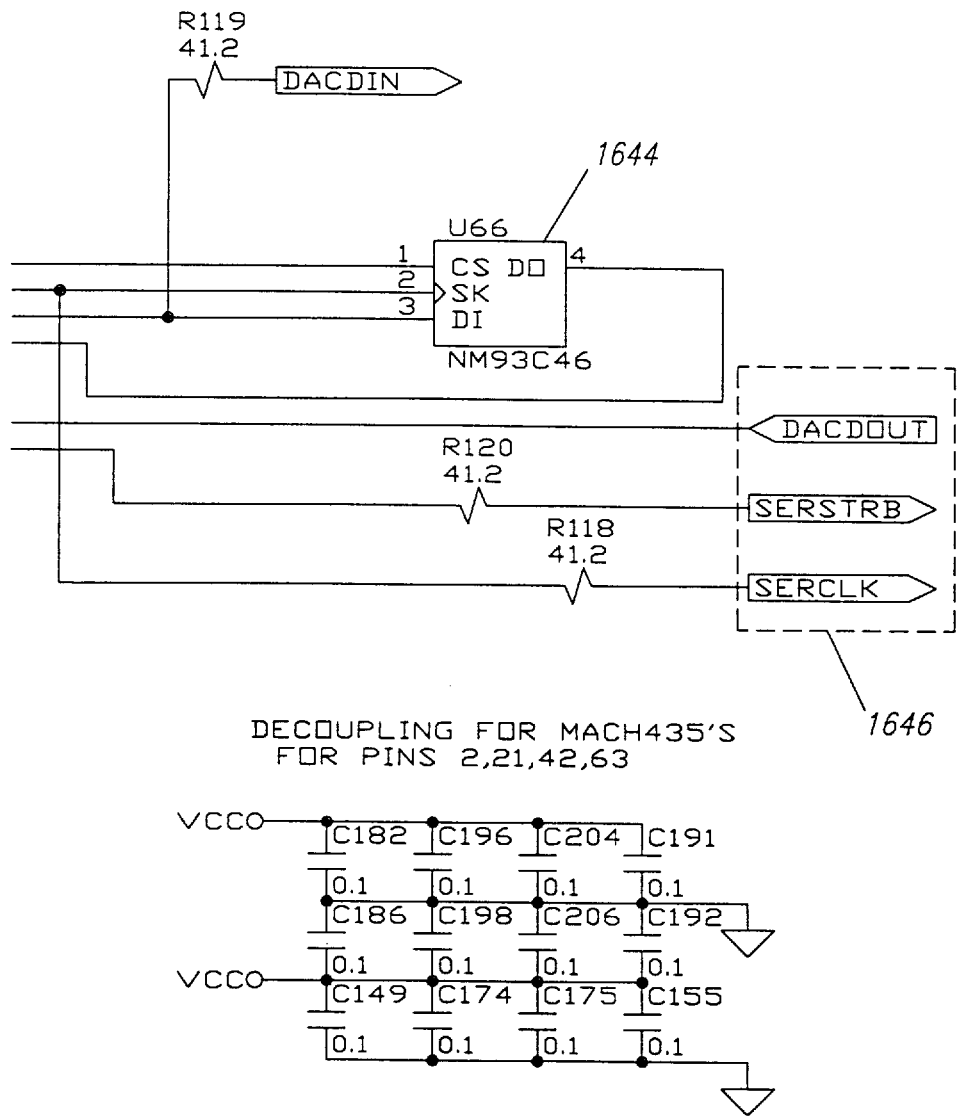

FIGS. 21A–B diagrams the RTE output circuit 818, which is also referred to as the right data transmitter. Taxi chip 1602 is another standard AM7968 chip available from AMD Corp. which also functions as a parallel to serial converter. Parallel data bits from the image reconstruction engine and the beam alignment extractor are input to the taxi chip 1602, which outputs a serial data signal. This serial data signal is then shaped by the conditioning circuitry 1610. The output signal from the conditioning circuit 1610 is sent to fiber-optic transmitter 1604, which transforms the serial data signal into light pulses through the use of a high-radiance LED. The light pulses are sent to a data receiver 880 through high-speed fiber-optic cable 826. While the present description of FIGS. 21A–B is directed to the RTE output circuit 1620 of the real-time eye, a similar circuit exists for other components of the present invention which transmits light pulses through fiber-optic cables.

FIGS. 22A–E is a circuit diagram of the RTE control chips 1690 which are located in the data receiver 812. Information from the control computer 890 that is acquired through the RTE input circuit 1620 is distributed to the various components of the multi-detector array through the RTE control chips 1690, each of which is a MACH435 programmable IC chip available from AMD Corp. Data outputs from the RTE input taxi chip 1614 are input to the RTE control chips via 8 bit electrical connection 1616. Control information outputs from the RTE input taxi chip 1614 are input to the RTE control chips via 4 bit electrical connection 1616.

Data acquisition control chip 1638 distributes control information relating to the selection of data that is acquired and processed by the components of the multi-detector array 822. Host memory control chip 1642 communicates instructions to the image memory unit 1694 and the gain & alignment memory unit 1678. Timing control chip 1640 communicates timing and diagnostic signals to the circuitry of the beam alignment extractor and the image reconstruction engine. The timing control signals for the signal conditioner 1510 is output from the timing control chip 1640 through connection 1646. 1 Kbyte of nonvolatile memory 1644 stores calibration information for the circuitry of the beam alignment extractor and the image reconstruction engine. The preferred software modules for data acquisition control chip 1638, host memory control chip 1642, and timing control chip 1640 are included in Appendix A.

Figure 23:
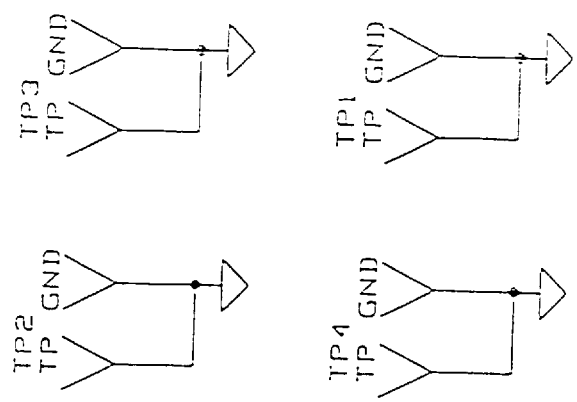
FIG. 23 is a layout arrangement plan for FIGS. 23A–B.
Figure 23B:
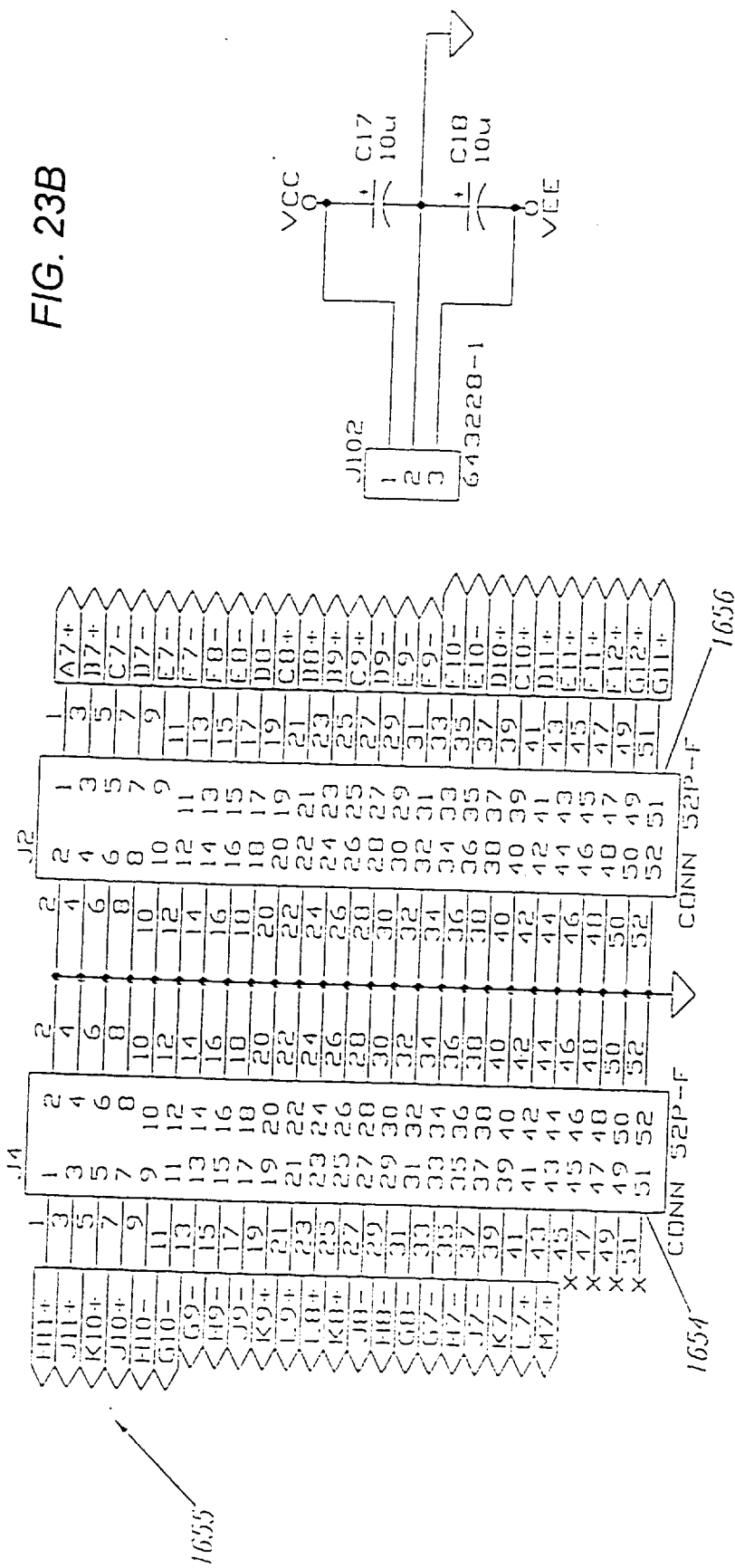
Figures 1, 24A:
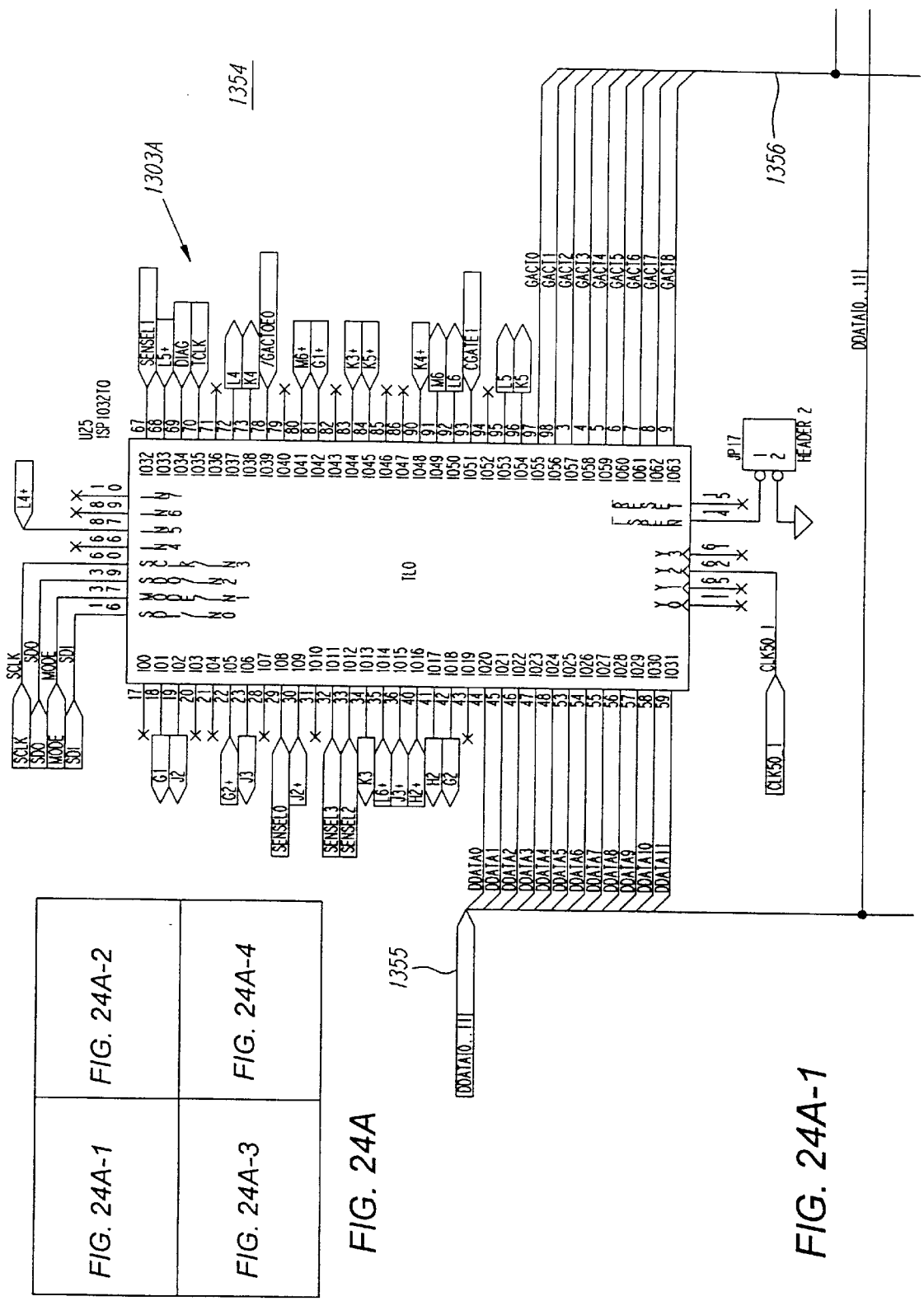
FIG. 24A and 24B are a layout arrangement plan for FIGS. 24A-1 to 4 and 24B-1 to 4 respectively.
Figures 2, 24A:
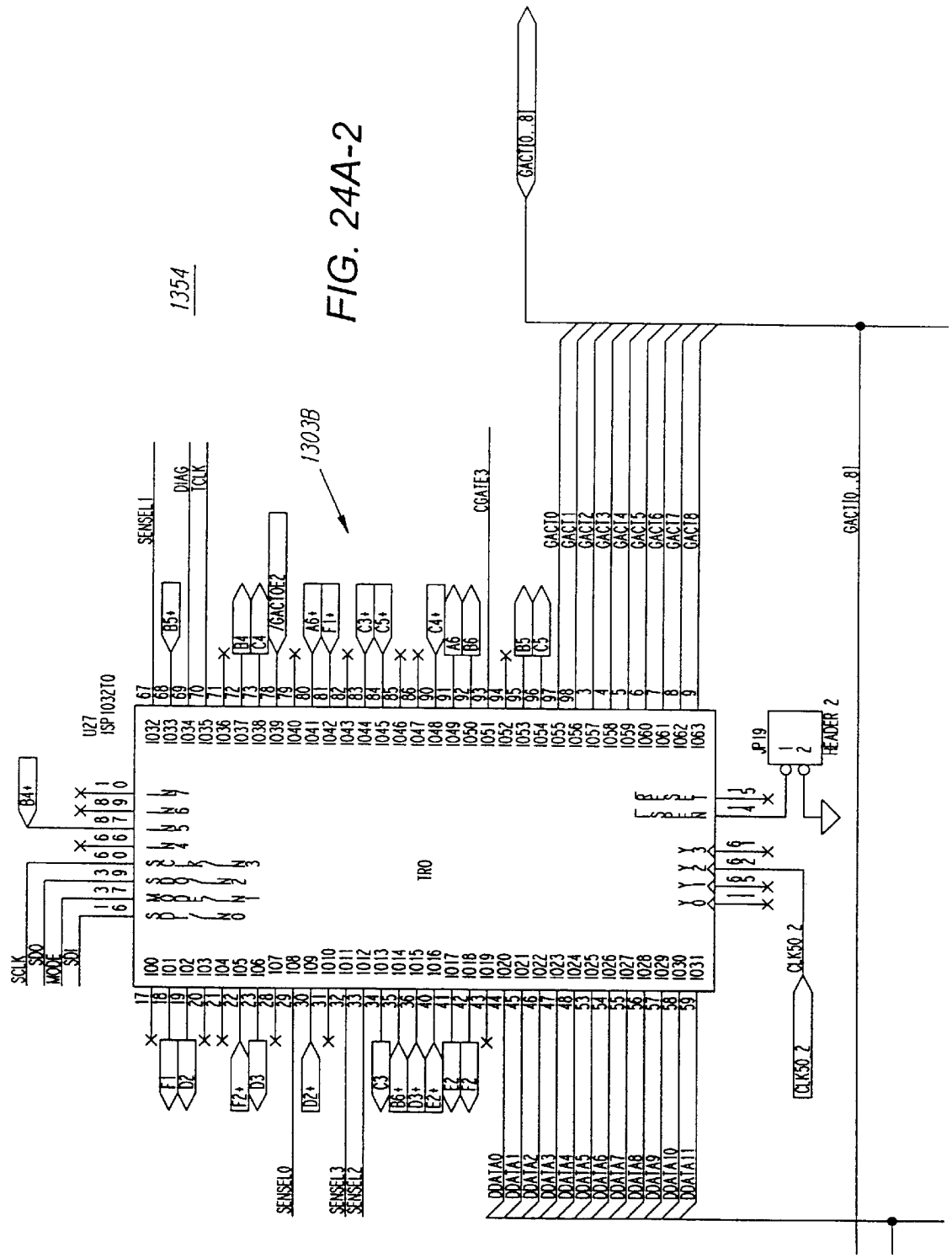
Figure 24A:
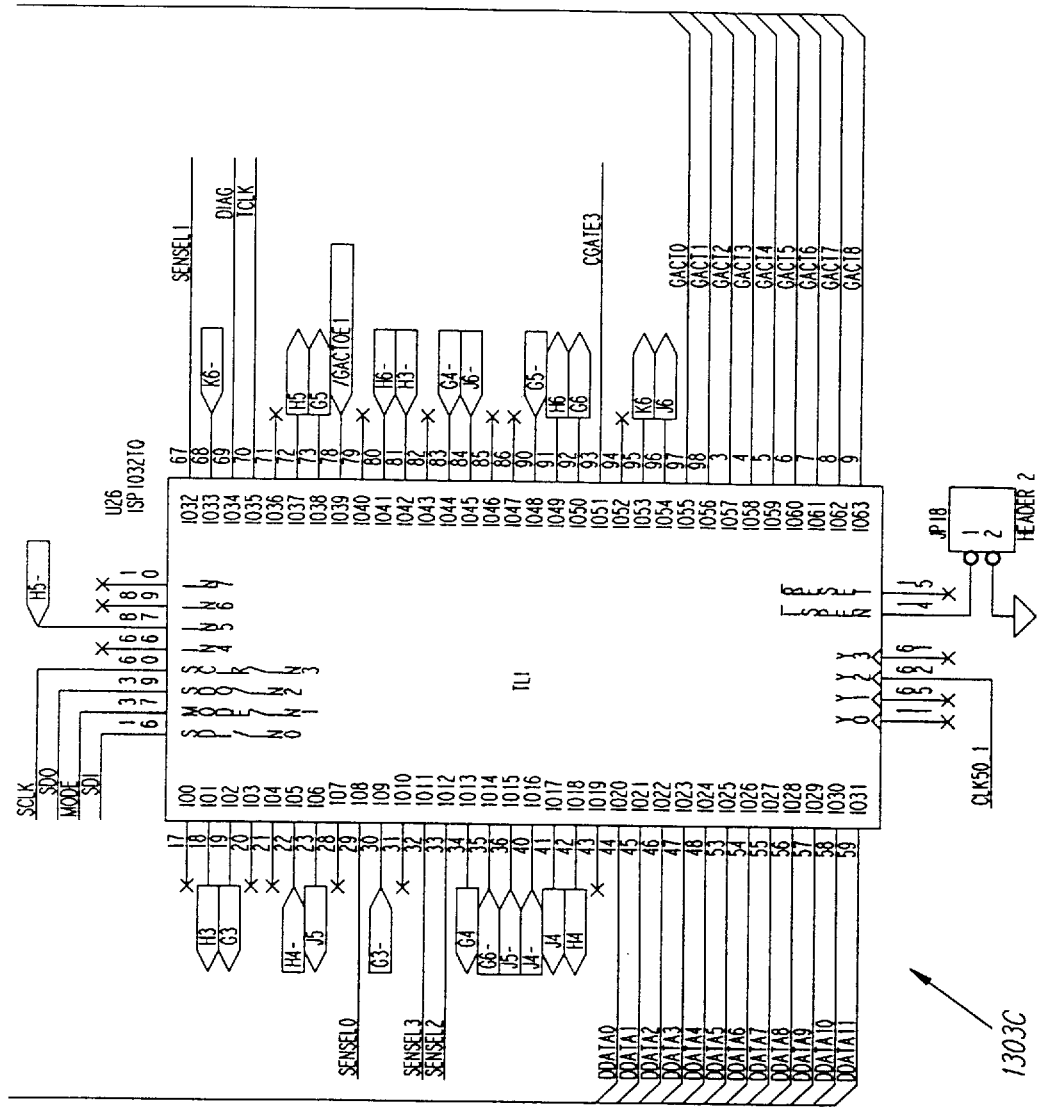
Figure 3:
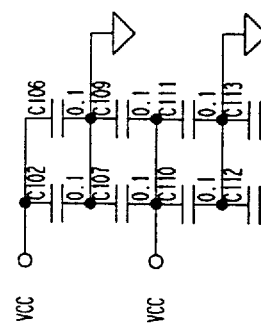
Figures 4, 24A:
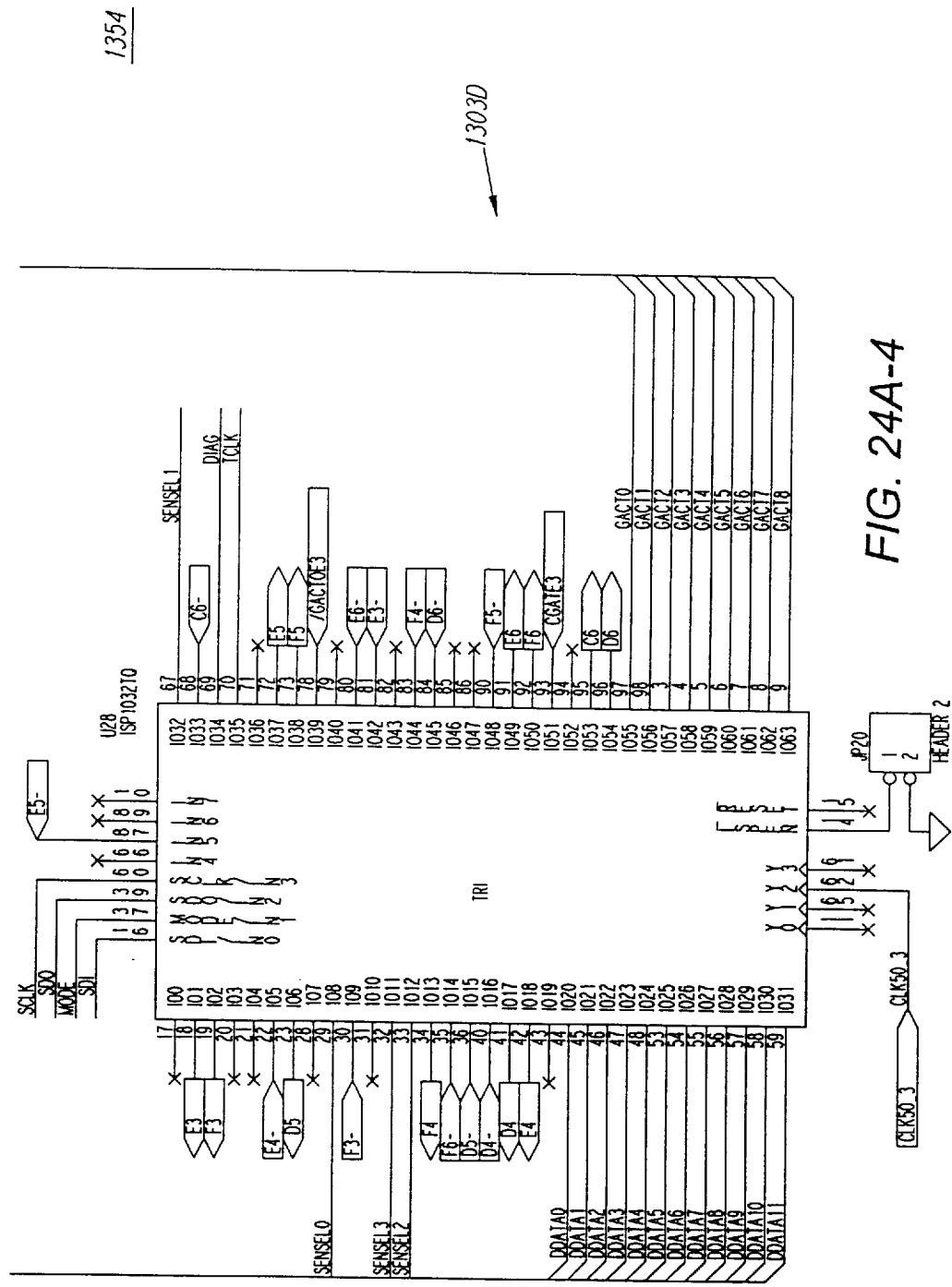
Figures 2, 24B:
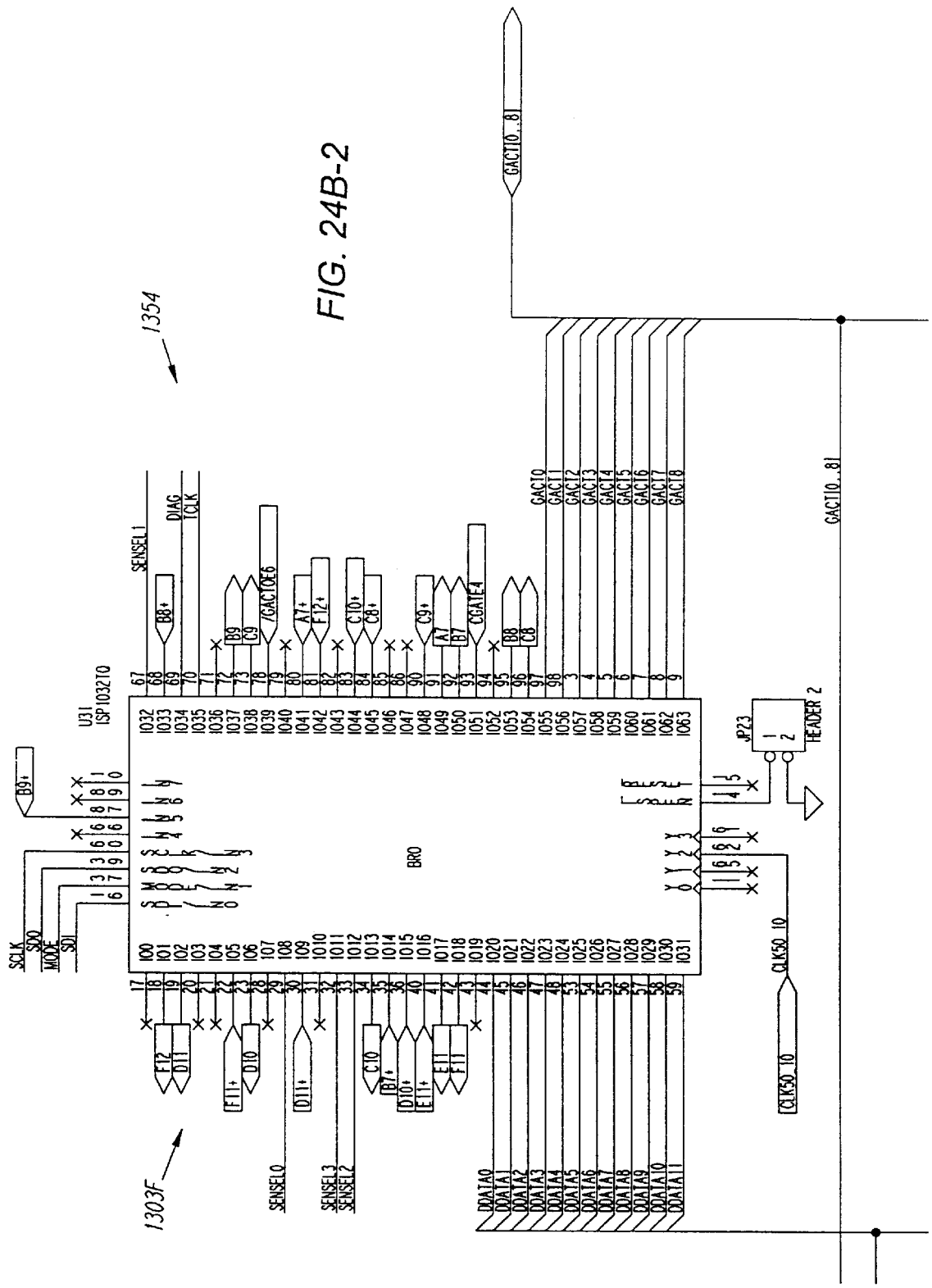
Figures 3, 24B:
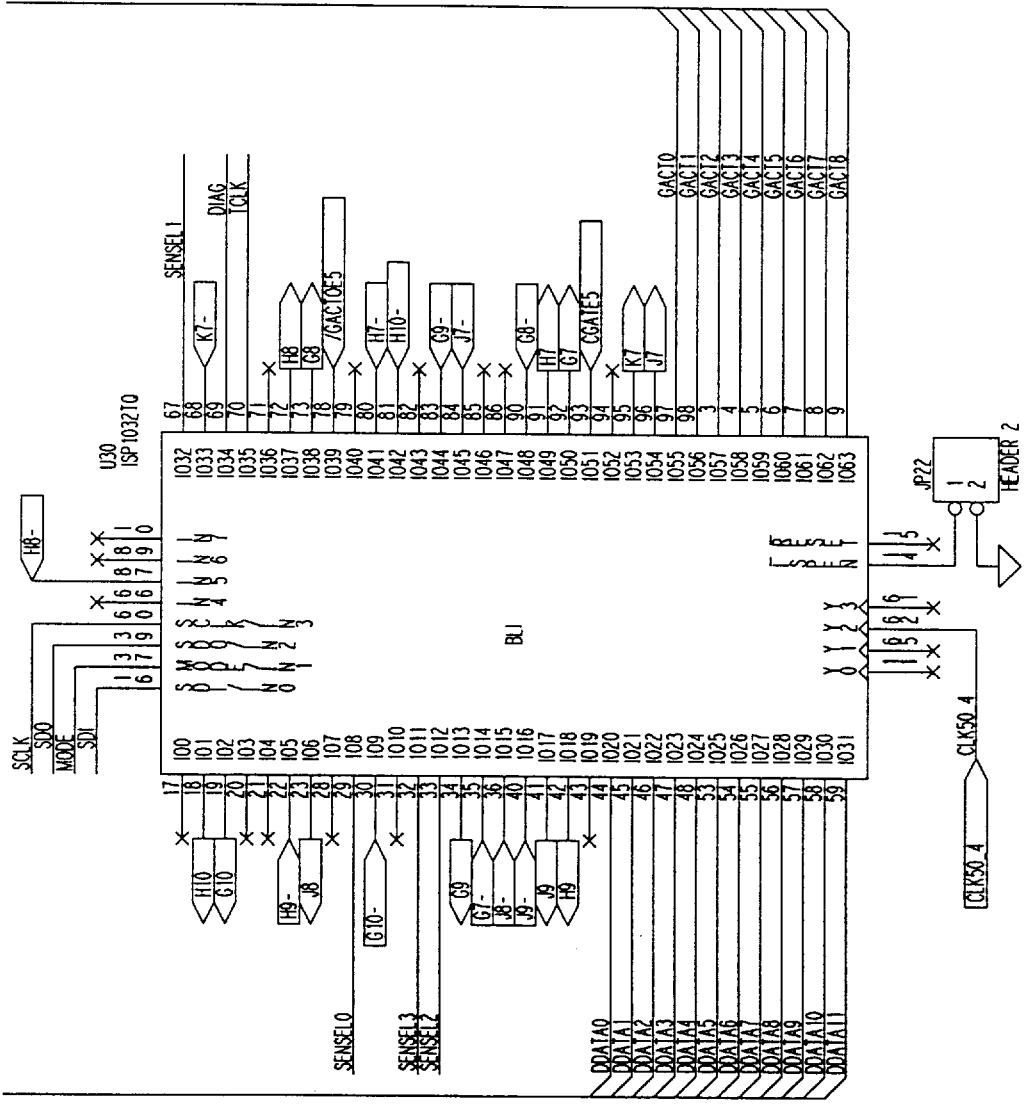
Figures 4, 24B:
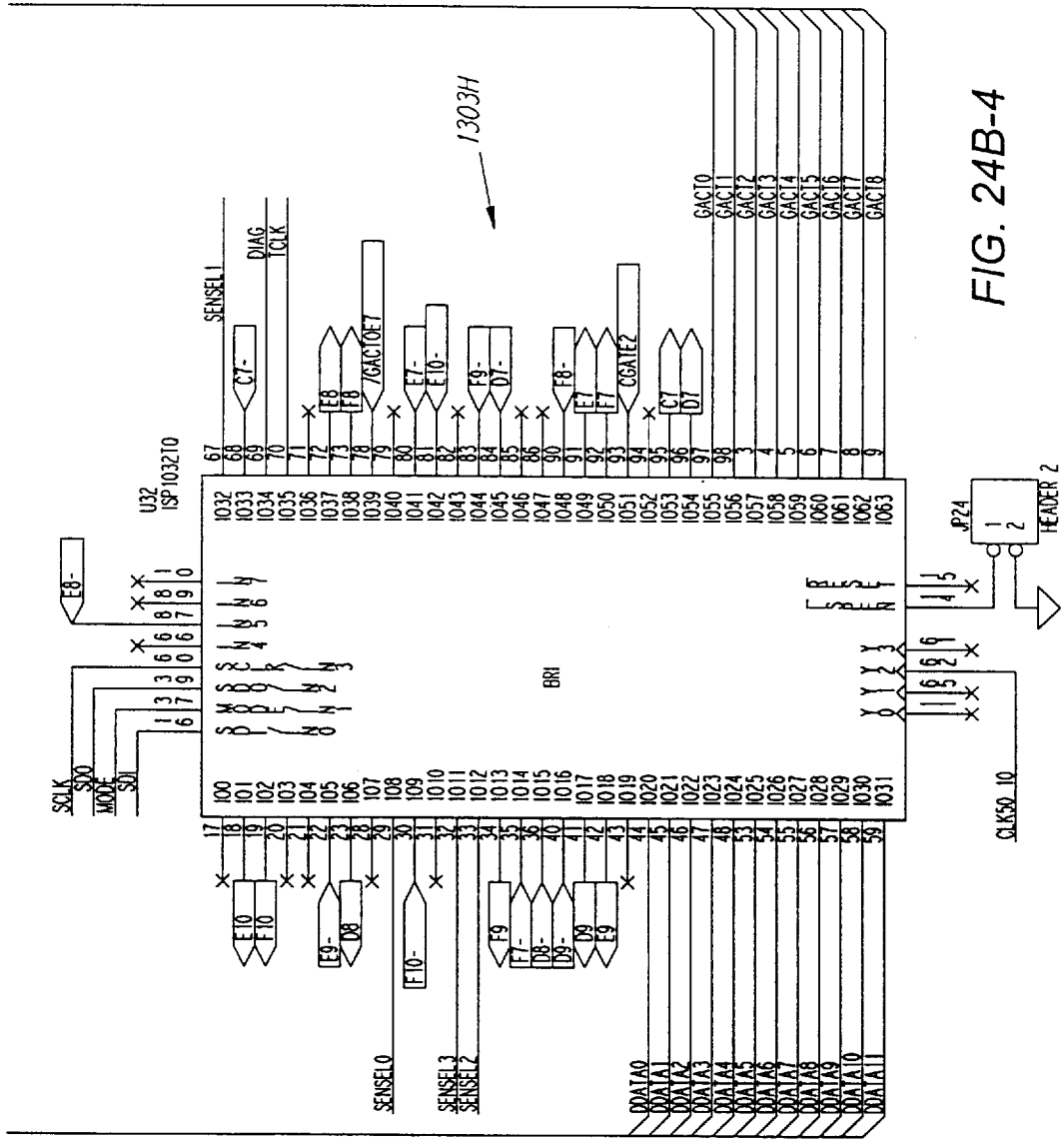

Referring to FIGS. 23A–B, four connectors 1650, 1652, 1654, and 1656 form the sensor connections 1655 between the signal conditioner 810 and the RTE octant counters 1354. After signal conditioning, signals from each of the 96 PMT detector elements 1339 connects the RTE octant counters 1354 through one of 96 electrical connections on the four connectors 1650, 1652, 1654, and 1656.

FIGS. 24A-1 to 4 and 24B-1 to 4 are diagrams of the preferred octant counters 1354. Eight such octant counters 1354 are used in the real-time eye. Each octant counter 1354 preferably comprises an ISP1032TQ lattice IC chip. Octant counter 1303A processes the inputs from the photocathode elements 1339 which is associated with the TLO octant. Similarly, octant counter 1303B processes the inputs for the TRO octant, octant counter 1303C for the TLI octant, octant counter 1303D for the TRI octant, octant counter 1303E for the BLO octant, octant counter 1303F for the BRO octant, octant counter 1303G for the BLI octant, and octant counter 1303H for the BRI octant. The preferred software modules for octant counters 1354 are included in Appendix A.

Each octant counter 1354 contains data input connections for each of the 12 PMT photo-cathode elements 1339 that is preferably associated with each octant. Upon detection of light photons by a PMT photo-cathode element 1339, an electrical signal is sent to its corresponding octant counter 1354. For the x-ray pencil beam which passes through a single collimator aperture, each of the eight octant counters 1354 produces a 9-bit value which contains the intensity data from all 12 of each octant's associated PMT photo-cathode elements 1339.

Figure 25:
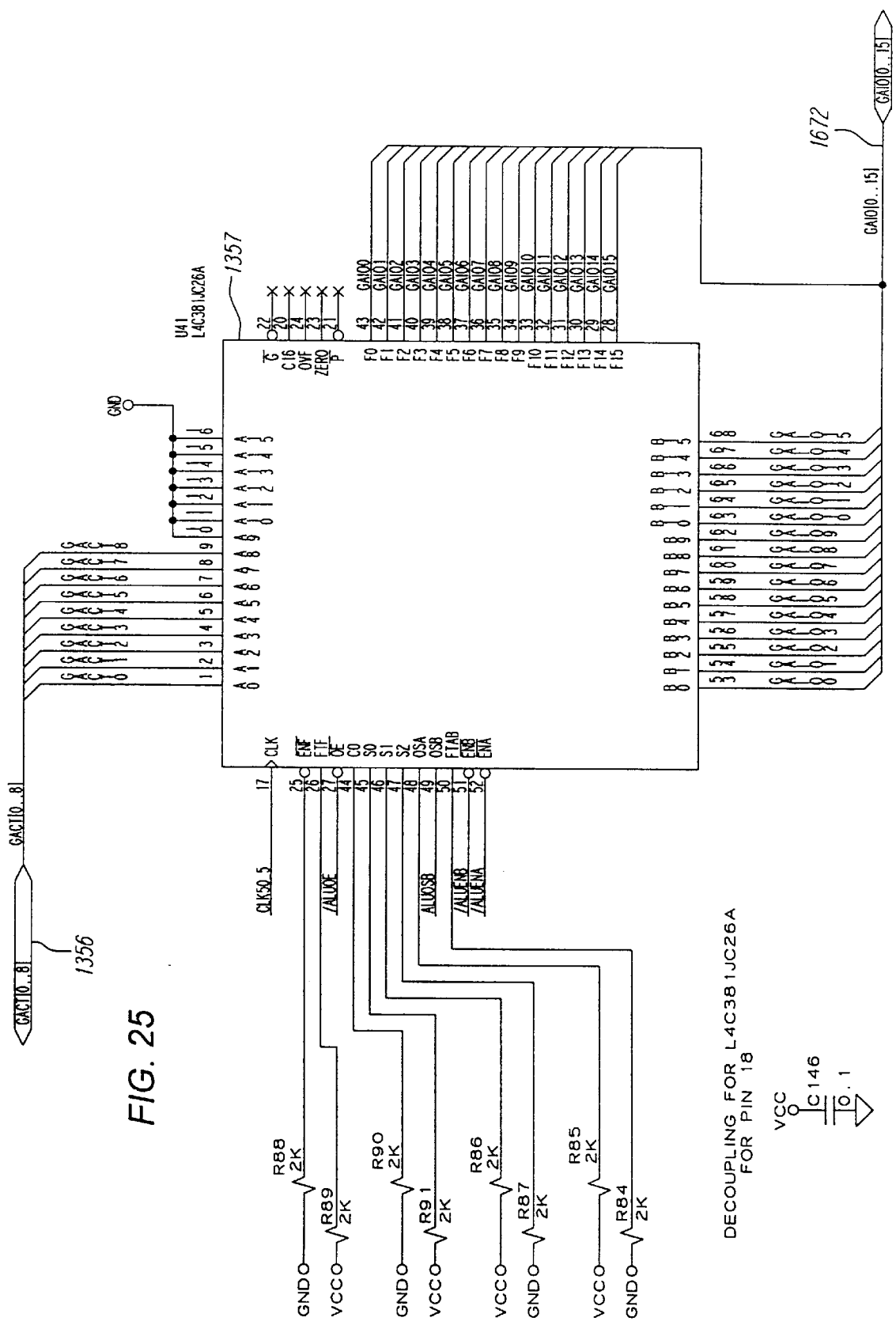
FIG. 25 is a schematic of a preferred gain & alignment ALU.

FIG. 25 diagrams the frame-summation chip 1357, which is an arithmetic logic unit ("ALU") and is preferably a L4C381JC26A IC chip available from Logic Devices, Inc. The 9 bit output from each octant counter 1354 is input to the frame-summation chip 1357 through connection 1356. The frame-summation chip 1357 processes eight numbers for each collimator aperture. For each succeeding frame, the frame-summation chip 1357 sums the corresponding values for the same octant for the same aperture from the previous frames. In the preferred embodiment, the octant values for 100–120 frames are added together to construct the data used for x-ray beam alignment.

Figure 26:
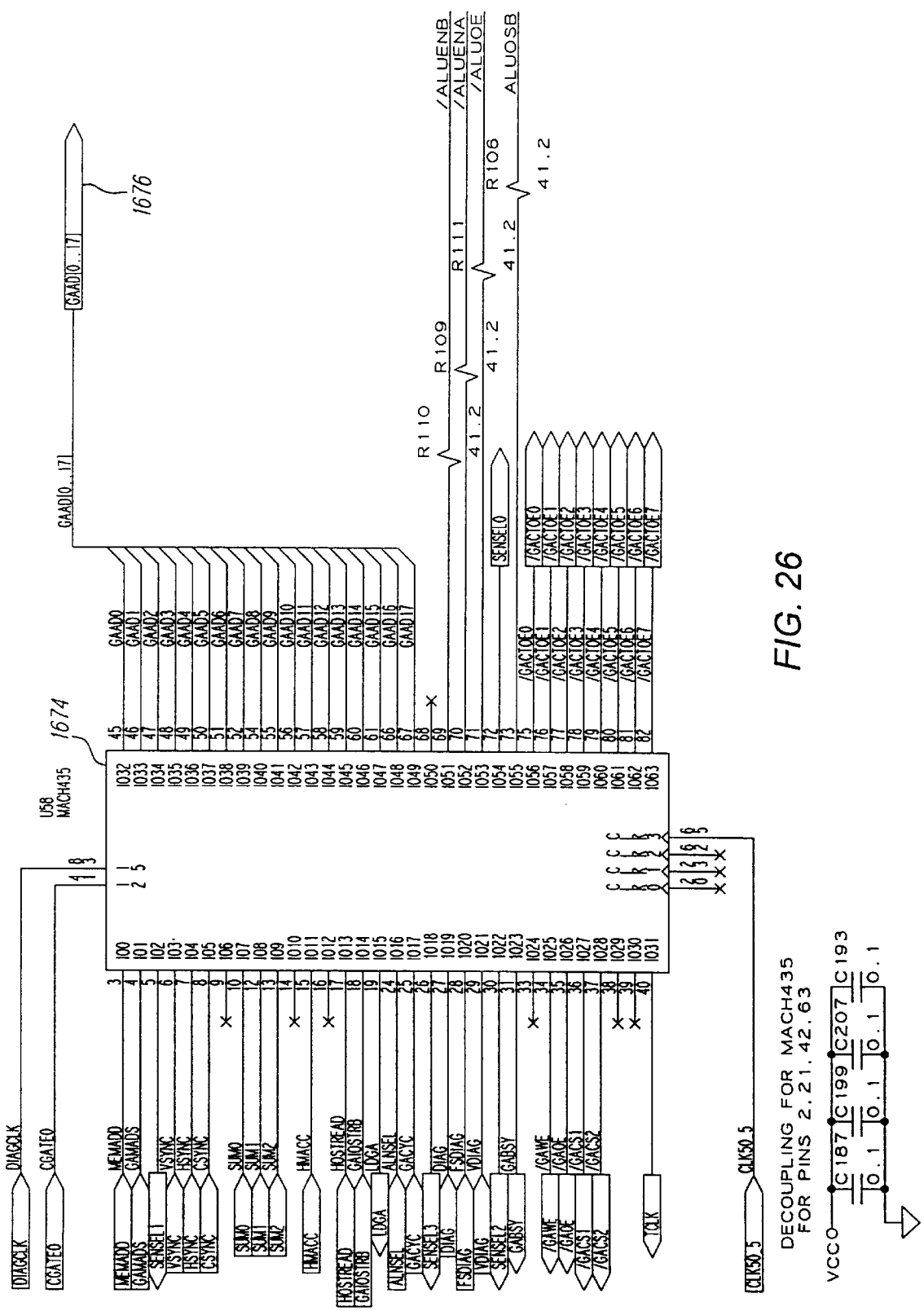
FIG. 26 is a schematic of a preferred gain & alignment engine.
Figures 27, 27A:
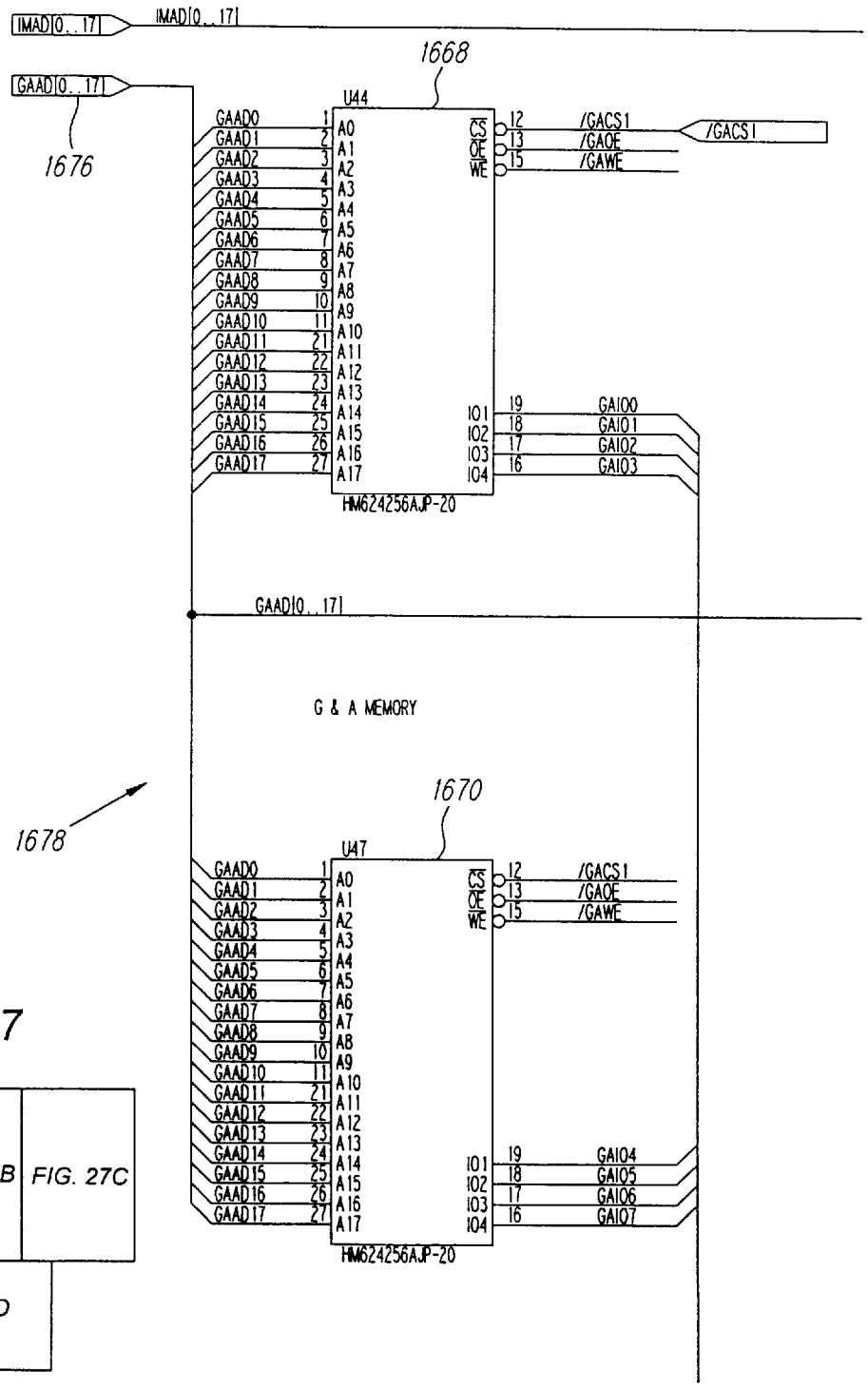
FIG. 27 is a layout arrangement plan for FIGS. 27A–D.
FIGS. 27A–D are schematics of the preferred memory for the preferred image reconstruction engine and gain & alignment circuitry.
Figure 27B:
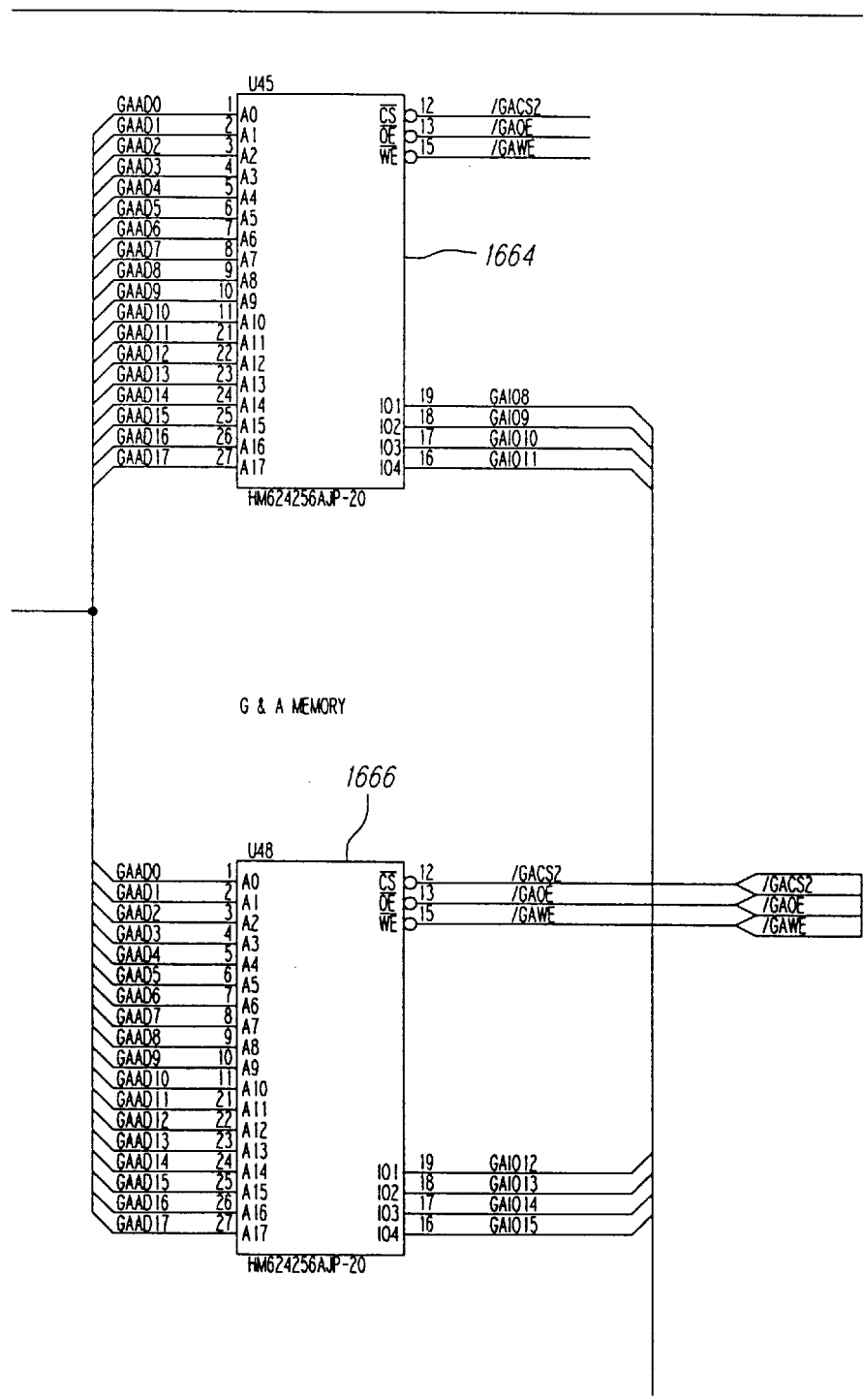
Figure 27C:
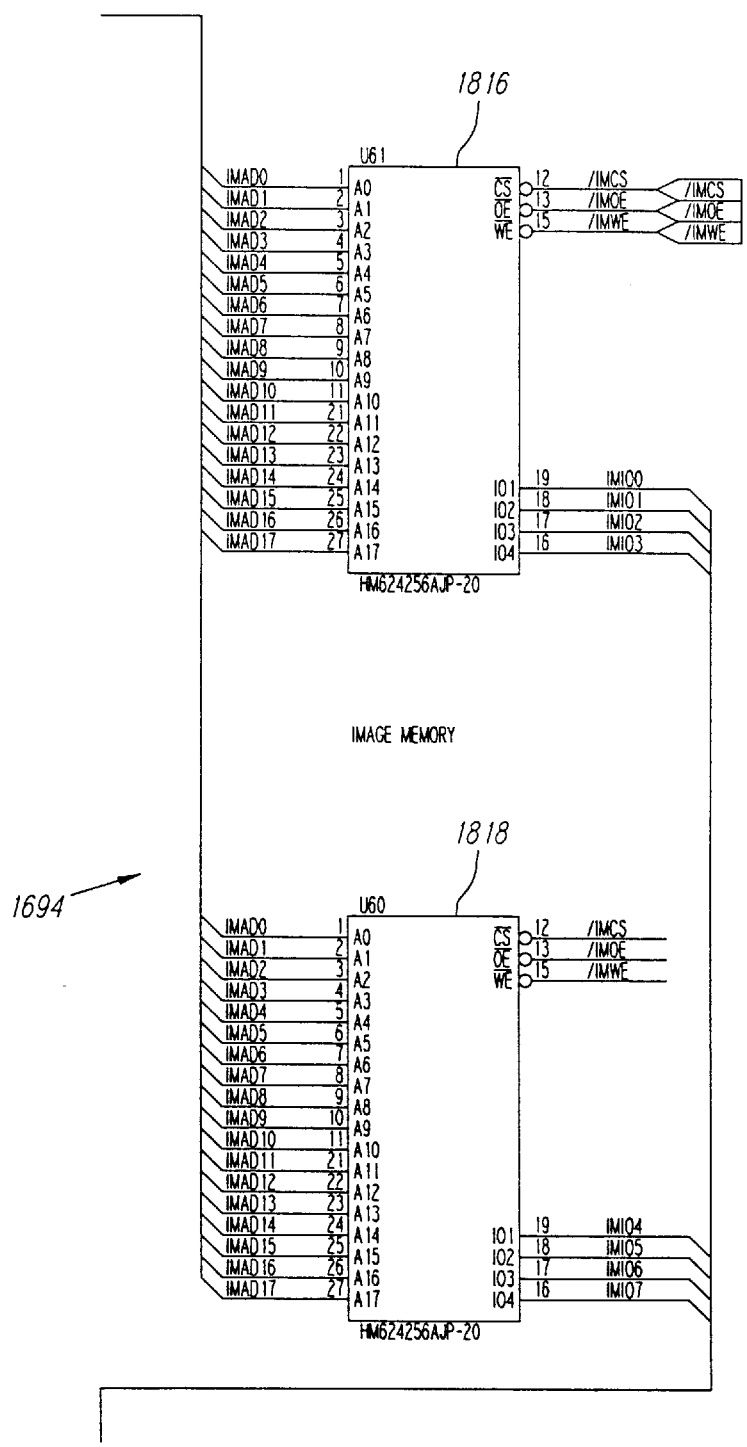
Figure 27D:
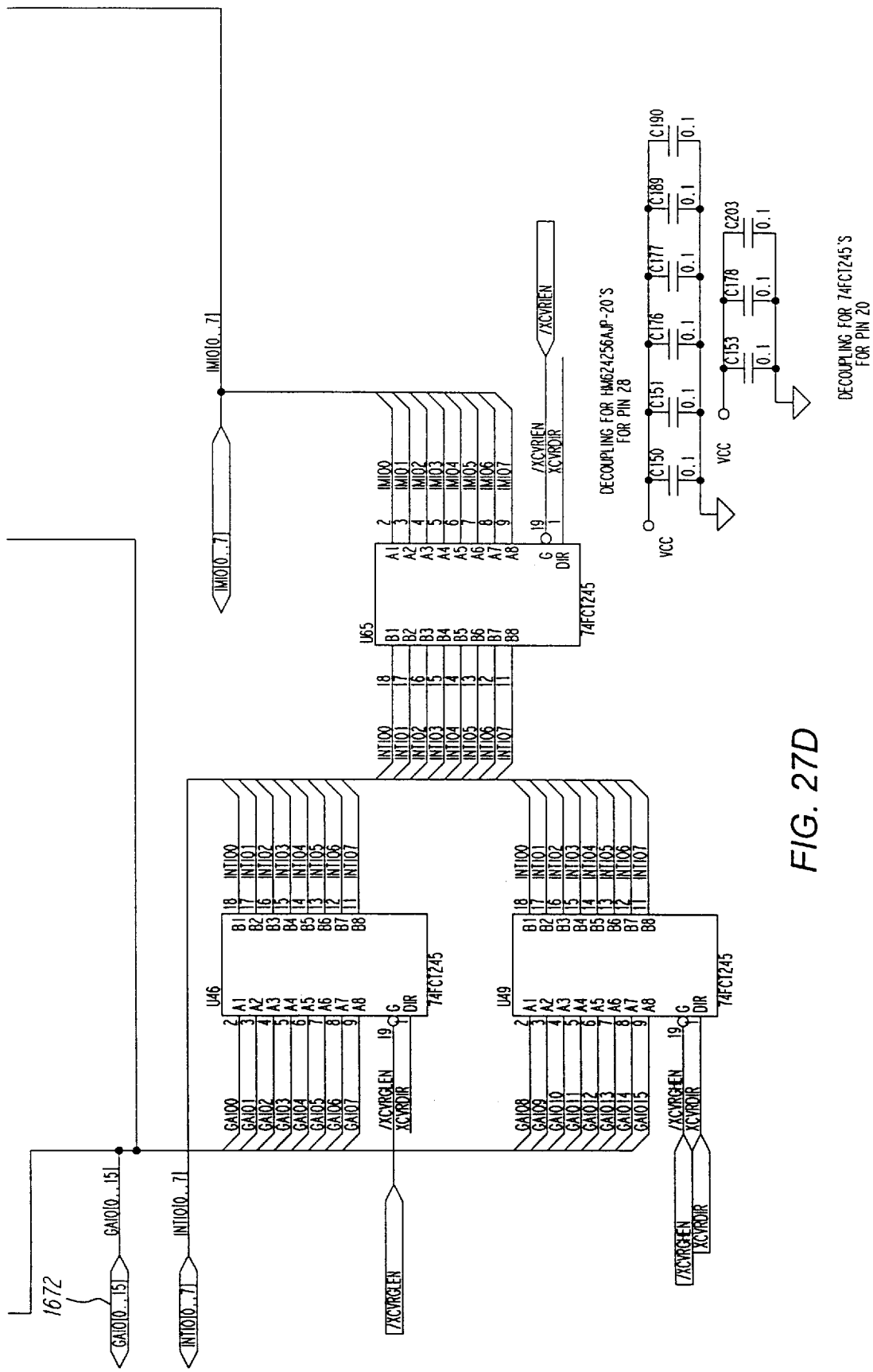

FIG. 26 diagrams the gain & alignment engine 1674, which is preferably a MACH435 IC chip available from AMD Corp. The gain & alignment engine 1674 determines the items of beam alignment data which is to be processed and manner of processing intended for that item of data. Additionally, the gain & alignment engine 1674 controls the timing of the components within the beam alignment extractor 816. The preferred software modules for the 20 gain & alignment engine 1674 are included in Appendix A.

FIGS. 27A–D is a diagram showing the gain & alignment memory chips 1678 which is comprised of four 1-Mbyte SRAM memory chips 1664, 1666, 1668, and 1670, each available under the model number MM624256AJP-20 from Hitachi Corporation. For each frame, eight values are collected for each collimator aperture. These values are stored in the gain & alignment memory 1678 after being processed through the frame-summation chip 1357. After 100–120 frames, the control computer will preferably access and process the data which is stored in the gain & alignment memory 1678 to correct the alignment of the x-ray beam.

While embodiments, applications and advantages of the invention have been shown and described with sufficient clarity to enable one skilled in the art to make and use the invention, it would be equally apparent to those skilled in the art that many more embodiments, applications and advantages are possible without deviating from the inventive concepts disclosed and described herein. The invention therefore should only be restricted in accordance with the spirit of the claims appended hereto and is not to be restricted by the preferred embodiments, specification or drawings.

221/228
PATENT

APPENDIX A

TABLE OF CONTENTS FOR SOFTWARE MODULES

| Programmable Logic Device | Section |
|---|---|
| Data Acquisition Control Chip 1638 (Fig. 22B) | 1 |
| Timing Control Chip 1640 (Fig. 22D) | 2 |
| Host Memory Control Chip 1642 (Fig. 22C) | 3 |
| Octant Counters 1354 (Figs. 24A & 24B) | 4 |
| Gain & Alignment Engine 1742 (Fig. 19) | 5 |

221/228
PATENT

EXHIBIT 1

221/228
PATENT

```
module rteda title 'RTE Data Acquisition Mode MACH (RTEDA)
       Ver. 0; 8/10/94'
       R1U56R0 device 'MACH435A';

" On-board registers in this device:

" Command Address 33

" bit 0      SNGFRA   RW
" bit 1      GACYC    RW
" bit 2      DACCYC   RW

" ControlStatus Address 34

" bit 0      ALNSEL   RW
" bit 1      BMACC    RW
" bit 2      DIAG     RW
" bit 3      FSDIAG   RW
" bit 4      VDIAG    RW
" bit 5      NVMSEL   RW
" bit 8      IMBSY    R
" bit 9      GABSY    R
" bit 10     SERBSY   R
" bit 11     NVMDOUT  R " Sum Address 35
" bit 0      SUM0     RW
" bit 1      SUM1     RW
" bit 2      SUM2     RW " Test Address 40 (uses DOR)

" bit 0      TEST0    RW
" bit 1      TEST1    RW
" bit 2      TEST2    RW
" bit 3      TEST3    RW
" bit 4      TEST4    RW
" bit 5      TEST5    RW
" bit 6      TEST6    RW
" bit 7      TEST7    RW
" bit 8      TEST8    RW
" bit 9      TEST9    RW
" bit 10     TEST10   RW
" bit 11     TEST11   RW
" bit 12     TEST12   RW
" bit 13     TEST13   RW
" bit 14     TEST14   RW
" bit 15     TEST15   RW "inputs
      CLK50 pin 20;
      RXD0,RXD1,RXD2,RXD3,RXD4,RXD5,RXD6,RXD7 pin 5,6,7,8,9,10,12,13;
      RXC0,RXC1,RXC2,RXC3 pin 33,41,3,4;
      !RXCSTRB pin 62;
      !RXDSTRB pin 65;
      RXCRST,RXDRST pin 67,68;
      IMBSY, GABSY, NVBSY pin 19,24,25;
      NVMDOUT pin 26;
```

52

```
        !OFIFEF0, !OFIFEF1, !OFIFEF   .n 38,39,40;
        OFIFSC0 pin 17;
        OFIFS01 pin 31;
        OFIFS02 pin 18;
        CLK12PE, CLK25PE pin 14, 15;
        LDIM, LDGA, LDENVM, LDLNVM pin 30,33,27,28;
        VSYNC pin 16;

"outputs
        TXC0,TXC1,TXC2,TXC3 pin 46,47,48,49 istype 'reg_D,buffer';
        TXSTRB pin 45 istype 'reg_D,buffer';
        SNGFRA,ALNSEL pin 56, 59, istype 'reg_D,buffer';
        NVMSEL pin 34 istype 'reg_D,buffer';
        EMACC,GACYC,DACCYC pin 51, 57, 58 istype 'reg_D,buffer';
        SUM0,SUM1,SUM2 pin 60, 61, 66 istype 'reg_D,buffer';
        DIAG,FSDIAG,VDIAG pin 52, 54, 55 istype 'reg_D,buffer';
        !OFIFOE0,!OFIFOE1,!OFIFOE2 pin 35, 36, 37 istype 'reg_D,buffer';
        !OFIFRE0,!OFIFRE1,!OFIFRE2 pin 80, 81, 82 istype 'reg_D,buffer';
        !OFIFMR pin 79 istype 'reg_D, buffer';

OUTCCK pin 29 istype 'buffer';
        INCCK pin 23;

"I/Os
        INTIO0,INTIO1,INTIO2,INTIO3 pin 69,70,71,72;
        INTIO4,INTIO5,INTIO6,INTIO7 pin 73,75,76,77;

"nodes
    "incoming address buffer
        ADD0, ADD1, ADD2, ADD3  node istype 'reg_D';
        ADD4, ADD5, ADD6, ADD7  node istype 'reg_D';
    "incoming command buffer
        BUC0,BUC1,BUC2,BUC3 node istype 'reg_D';
    "decode lines
        TESTPEND1, TESTPEND2, CTRLPEND, CMDPEND, SUMPEND node istype 'reg_D';
    "DOR
        DOR0, DOR1, DOR2, DOR3  node istype 'reg_D';
        DOR4, DOR5, DOR6, DOR7  node istype 'reg_D';
        DOR8, DOR9, DOR10,DOR11 node istype 'reg_D';
        DOR12,DOR13,DOR14,DOR15 node istype 'reg_D';
        LDDOR,LDCS,LDCMD,LDSUM  node istype 'reg_D';
        DORRDY node  istype 'reg_D,buffer';
        DOROE,OUTHI node  istype 'reg_D,buffer';
    "other
        READ node istype 'reg_D';
        RXS2,RXS1,RXS0 node istype 'reg_D';
        TXS2,TXS1,TXS0 node istype 'reg_D';
        LINCT2..LINCT0 node istype 'reg_T';
        CGA1..CGA0 node istype 'reg_D';
        DLDGA node istype 'reg_D';
        DVSYNC node istype 'reg_D';
        FLGSVLD node istype 'reg_D,buffer';
        SFRAME node istype 'reg_T,buffer';
        DELEF2 node istype 'reg_D,buffer';

AMDMACH PROPERTY 'GROUP B DOR0 DOR1 DOR2 DOR6 DOR7';
AMDMACH PROPERTY 'GROUP C DOR3 DOR4 DOR5 DOR8 DOR9';
AMDMACH PROPERTY 'GROUP F DOR10 DOR11 DOR12';
AMDMACH PROPERTY 'GROUP G DOR13';
AMDMACH PROPERTY 'GROUP H DOR14';
```

221/228
PATENT

```
AMDMACH PROPERTY 'GROUP E DOR15';

"constants
        H,L,X,C,Z = 1,0,.X.,.C.,.Z.;
        INTIO = [INTIO7..INTIO0];
        RXD   = [RXD7..RXD0];
        RXC   = [RXC3..RXC0];
        TXC   = [TXC3..TXC0];
        ADD   = [ADD7..ADD0];
        BUC   = [BUC3..BUC0];
        DORL  = [DOR7..DOR0];
        DORH  = [DOR15..DOR8];
        SUM_R = [SUM2..SUM0];
        SUM_8 = [0,0,0,0,0,SUM2..SUM0];
        CMD_R = [DACCYC,GACYC,SNGFRA];
        CMD_8 = [0,0,0,0,0,DACCYC,GACYC,SNGFRA];
        CTRL_R = [NVMSEL,VDIAG,FSDIAG,DIAG,EMACC,ALNSEL];
        CTRL_8 = [0,0,NVMSEL,VDIAG,FSDIAG,DIAG,EMACC,ALNSEL];
        MOD_8  = [0,0,0,0,0,0,0,1];
        STAT_8 = [0,0,0,0,NVHDOUT,NVBSY,GABSY,IHBSY];
        LS3BS  = [RXD2..RXD0];
        LS6BS  = [RXD5..RXD0];
        RX_STATE = [RXS2..RXS0];
        TX_STATE = [TXS2..TXS0];
        LINCT  = [LINCT2..LINCT0];
        CGA    = [CGA1..CGA0];

Declarations

WAIT_FOR_CMD = [0,0,0]; " 0
        WAIT_FOR_ADD = [0,0,1]; " 1
        WAIT_FOR_DB0 = [0,1,1]; " 3
        WAIT_FOR_DB1 = [1,1,1]; " 7
        LOAD_DOR     = [0,1,0]; " 2
        UNUSED_1     = [1,0,0]; " 4
        UNUSED_2     = [1,0,1]; " 5
        UNUSED_3     = [1,1,0]; " 6 equations

" ****************** DATA OUT REGISTER (DOR) HANDLING *************

DORH.clk  = CLK50;
        DORL.clk  = CLK50;
        LDDOR.clk = CLK50;
"       LDMOD.clk = CLK50;
        LDCS.clk  = CLK50;
        LDCMD.clk = CLK50;
        LDSUM.clk = CLK50;
        DORRDY.clk = CLK50;
        OUTHI.clk = CLK50;
        DOROE.clk = CLK50;
        CGA.clk   = CLK50;

" Data for the DOR is from an Image or GA memory read (managed by RTEHM),
" or an NV memory read, managed by RTETIM.

" ++++++ Image Memory Reads
" One byte transferred. HOSTREAD true. IMIOSTRB and LDIM are interlocked.
" This MACHs cycle is complete when byte is strobed into DOR by LDIM
```

54

```
"
" CLK50     | | | | | | | | | | | | | | |
" XCVRIEN         ---------------------
" INTIOEN                     -
" INIOSTRB            ----------------------
" INTIO     IIIIIIIIIIIIIIIIIIIIIIIII-IIIIVVVVVVVIIIIIIIII
" LDIH                          -___----
"                                  ^
"                       INTIO data to DOR (RTEDA MACH)
" ++++++ GA Memory Reads
" Two bytes transferred. HOSTREAD true. GAIOSTRB and LDGA are interlocked.
" This MACHs cycle is complete when bytes are strobed into DOR by LDGA
"
" CLK50     | | | -| | | | | | | | | | |
" XCVRGLEN        -- -------
" XCVRGHEN          -_____--------_____
" INTIOEN          -_____
" GAIOSTRB        -- -------------------
" INTIO     ZZZZZZZZZZZZZLL -LLLLLLZZZZHHHHHHHHZZZZZZZZZZZZZ
" CGA0                    -_____--------_____
" CGA1                                -------_____
" LDGA              -_____
" DLDGA                -_____
"                   ^                     ^
"            L then H byte INTIO data to DOR (RTEDA MACH)
"            (timed from LDGA goes high).
"

DLDGA.clk = CLK50;
       DLDGA := LDGA;

CGA0 := LDGA & DLDGA & !CGA1;
       CGA1 := CGA0;
       DORH := INTIO & LDGA & CGA0
             # INTIO & LDHNVH
             # STAT_8 & LDCS
             # RXD & TESTPEND2&RXDRST
     # DORH & !(LDGA & CGA0 # LDHNVH # LDCS # LDIH # LDCHD # LDSCH # TESTPEND2&RXDRST);

DORL := INTIO & LDGA & !DLDGA
             # INTIO & LDLNVH
             # INTIO & LDIH
             # CTRL_8 & LDCS
             # CMD_8 & LDCMD
             # SCH_8 & LDSCH
             # MOD_8 & LDMOD
             # DORL & !(LDGA & !DLDGA # LDLNVH # LDIH # LDCS
                        # LDCMD # LDSCH);

INTIO = DORH & OUTHI
             # DORL & !OUTHI;

INTIO.oe = DOROE;

" *********************** RX TAXI STATE MACHINE ***************************

" This MACH decodes Taxi input commands
"    1 = WRITE REGISTER
"    2 = READ REGISTER
```

221/228
PATENT

```
" for addresses
"     32 = ModuleID (Read only)
"     33 = Command (Read/Write)
"     34 = ControlStatus (Read/Write)
"     35 = Sum (Read/Write)
"     40 = Test (DOR) (Read/Write)

" Use the edge of the strobe to clock the Taxi command or data
" into a local buffer " The command data is always strobed into the BCC buffer. When it is a
" command appropriate to us (READ or WRITE REGISTER commands) it
" will kick off the state machine. Subsequent commands may overwrite BCC
" even if the state machine has not finished, however they will be
" timing commands, not read or writes, and therefore ignored here.
"
" The data is strobed into the address buffer if the state machine
" is waiting for an address.
" The data is strobed into the CTRL, CMD and SUM registers if the
" state machine is waiting for data for that register.

ADD.clk = RXDSTRB;
       BCC.clk = RXCSTRB;

ADD  := (RXD & (RX_STATE == WAIT_FOR_ADD))
             # (ADD & (RX_STATE != WAIT_FOR_ADD));
       BCC  := RXC;

" Use the strobe resets to flag when command or data is received

" The RX state machine decodes the Taxi command and data inputs
" It controls the READ, SUMPEND, CMDPEND, CTRLPEND, LDCS, LDCMS
" LDSUM and LDMOD outputs.

RX_STATE.clk = CLK50;
       READ.clk     = CLK50;
       SUMPEND.clk  = CLK50;
       CMDPEND.clk  = CLK50;
       CTRLPEND.clk = CLK50;
       TESTPEND1.clk = CLK50;
       TESTPEND2.clk = CLK50;

CMD_R.clk  = RXDSTRB;
       SUM_R.clk  = RXDSTRB;
       CTRL_R.clk = RXDSTRB & CTRLPEND;
"      CTRL_R.clk = INCCK;

OUTCCK = RXDSTRB & CTRLPEND;

SUM_R := LS3BS & SUMPEND
              # SUM_R & !SUMPEND;

CMD_R := LS3BS & CMDPEND
              # CMD_R & !CMDPEND;

CTRL_R := LS6BS;

State_diagram [RXS2,RXS1,RXS0]
```

56

```
state WAIT_FOR_CMD:
    if (RXCRST & (BUC == 1)) " Write reg
        then WAIT_FOR_ADD
            with READ := 0;
                CTRLPEND := 0;
                CMDPEND := 0;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS  := 0;
            endwith;
    else if (RXCRST & (BUC == 2)) " Read reg
        then WAIT_FOR_ADD
            with READ := 1;
                CTRLPEND := 0;
                CMDPEND := 0;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS  := 0;
            endwith;
    else WAIT_FOR_CMD
        with READ := 0;
            CTRLPEND := 0;
            CMDPEND := 0;
            SUMPEND := 0;
            TESTPEND1 := 0;
            TESTPEND2 := 0;
            LDMOD := 0;
            LDDOR := 0;
            LDCMD := 0;
            LDSUM := 0;
            LDCS  := 0;
        endwith;
state WAIT_FOR_ADD:
    if (RXDRST & (ADD == 33) & !READ) " Command reg write
        then WAIT_FOR_DB0
            with READ := 0;
                CTRLPEND := 0;
                CMDPEND := 1;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS  := 0;
            endwith;
    else if (RXDRST & (ADD == 34) & !READ) " Control reg write
        then WAIT_FOR_DB0
```

57

```
            with READ := 0;
                 CTRLPEND := 1;
                 CHDPEND := 0;
                 SUMPEND := 0;
                 TESTPEND1 := 0;
                 TESTPEND2 := 0;
                 LDMOD := 0;
                 LDDOR := 0;
                 LDCHD := 0;
                 LDSUM := 0;
                 LDCS  := 0;
            endwith;
        else if (RXDRST & (ADD == 35) & !READ) " Sum reg write
            then WAIT_FOR_DBO
            with READ := 0;
                 CTRLPEND := 0;
                 CHDPEND := 0;
                 SUMPEND := 1;
                 TESTPEND1 := 0;
                 TESTPEND2 := 0;
                 LDMOD := 0;
                 LDDOR := 0;
                 LDCHD := 0;
                 LDSUM := 0;
                 LDCS  := 0;
            endwith;
        else if (RXDRST & (ADD == 40) & !READ) " Test reg write
            then WAIT_FOR_DBO
            with READ := 0;
                 CTRLPEND := 0;
                 CHDPEND := 0;
                 SUMPEND := 0;
                 TESTPEND1 := 1;
                 TESTPEND2 := 0;
                 LDMOD := 0;
                 LDDOR := 0;
                 LDCHD := 0;
                 LDSUM := 0;
                 LDCS  := 0;
            endwith;
        else if (RXDRST & (ADD == 32) & READ) " Modid read
            then LOAD_DOR
            with READ := 1;
                 CTRLPEND := 0;
                 CHDPEND := 0;
                 SUMPEND := 0;
                 TESTPEND1 := 0;
                 TESTPEND2 := 0;
                 LDMOD := 1;
                 LDDOR := 0;
                 LDCHD := 0;
                 LDSUM := 0;
                 LDCS  := 0;
            endwith;
        else if (RXDRST & (ADD == 40) & READ) " DOR read
            then LOAD_DOR
            with READ := 1;
                 CTRLPEND := 0;
                 CHDPEND := 0;
                 SUMPEND := 0;
```

58

```
                  TESTPEND1 :=
                  TESTPEND2 := 0;
                    LDMOD := 0;
                    LDDOR := 1;
                    LDCMD := 0;
                    LDSUM := 0;
                    LDCS  := 0;
              endwith;
        else if (RXDRST & (ADD == 33) & READ) " Cmd reg read
          then LOAD_DOR
              with READ := 1;
                   CTRLPEND := 0;
                   CMDPEND := 0;
                   SUMPEND := 0;
                   TESTPEND1 := 0;
                   TESTPEND2 := 0;
                    LDMOD := 0;
                    LDCMD := 1;
                    LDSUM := 0;
                    LDCS  := 0;
              endwith;
        else if (RXDRST & (ADD == 34) & READ) " Ctrl/stat reg read
          then LOAD_DOR
              with READ := 1;
                   CTRLPEND := 0;
                   CMDPEND := 0;
                   SUMPEND := 0;
                   TESTPEND1 := 0;
                   TESTPEND2 := 0;
                    LDMOD := 0;
                    LDDOR := 0;
                    LDCMD := 0;
                    LDSUM := 0;
                    LDCS  := 1;
              endwith;
        else if (RXDRST & (ADD == 35) & READ) " Sum reg read
          then LOAD_DOR
              with READ := 1;
                   CTRLPEND := 0;
                   CMDPEND := 0;
                   SUMPEND := 0;
                   TESTPEND1 := 0;
                   TESTPEND2 := 0;
                    LDMOD := 0;
                    LDDOR := 0;
                    LDCMD := 0;
                    LDSUM := 1;
                    LDCS  := 0;
              endwith;
        else if (RXDRST)   " Address not for us
          then goto WAIT_FOR_CMD
              with READ := 0;
                   CTRLPEND := 0;
                   CMDPEND := 0;
                   SUMPEND := 0;
                   TESTPEND1 := 0;
                   TESTPEND2 := 0;
                    LDMOD := 0;
                    LDDOR := 0;
                    LDCMD := 0;
```

```
                    LDSUM := 0;
                    LDCS  := 0;
                endwith;
            else WAIT_FOR_ADD
                with READ := READ;
                    CTRLPEND := 0;
                    CMDPEND := 0;
                    SUMPEND := 0;
                    TESTPEND1 := 0;
                    TESTPEND2 := 0;
                    LDMOD := 0;
                    LDDOR := 0;
                    LDCMD := 0;
                    LDSUM := 0;
                    LDCS  := 0;
                endwith;
        state WAIT_FOR_DB0:
            if RXDRST & TESTPEND1
                then WAIT_FOR_DB1
                    with READ := 0;
                        CTRLPEND := 0;
                        CMDPEND := 0;
                        SUMPEND := 0;
                        TESTPEND1 := 0;
                        TESTPEND2 := 1;
                        LDMOD := 0;
                        LDDOR := 0;
                        LDCMD := 0;
                        LDSUM := 0;
                        LDCS  := 0;
                    endwith;
            else if RXDRST
                then WAIT_FOR_CMD
                    with READ := 0;
                        CTRLPEND := 0;
                        CMDPEND := 0;
                        SUMPEND := 0;
                        TESTPEND1 := 0;
                        TESTPEND2 := 0;
                        LDMOD := 0;
                        LDDOR := 0;
                        LDCMD := 0;
                        LDSUM := 0;
                        LDCS  := 0;
                    endwith;
            else WAIT_FOR_DB0
                with READ := 0;
                    CTRLPEND := CTRLPEND;
                    CMDPEND := CMDPEND;
                    SUMPEND := SUMPEND;
                    TESTPEND1 := TESTPEND1;
                    TESTPEND2 := TESTPEND2;
                    LDMOD := 0;
                    LDDOR := 0;
                    LDCMD := 0;
                    LDSUM := 0;
                    LDCS  := 0;
                endwith;
        state WAIT_FOR_DB1:
            if RXDRST
```

221/228
PATENT

```
                    then WAIT_FOR_CMD         ' Done
                        with READ := 0;
                            CTRLPEND := 0;
                            CMDPEND := 0;
                            SUMPEND := 0;
                            TESTPEND1 := 0;
                            TESTPEND2 := 0;
                            LDMOD := 0;
                            LDDOR := 0;
                            LDCMD := 0;
                            LDSUM := 0;
                            LDCS  := 0;
                        endwith;
                    else WAIT_FOR_DB1
                        with READ := 0;
                            CTRLPEND := 0;
                            CMDPEND := 0;
                            SUMPEND := 0;
                            TESTPEND1 := 0;
                            TESTPEND2 := 1;
                            LDMOD := 0;
                            LDDOR := 0;
                            LDCMD := 0;
                            LDSUM := 0;
                            LDCS  := 0;
                        endwith;
    state LOAD_DOR:
        goto WAIT_FOR_CMD
                with READ := 0;
                    CTRLPEND := 0;
                    CMDPEND := 0;
                    SUMPEND := 0;
                    TESTPEND1 := 0;
                    TESTPEND2 := 0;
                    LDMOD := 0;
                    LDDOR := 0;
                    LDCMD := 0;
                    LDSUM := 0;
                    LDCS  := 0;
                endwith;
    state UNUSED_1:
        goto WAIT_FOR_CMD
                with READ := 0;
                    CTRLPEND := 0;
                    CMDPEND := 0;
                    SUMPEND := 0;
                    TESTPEND1 := 0;
                    TESTPEND2 := 0;
                    LDMOD := 0;
                    LDDOR := 0;
                    LDCMD := 0;
                    LDSUM := 0;
                    LDCS  := 0;
                endwith;
    state UNUSED_2:
        goto WAIT_FOR_CMD
                with READ := 0;
                    CTRLPEND := 0;
                    CMDPEND := 0;
                    SUMPEND := 0;
```

```
                         TESTPEND1 := 0;
                         TESTPEND2 := 0;
"                          LDMOD := 0;
                           LDDOR := 0;
                           LDCMD := 0;
                           LDSUM := 0;
                           LDCS  := 0;
                    endwith;
    state UNUSED_3:
        goto WAIT_FOR_CMD
                    with READ := 0;
                         CTRLPEND := 0;
                         CMDPEND := 0;
                         SUMPEND := 0;
                         TESTPEND1 := 0;
                         TESTPEND2 := 0;
"                          LDMOD := 0;
                           LDDOR := 0;
                           LDCMD := 0;
                           LDSUM := 0;
                           LDCS  := 0;
                    endwith;
```

" ******************* TX TAXI STATE MACHINE ***********************

" The TX Taxi is controlled by a state machine. Transmissions occur
" if there is data to go in the DOR or the OFIFO. The DOR has priority.
" DORRDY flags data ready to go in the DOR, DORRDY is set when
" one of the strobes is detected and cleared by this state machine.

" OFIFO data is taken out 489 bytes from each of 3 lines in turn.
" When each byte is taken out, if the sync bit is high that indicates
" end of line. This is checked in TX state STR_DATA and causes a branch
" to state SEND_SL. In SEND_SL a START LINE message is sent and
" LINCT is incremented.
" The three LINCT lines indicate which is the currently active line.
" Everything is reset on the trailing edge of VSYNC, which indicates
" the start of an active frame. The reset includes a FIFO reset and
" LINCT reset. Also, VSYNC trailing edge sets the send start of frame
" bit and causes a START FRAME message to be sent.

"
" CLK12PH and CLK25PH are decoded to indicate the phase of the Taxi
" transmission (the Taxi is clocked by CLK12 which is identical to
" CLK12PH).
"
" The Taxi requires a data strobe and four command inputs, TXCSTRB
" and TXC3..TXC0. The strobe is decoded from the state and phase.

Declarations

WAIT_SEND  = [0,0,0];
        SET_READ   = [0,0,1];
        SEND_DB0   = [0,1,0];
        SEND_DB1   = [0,1,1];
        RD_FIFO    = [1,0,0];
        STR_DATA   = [1,0,1];
        SEND_SF    = [1,1,0];
        SEND_SL    = [1,1,1];

Equations

```
        TXC.clk = CLK50;
        TX_STATE.clk = CLK50;
        OFIFOE0.clk = CLK50;
        OFIFOE1.clk = CLK50;
        OFIFOE2.clk = CLK50;
        OFIFRE0.clk = CLK50;
        OFIFRE1.clk = CLK50;
        OFIFRE2.clk = CLK50;

DVSYNC.clk = CLK50;
    DVSYNC := VSYNC;

SFRAME.clk = CLK50;
    FLGSVLD.clk = CLK50;
    DELEF2.clk = CLK50;

"         |    |    |    |    |    |
" VSYNC  -------_____
" DVSYNC ------------_____
" OFIFMR _____-----_____
" FLGSVLD ------------_____----

OFIFMR.clk = CLK50;

OFIFMR := !VSYNC & DVSYNC;
    FLGSVLD := (!EMACC # EMACC&SNGFRA) & !(!VSYNC & DVSYNC) & !OFIFMR;
    DELEF2 := OFIFEF2;

" SFRAME causes a start frame message to be transmitted, used as
" VSYNC at the receiver
" The act of sending the message causes SFRAME to be reset
" Two of these messages are sent. The decoded conditions are
" 1:
" VSYNC AND the third OFIFO empty flag leading edge (ie the final line
" FIFO is emptied at the end of frame)
" 2:
" VSYNC going false causes a one-cycle OFIFO master reset. This
" sets SFRAME.

SFRAME.t = OFIFMR & !SFRAME
             # OFIFEF2 & !DELEF2 & VSYNC & !SFRAME
             # (TX_STATE == SEND_SF) & CLK25PH & CLK12PH & SFRAME;

" Line flags
" Data on a line is sent when the LINCT bit is set and the associated
" FIFO has data in it.

LINCT.clk = CLK50;

LINCT0.t = !LINCT0 & !VSYNC & DVSYNC            " Reset to 1 at EOF
         # LINCT0 & (TX_STATE == SEND_SL) & CLK25PH & CLK12PH
         # !LINCT0 & LINCT2 & (TX_STATE == SEND_SL) & CLK25PH & CLK12PH;
                                                " Change at EOL LINCT1.t = LINCT1 & !VSYNC & DVSYNC             " Reset at EOF
         # LINCT1 & (TX_STATE == SEND_SL) & CLK25PH & CLK12PH
         # !LINCT1 & LINCT0 & (TX_STATE == SEND_SL) & CLK25PH & CLK12PH;
```

63

```
LINCT2.t = LINCT2 & !VSYNC & DVSYNC              " Reset at EOF
         # LINCT2 & (TX_STATE == SEND_SL) & CLK25PH & CLK12PH
         # !LINCT2 & LINCT1 & (TX_STATE == SEND_SL) & CLK25PH & CLK12PH;

TXSTRB.clk = CLK50;

TXSTRB := ((TX_STATE==SET_READ)& !CLK25PH & !CLK12PH) # "send READ msg
          ((TX_STATE==SEND_DB0)& !CLK25PH & !CLK12PH) # "send read databyte 0
          ((TX_STATE==SEND_DB1)& !CLK25PH & !CLK12PH) # "send read databyte 1
          ((TX_STATE==STR_DATA)& !CLK25PH & !CLK12PH) # "send data
          ((TX_STATE==SEND_SF )& !CLK25PH & !CLK12PH) # "send start frame msg
          ((TX_STATE==SEND_SL )& !CLK25PH & !CLK12PH); "send start line msg DORRDY := LDIM # (LDGA & CGA1) # LDHNVH # LDDOR
                    # LDCS # LDCMD # LDSUH  "  # LDMOD
                    # DORRDY & !(TX_STATE == SET_READ);

State_diagram [TXS2,TXS1,TXS0]

" Send something if DORRDY            (data in DOR to go)
"           or  (LINECT0 and OFIFEF0) (line data ready)
"           or  (LINECT1 and OFIFEF1)          "
"           or  (LINECT2 and OFIFEF2)          "
"
" Also send START FRAME and START LINE messages when necessary " The following are state machine outputs. Use the 'with' syntax
" to avoid the one-clock delay.
" TXC, OFIFRE[2..0], OFIFOE[2..0], OUTHI, DOROE STATE WAIT_SEND:
                  " Use CLK25PH and CLK12PH to phase align as
                  " we start the send sequence.

if (DORRDY & !CLK25PH & CLK12PH) then SET_READ
                          with TXC := 3 ;
                                  OFIFRE0 := 0;
                                  OFIFRE1 := 0;
                                  OFIFRE2 := 0;
                                  OFIFOE0 := 0;
                                  OFIFOE1 := 0;
                                  OFIFOE2 := 0;
                                  OUTHI   := 0;
                                  DOROE   := 0;
                          endwith;
                  else if (SFRAME & !CLK25PH & CLK12PH) then SEND_SF
                          with TXC := 13 ;
                                  OFIFRE0 := 0;
                                  OFIFRE1 := 0;
                                  OFIFRE2 := 0;
                                  OFIFOE0 := 0;
                                  OFIFOE1 := 0;
                                  OFIFOE2 := 0;
                                  OUTHI   := 0;
                                  DOROE   := 0;
                          endwith;
                  else if (LINCT0 & !OFIFEF0 & !CLK25PH & CLK12PH & FLGSVLD)
                        # (LINCT1 & !OFIFEF1 & !CLK25PH & CLK12PH & FLGSVLD)
```

64

```
                    ; (LINCT2 & .FEF2 & !CLK25PH & CLK12PH & FLGSVLD)
                    then RD_FIFO
                        with TXC := 0;
                            OFIFRE0 := LINCT0;
                            OFIFOE0 := LINCT0;
                            OFIFRE1 := LINCT1;
                            OFIFOE1 := LINCT1;
                            OFIFRE2 := LINCT2;
                            OFIFOE2 := LINCT2;
                            OUTHI   := 0;
                            DOROE   := 0;
                        endwith;
                    else WAIT_SEND
                        with TXC := 0 ;
                            OFIFRE0 := 0;
                            OFIFRE1 := 0;
                            OFIFRE2 := 0;
                            OFIFOE0 := 0;
                            OFIFOE1 := 0;
                            OFIFOE2 := 0;
                            OUTHI   := 0;
                            DOROE   := 0;
                        endwith;
        STATE SET_READ:
            if (CLK12PH & CLK25PH) then SEND_DB0
                with TXC := 0 ;
                    OFIFRE0 := 0;
                    OFIFRE1 := 0;
                    OFIFRE2 := 0;
                    OFIFOE0 := 0;
                    OFIFOE1 := 0;
                    OFIFOE2 := 0;
                    OUTHI   := 0;
                    DOROE   := 1;
                endwith;
            else SET_READ
                with TXC := 3 ;
                    OFIFRE0 := 0;
                    OFIFRE1 := 0;
                    OFIFRE2 := 0;
                    OFIFOE0 := 0;
                    OFIFOE1 := 0;
                    OFIFOE2 := 0;
                    OUTHI   := 0;
                    DOROE   := 0;
                endwith;
        STATE SEND_DB0:
            if (CLK12PH & CLK25PH) then SEND_DB1
                with TXC := 0;
                    OFIFRE0 := 0;
                    OFIFRE1 := 0;
                    OFIFRE2 := 0;
                    OFIFOE0 := 0;
                    OFIFOE1 := 0;
                    OFIFOE2 := 0;
                    OUTHI   := 1;
                    DOROE   := 1;
                endwith;
            else SEND_DB0
                with TXC := 0;
```

221/228
PATENT

```
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTBI    := 0;
                        DOROE    := 1;
                    endwith;
        STATE SEND_DB1:
            if (CLK25PH & CLK12PH) then WAIT_SEND
                    with TXC := 0;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTBI    := 0;
                        DOROE    := 0;
                    endwith;
            else SEND_DB1
                    with TXC := 0;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTBI    := 1;
                        DOROE    := 1;
                    endwith;
        STATE RD_FIFO:              " FIFOs read enabled one clock
            goto STR_DATA
                    with TXC := 0;
                        OFIFRE0  := 0;
                        OFIFRE1  := 0;
                        OFIFRE2  := 0;
                        OFIFOE0  := LINCT0;
                        OFIFOE1  := LINCT1;
                        OFIFOE2  := LINCT2;
                        OUTBI    := 0;
                        DOROE    := 0;
                    endwith;
        STATE STR_DATA:
            if (CLK25PH & CLK12PH &
                (LINCT0&OFIFSO0 / LINCT1&OFIFSO1 / LINCT2&OFIFSO2))
                                    then SEND_SL
                    with TXC := 14;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTBI    := 0;
                        DOROE    := 0;
                    endwith;
            else if (CLK25PH & CLK12PH) then WAIT_SEND
                    with TXC := 0;
```

66

```
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTHI    := 0;
                        DOROE    := 0;
                    endwith;
            else STR_DATA
                    with TXC := 0;
                        OFIFRE0  := 0;
                        OFIFRE1  := 0;
                        OFIFRE2  := 0;
                        OFIFOE0  := LINCT0;
                        OFIFOE1  := LINCT1;
                        OFIFOE2  := LINCT2;
                        OUTHI    := 0;
                        DOROE    := 0;
                    endwith;
STATE SEND_SF:
        if (CLK25PH & CLK12PH) then WAIT_SEND
                    with TXC := 0;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTHI    := 0;
                        DOROE    := 0;
                    endwith;
            else SEND_SF
                    with TXC := 13;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTHI    := 0;
                        DOROE    := 0;
                    endwith;
STATE SEND_SL:
        if (CLK25PH & CLK12PH) then WAIT_SEND
                    with TXC := 0;
                        OFIFRE0  := 0;
                        OFIFRE1  := 0;
                        OFIFRE2  := 0;
                        OFIFOE0  := 0;
                        OFIFOE1  := 0;
                        OFIFOE2  := 0;
                        OUTHI    := 0;
                        DOROE    := 0;
                    endwith;
            else SEND_SL
                    with TXC := 14;
                        OFIFRE0  := 0;
                        OFIFRE1  := 0;
                        OFIFRE2  := 0;
```

```
            OFIFOE  := 0;
            OFIFOE1 := 0;
            OFIFOE2 := 0;
            OUTHI   := 0;
            DOROE   := 0;
        endwith;
END
```

221/228
PATENT

221/228
PATENT

EXHIBIT 2

221/228
PATENT

```
module rtetim title 'RTE Timing, Diagnostic and NVM MACH (RTETIM)
       Ver. 0; 8/15/94'
       R1U57R0 device 'MACH435A';

" Handles serial register IO
" Handles diagnostic register writes
" Decodes timing messages (or diagnostics) into sync signals
" This device uses the INTIO bus only to return read NVM data
" because it decodes SerialData register writes for itself
" to the NVM and DAC.

" to go back and solve if possible:
" SERBSY uses SERBS node in order to get a fit.
" READ and WRITE use .T when .D would be better.
" Had to take timing delays out of this device because
" needed the nodes for Serial Register Read storage.

"inputs
       CLK50 pin 20;
       CLK25PH pin 17;
       RXD0,RXD1,RXD2,RXD3,RXD4,RXD5,RXD6,RXD7 pin 5,6,7,8,9,10,12,13;
       RXC0,RXC1,RXC2,RXC3 pin 83,41,3,4;
       !RXDSTRB pin 65;
       !RXCSTRB pin 62;
       EMACC, DACCYC, NVMSEL pin 25,19,49;
       DIAG, FSDIAG, NVMDOUT, DACDOUT pin 14,15,48,51;
"      !PURST pin 82;

"unused pins but wired on board.
       MEMADD pin 39;
       HOSTREAD pin 24;
       NVIOSTRB pin 82;
       CLK12PH pin 18;
"outputs
       LDENVM, LDLNVM pin 27,28 istype 'reg_D,buffer';
       NVMCLK pin 46 istype 'reg_T,buffer';
       NVMDIN pin 47 istype 'reg_D,buffer';
       DDATA11..DDATA6 pin 81,80,79,78,77,76 istype 'reg_D,buffer';
       DDATA5..DDATA0 pin 75,73,72,71,70,69 istype 'reg_D,buffer';
       CGATE5..CGATE0 pin 60,59,58,57,56,55 istype 'reg_D,buffer';
       VSYNC pin 66 istype 'reg_D,buffer';
       HSYNC pin 67 istype 'reg_D,buffer';
       CSYNC pin 61 istype 'reg_D,buffer';
       SERBSY pin 26 istype 'buffer';
       DIAGCLK1 pin 68 istype 'reg_D,buffer';
       NVMSTRB, !SERSTRB pin 45, 52;

"Tristate outputs
       INTIO0,INTIO1,INTIO2,INTIO3 pin 29,30,31,33 istype 'reg_D,buffer';
       INTIO4,INTIO5,INTIO6,INTIO7 pin 34,35,36,37 istype 'reg_D,buffer';

"nodes
       "incoming command buffer
       BUC0,BUC1,BUC2,BUC3 node istype 'reg_D';
       ADD7,ADD6,ADD5,ADD4,ADD3,ADD2,ADD1,ADD0 node istype 'reg_D';
       "state machine state bits
       RXS1,RXS0 node istype 'reg_D';
       RXDRST node istype 'reg_D';
```

70

221/228
PATENT

```
        RXCRST node istype 'req_D';
    "serial data register
        SREG15,SREG14,SREG13,SREG12 node istype 'req_T';
        SREG11,SREG10,SREG9, SREG8  node istype 'req_T';
        SREG7, SREG6, SREG5, SREG4  node istype 'req_T';
        SREG3, SREG2, SREG1, SREG0  node istype 'req_T';
    "serial holding register
        SHR15,SHR14,SHR13,SHR12 node istype 'req_T';
        SHR11,SHR10,SHR9, SHR8  node istype 'req_T';
        SHR7, SHR6, SHR5, SHR4  node istype 'req_T';
        SHR3, SHR2, SHR1, SHR0  node istype 'req_T';
    "other
        INTIOEN node istype 'req_D';
        DCTRL3,DCTRL2,DCTRL1,DCTRL0 node istype 'req_D';
        DIAGCLK0 node istype 'req_D';
        CGATE node istype 'req_T';
        SHIFTING node istype 'req_D';
        SHFTTIH4..SHFTTIH0, SHFTCT3..SHFTCT0 node istype 'req_T';
        READ, WRITE, SERBS node istype 'req_T';
        SERIO, WRSREGH, WRSREGL node istype 'req_D';
        USEDIAG node;

VSDELAY0,HSDELAY0,CSDELAY0 node istype 'req_T';
"       CGDELAY4..CGDELAY0 node istype 'req_D';
"       VSDELAY5..VSDELAY1 node istype 'req_D';
"       HSDELAY5..HSDELAY1 node istype 'req_D';
"       CSDELAY5..CSDELAY1 node istype 'req_D';

"constants
    H,L,X,C,Z = 1,0,.X.,.C.,.Z.;
    INTIO = [INTIO7..INTIO0];
    DREGL = [DDATA7..DDATA0];
    DREGH = [DCTRL3..DCTRL0, DDATA11..DDATA8];      "Diagnostic reg
    SREGL = [SREG7..SREG0];                          "Serial reg
    SREGH = [SREG15..SREG8];
    SHFTOUTH = [SREG14..SREG7];                     "Serial shifting (write)
    SHFTOUTL = [SREG6..SREG0,SREG15];               "Serial shifting (write)
    SHR      = [SHR15..SHR0];
    SHRIN    = [SHR14..SHR0,NVMDOUT];
    SHRH     = [SHR15..SHR8];
    SHRL     = [SHR7..SHR0];
    DCTRL = [DCTRL3..DCTRL0];
    DDATA = [DDATA11..DDATA0];
    RXD = [RXD7..RXD0];
    RXC = [RXC3..RXC0];
    BGC = [BGC3..BGC0];
    ADD = [ADD7..ADD0];
    RX_STATE = [RXS1..RXS0];
    SHFTTIH = [NVMCLK,SHFTTIH4..SHFTTIH0];
    SHFTCT = [SHFTCT3..SHFTCT0];
TIMSIGS=[VSYNC,HSYNC,CSYNC,CGATE,CGATE0..CGATE5,VSDELAY0,HSDELAY0,CSDELAY0];

"       CGDEL0 = [CGDELAY4..CGDELAY0];
"       CGDELI = [CGDELAY3..CGDELAY0,CGATE];
"       VSDEL0 = [VSYNC,VSDELAY5..VSDELAY1];
"       VSDELI = [VSDELAY5..VSDELAY0];
"       HSDEL0 = [HSYNC,HSDELAY5..HSDELAY1];
"       HSDELI = [HSDELAY5..HSDELAY0];
"       CSDEL0 = [CSYNC,CSDELAY5..CSDELAY1];
```

71

221/228
PATENT

```
"       CSDELI = {CSDELAY5..CSDELA. ,,

Declarations
        WAIT_FOR_CMD = [0,0];
        WAIT_FOR_ADD = [0,1];
        WAIT_FOR_DB0 = [1,1];
        WAIT_FOR_DB1 = [1,0];

START_LINE   = [0,1,0,0];
        START_FRAME  = [0,1,0,1];
        START_COUNT  = [0,1,1,0];
        STOP_COUNT   = [0,1,1,1];
        END_FRAME    = [1,0,0,0];
        END_LINE     = [1,0,1,0];
        START_GAIN   = [1,1,1,1];

equations

" CLK12PH and CLK25PH are in phase with the RX Taxi output.
" Use the strobes and phase clocks to indicate when a message received
" Incoming data is valid when the RST is true and one clock cycle after " Tristate unused signals CLK12PH.oe   = 0;
MEMADD.oe    = 0;
HOSTREAD.oe  = 0;
NVIOSTRB.oe  = 0;

RXCRST.clk = CLK50;
        RXDRST.clk = CLK50;
        RXCRST := RXCSTRB & !RXCRST & !CLK25PH;
        RXDRST := RXDSTRB & !RXDRST & !CLK25PH;

" This MACH decodes Taxi input commands
"       1 = WRITE REGISTER
"       2 = READ REGISTER
" for address 38 = DiagnosticControl register
" and address 39 = SerialData register
" and
"       4 = START IMAGE LINE
"       5 = START IMAGE FRAME
"       6 = START IMAGE COUNT
"       7 = STOP COUNT
"       8 = END IMAGE FRAME
"       10 = END IMAGE LINE
"       15 = START GAIN COUNT " The reads and writes are handled by a state machine
" The timing messages are decoded directly ADD.clk   = RXDSTRB;
        DREGL.clk = RXDSTRB;
        DREGH.clk = RXDSTRB;
        SREGL.clk = CLK50;
        SREGH.clk = CLK50;
        BGC.clk   = RXCSTRB;

" Address lines change for every READ or WRITE command detected,
" even if not our address.
```

72

```
" This is 'transparent latch' synta.. .DD = RXD when state WAIT_FOR_ADD
" but is latched when state changes.

ADD    :=  RXD   &  (RX_STATE == WAIT_FOR_ADD)
                #  ADD   &  (RX_STATE != WAIT_FOR_ADD);

" Address 38 is the diagnostic register. Latch the low and high
" bytes separately as they are sent.

DREGH  :=  RXD   &  (RX_STATE == WAIT_FOR_DB1) & (ADD == 38)
                #  DREGH & !((RX_STATE == WAIT_FOR_DB1) & (ADD == 38));
        DREGL  :=  RXD   &  (RX_STATE == WAIT_FOR_DB0) & (ADD == 38)
                #  DREGL & !((RX_STATE == WAIT_FOR_DB0) & (ADD == 38));

BUC  := RXC;

" Use the strobe resets to flag when command or data is received

" A state machine decodes the Taxi write diagnostic register
" New data in the diagnostic register is flagged by state
" WAIT_FOR_DB1 & RXDRST & (ADD == 38)
" This condition is decoded to generate the diagnostic clock DIAGCLK
" and the diagnostic timing replacement in the appropriate modes.

RX_STATE.clk = CLK50;
"       RX_STATE.ar  = PORST;

State_diagram [RXS1,RXS0]

state WAIT_FOR_CMD:
            if (RXCRST & ((BUC == 1) # (BUC == 2)))  " Reg read or write
               then WAIT_FOR_ADD;
            else
                WAIT_FOR_CMD;
    state WAIT_FOR_ADD:
            if RXDRST & WRITE & ((ADD == 38) # (ADD == 39))
               then WAIT_FOR_DB0;
            else if RXDRST
               then WAIT_FOR_CMD;
            else
                WAIT_FOR_ADD;
    state WAIT_FOR_DB0:
            if RXDRST
               then WAIT_FOR_DB1;
            else
                WAIT_FOR_DB0;
    state WAIT_FOR_DB1:
            if RXDRST
               then WAIT_FOR_CMD
            else
                WAIT_FOR_DB1;

Equations

" ******************** Decode the timing signals ***************************
" OK to use combinational logic for USEDIAG, its inputs are
" effectively DC.

USEDIAG = DIAG & !FSDIAG;
```

```
    TIMSIGS.clk    = CLK50;
"   TIMSIGS.ar     = PURST;

VSDELAY0.t = RXCRST & (BUC == START_FRAME) & !USEDIAG & VSDELAY0
              # RXCRST & (BUC == END_FRAME)   & !USEDIAG & !VSDELAY0
              # DIAGCLK0 & (DCTRL == START_FRAME) & USEDIAG & VSDELAY0
              # DIAGCLK0 & (DCTRL == END_FRAME) & USEDIAG & !VSDELAY0;

HSDELAY0.t = RXCRST & (BUC == START_FRAME) & !USEDIAG & HSDELAY0
              # RXCRST & (BUC == START_LINE)  & !USEDIAG & HSDELAY0
              # RXCRST & (BUC == END_FRAME)   & !USEDIAG & !HSDELAY0
              # RXCRST & (BUC == END_LINE)    & !USEDIAG & !HSDELAY0
              # DIAGCLK0 & (DCTRL == START_FRAME) & USEDIAG & HSDELAY0
              # DIAGCLK0 & (DCTRL == START_LINE)  & USEDIAG & HSDELAY0
              # DIAGCLK0 & (DCTRL == END_FRAME) & USEDIAG & !HSDELAY0
              # DIAGCLK0 & (DCTRL == END_LINE)  & USEDIAG & !HSDELAY0;

CGATE.t = RXCRST & (BUC == START_FRAME) & !USEDIAG & !CGATE
            # RXCRST & (BUC == START_LINE)  & !USEDIAG & !CGATE
            # RXCRST & (BUC == START_COUNT) & !USEDIAG & !CGATE
            # RXCRST & (BUC == START_GAIN)  & !USEDIAG & !CGATE
            # RXCRST & (BUC == END_FRAME)   & !USEDIAG & !CGATE
            # RXCRST & (BUC == END_LINE)    & !USEDIAG & !CGATE
            # RXCRST & (BUC == STOP_COUNT)  & !USEDIAG & CGATE
            # DIAGCLK0 & (DCTRL == START_FRAME) & USEDIAG & !CGATE
            # DIAGCLK0 & (DCTRL == START_LINE)  & USEDIAG & !CGATE
            # DIAGCLK0 & (DCTRL == START_COUNT) & USEDIAG & !CGATE
            # DIAGCLK0 & (DCTRL == START_GAIN)  & USEDIAG & !CGATE
            # DIAGCLK0 & (DCTRL == END_FRAME) & USEDIAG & !CGATE
            # DIAGCLK0 & (DCTRL == END_LINE)  & USEDIAG & !CGATE
            # DIAGCLK0 & (DCTRL == STOP_COUNT)& USEDIAG & CGATE;

CSDELAY0.t = RXCRST & (BUC == START_GAIN)  & !USEDIAG & !CSDELAY0
              # RXCRST & (BUC == STOP_COUNT) & !USEDIAG & CSDELAY0
              # DIAGCLK0 & (DCTRL == START_GAIN) & USEDIAG & !CSDELAY0
              # DIAGCLK0 & (DCTRL == STOP_COUNT) & USEDIAG & CSDELAY0;

"******************** Timing signal delays ********************

"       CGDEL0.clk = CLK50;
"       VSDEL0.clk = CLK50;
"       HSDEL0.clk = CLK50;
"       CSDEL0.clk = CLK50;
"
"       CGDEL0 := CGDELI;
"       VSDEL0 := VSDELI;
"       HSDEL0 := HSDELI;
"       CSDEL0 := CSDELI;
"
"       CGATE0 := CGDELAY4;
"       CGATE1 := CGDELAY4;
"       CGATE2 := CGDELAY4;
"       CGATE3 := CGDELAY4;
"       CGATE4 := CGDELAY4;
"       CGATE5 := CGDELAY4;
"
        VSYNC := VSDELAY0;
        HSYNC := HSDELAY0;
```

74

```
        CSYNC  := CSDELAY0;
        CGATE0 := CGATE;
        CGATE1 := CGATE;
        CGATE2 := CGATE;
        CGATE3 := CGATE;
        CGATE4 := CGATE;
        CGATE5 := CGATE;

"********************** Diagnostic data out *********************************

" Decode the data written to the diagnostic register

DIAGCLK0.clk = CLK50; " DIAGCLK0 flags new diagnostic data
        DIAGCLK1.clk = CLK50;

DIAGCLK0 := (RX_STATE == WAIT_FOR_DB1) & (ADD == 38)
                    & RXDRST & USEDIAG;

" Toggle DIAGLCK1 once only, if the diagnostic control bits are 0
" indicating that this is a diagnostic data strobe

DIAGCLK1 := DIAGCLK0 & (DCTRL == 0);

" ************************* Shift serial data *******************************

" Data clock is 50/64 MHz (slowest device max. speed is 1 MHz)
" SHFTTIM is clock divider to match speed of device
" SHFTCT is counter for serial 16-bit shift, 1 bit shifted
" and output every 50/64 MHz count
" Everything starts when SERIO goes true with READ or WRITE set
" NVMSEL line is used to decode whether NVM or DAC is active " If NVM, then NVMSTRB is true for the duration of READ or WRITE
" Whether read or write we clock the NVM 16 times.
" If NVM WRITE -
" shift out of SREG through NVMDIN and into SREGO from NVMDIN (so
" SREG is unaltered)
" If NVM READ -
" send what is already in SREG to DOR
" shift into SREG from NVMDOUT " If DAC, then SERSTRB is true for the duration of DACCYC (which
" is a bit written by the host, not controlled here).

" Decode both SHFTTIM and SHFTCT to
"  - shift data to serial output pin NVMDIN (write)
"  - shift data in from serial input pin NVMDOUT (read)
"  - generate clock to serial device
"  - keep SERBSY true till operation complete
"  - reset READ and WRITE lines when complete " Msb of SHFTTIM is NVMCLK SHFTTIM.clk  = CLK50;
        SHFTCT.clk   = CLK50;
        SHIFTING.clk = CLK50;
        READ.clk     = CLK50;
        WRITE.clk    = CLK50;
```

75

```
"       SHFTTIH.ar  = PURST;
"       SHFTCT.ar   = PURST;
"       SHIFTING.ar = PURST;
"       READ.ar     = PURST;
"       WRITE.ar    = PURST;

SHFTTIH.t = (SHFTTIH $ (SHFTTIH+1)) & SERIO & (READ # WRITE) " Count
                  # (SHFTTIH $ (0)) & SERIO & !(READ # WRITE);  " Reset to 0

SHIFTING := (SHFTTIH == 32) & WRITE
                  # (SHFTTIH == 57) & READ;

SHFTCT.t  = (SHFTCT $ (SHFTCT+1)) & SHIFTING       " Count shifts
                  # (SHFTCT $ (15)) & !(READ # WRITE);     " Reset to -1

" READ and WRITE are set when a read or write register command is decoded
" They are cleared either by an address other than 39 (SerialData register)
" or when the IO to address 39 is complete.

" This is D-logic but alas it does not fit in D

"       READ := RXCRST & (BUC == 1)
"            # READ & !((RXDRST & (RX_STATE == WAIT_FOR_ADD) & (ADD != 39))
"                       #((SHFTCT == 15) & (SHFTTIH == 63)));
"       WRITE := RXCRST & (BUC == 2)
"            # WRITE & !((RXDRST & (RX_STATE == WAIT_FOR_ADD) & (ADD != 39))
"                       #((SHFTCT == 15) & (SHFTTIH == 63)));
"
" so we have to use T WRITE.t = RXCRST & (BUC == 1) & !WRITE

RXDRST & (RX_STATE == WAIT_FOR_ADD) & (ADD != 39) & WRITE

# (SHFTCT == 15) & (SHFTTIH == 63) & WRITE;
        READ.t  = RXCRST & (BUC == 2) & !READ
                # RXDRST & (RX_STATE == WAIT_FOR_ADD) & (ADD != 39) & READ
                # (SHFTCT == 15) & (SHFTTIH == 63) & READ;

SERBS.t = RXDRST & (RX_STATE==WAIT_FOR_ADD) & (ADD==39) & !SERBS
                # (SHFTCT == 15) & (SHFTTIH == 63) & SERBS;

" SERBSY gross timing not critical, this dissociates the node from the pin
" and gives a better chance of fitting

SERBSY = SERBS;

" Serial register data changes when written to from host during a
" WRITE operation, or when shifted out as the write is executed,
" or when shifted in during a READ operation " WRSREGx (Write Serial Register) lines are transparent while
" the state machine is waiting for the databyte after receiving
" the WRITE SERIAL REGISTER sequence. It latches as soon as the
" data is received, signalled by the state machine state changing.
" This happens as a result of a RXDRST pulse. The RXD data is
" guaranteed one cycle after RXDRST. Hence pre-decoding of the
" WRSREGx lines is OK, and it saves routing resources.
" SERIO (Serial IO in progress) is set true when there is an IO access
" to address 39, and cleared when the read or write completes.
```

221/228
PATENT

```
        SERBS.clk   = CLK50;
        NVHDIN.clk  = CLK50;
        SERIO.clk   = CLK50;
        WRSREGH.clk = CLK50;
        WRSREGL.clk = CLK50;
        SHR.clk     = CLK50;

"       SERBS.ar    = PURST;
"       NVHDIN.ar   = PURST;
"       SERIO.ar    = PURST;
"       WRSREGH.ar  = PURST;
"       WRSREGL.ar  = PURST;
"       SHR.ar      = PURST;

SERIO   :=  RXDRST & WRITE & (ADD == 39) & (RX_STATE == WAIT_FOR_DB1)
                 #  RXDRST & READ  & (ADD == 39) & (RX_STATE == WAIT_FOR_ADD)
                 #  SERIO  & !((SHFTCT == 15) & (SHFTTIM == 63));
        WRSREGH :=  (RX_STATE == WAIT_FOR_DB1) & (ADD == 39);
        WRSREGL :=  (RX_STATE == WAIT_FOR_DB0) & (ADD == 39);

SREGH.t =  (SREGH $ RXD) & WRSREGH
                #  (SREGH $ SHFTOUTH) & SHIFTING & WRITE;

SREGL.t =  (SREGL $ RXD) & WRSREGL
                #  (SREGL $ SHFTOUTL) & SHIFTING & WRITE;

SHR.t   =  (SHR $ SHRIN) & SHIFTING & READ;

NVHDIN  := SREG15 & WRITE;

NVHSTRB =  DACCYC & NVHSEL;
        SERSTRB =  DACCYC & !NVHSEL;

" ************************ Serial read - data to host cycle ****************

" The dataword in the SHR is sent to the host when a read is
" received. The read loads the SHR with new data immediately afterwards.
" Hence the host is reading data one cycle behind.
" The serial shift counters are convenient to decode to do this. Note that
" no serial shift occurs until the timing counter reaches 63 so the data
" is available for sending for plenty of time.

" 50HHz    |||||||||||||||||||||||||||||||||||||||||||||||||
" READ     _____----------------------------------------
" SERIO    _____--------------------------------------
" SHFTTIM  000000000000123456789
" SHFTCT   000000000000000000000
" INTIO    ZZZZZZZZZZZZZLLLHHHHZZZ
" LDLNVH   _____-___
" LDHNVH   _____-__

INTIO.clk   = CLK50;
        INTIOEN.clk = CLK50;
        LDLNVH.clk  = CLK50;
        LDHNVH.clk  = CLK50;

"       INTIO.ar    = PURST;
"       INTIOEN.ar  = PURST;
```

221/228
PATENT

```
"       LDLNVH.ar  = PURST;
"       LDENVH.ar  = PURST;

INTIO.oe   = INTIOEN;

INTIO  := SHRH & SHFTTIH2
               /  SHRL & !SHFTTIH2;
        LDLNVH := HMACC & READ & (SHFTTIH == 2) & (SHFTCT == 15);
        LDENVH := HMACC & READ & (SHFTTIH == 5) & (SHFTCT == 15);
        INTIOEN := HMACC & READ & (SHFTTIH<9)&(SHFTTIH>0) & (SHFTCT == 15);
"  INTIOEN := 0;  For testing
END
```

221/228
PATENT

EXHIBIT 3

221/228
PATENT

```
module rtehm title 'RTE Host Memory Mode MACH (RTEHM)
        Ver. 0; 8/3/94'
        R1U43R0 device 'MACH435A';

"inputs
        CLK50 pin 23;
        CLK25RX pin 20;
        RXD0,RXD1,RXD2,RXD3,RXD4,RXD5,RXD6,RXD7 pin 5,6,7,8,9,10,12,13;
        RXC0,RXC1,RXC2,RXC3 pin 83,41,3,4;
        !RXDSTRB pin 62;
        !RXCSTRB pin 65;
        CLK25PH pin 17;
        EMACC pin 54;
        LDIH, LDGA pin 57,59;
        !PURST pin 50;
        SHGFRA pin 29;

"outputs
        CLK12RX   pin 82 istype 'reg_D, buffer';
        RXCRST pin 45 istype 'reg_D, buffer';
        RXDRST pin 46 istype 'reg_D, buffer';
        HEMADD, IMMADS, GAMADS, NVMADS pin 25,26,27,28 istype 'reg_D, buffer';
        !XCVRIEN pin 38 istype 'reg_T, buffer';
        XCVRDIR pin 37 istype 'reg_D, buffer';
        !XCVRGHEN, !XCVRGLEN pin 40, 39 istype 'reg_T, buffer';
        HOSTREAD pin 19 istype 'reg_T, buffer';
        IHIOSTRB, GAIOSTRB pin 33,34 istype 'reg_T, buffer';

"I/Os
        INTIO0,INTIO1,INTIO2,INTIO3 pin 69,70,71,72 istype 'reg_D,buffer';
        INTIO4,INTIO5,INTIO6,INTIO7 pin 73,75,76,77 istype 'reg_D,buffer';

"Wired on board but not used
        NVIOSTRB pin 35;
        CLK12PH pin 18;
        LDLNVH pin 61;
        LDHNVH pin 60;

"nodes
        "incoming data buffer
        BUD0, BUD1, BUD2, BUD3  pin istype 'reg_D, buffer';
        BUD4, BUD5, BUD6, BUD7  node istype 'reg_D';
        BUD8, BUD9, BUD10,BUD11 pin istype 'reg_D, buffer';
        BUD12,BUD13,BUD14,BUD15 node istype 'reg_D';
        "incoming register address
        RAD0, RAD1, RAD2, RAD3 node istype 'reg_D';
        RAD4, RAD5, RAD6, RAD7 node istype 'reg_D';
        "incoming memory select buffer
        ADD0, ADD1, ADD2, ADD3 node istype 'reg_D';
        ADD4, ADD5, ADD6, ADD7 node istype 'reg_D';
        ADD8, ADD9, ADD10,ADD11 node istype 'reg_D';
        "incoming command buffer
        BCC0,BUC1,BUC2,BUC3 node istype 'reg_D';
        "state machine state bits
        RXS1,RXS0 pin istype 'reg_D,buffer';
        IOS4,IOS3,IOS2,IOS1,IOS0 pin istype 'reg_D,buffer';
        "flags
        HEMADDR, MEMDATA, GOWRITE pin istype 'reg_T,buffer';
```

80

221/228
PATENT

```
    "other
        INTIOEN, OUTHI node istype 'reg_T';
        DGHEN node istype 'reg_D';

"constants
        H,L,X,C,Z = 1,0,.X.,.C.,.Z.;
"       INCMD  = [RXC3..RXC0];
"       OUTCMD = [TXC3..TXC0];
"       INDATA = [RXD7..RXD0];
        INTIO  = [INTIO7..INTIO0];
        RXD    = [RXD7..RXD0];
        RXC    = [RXC3..RXC0];
        BUDL   = [BUD7..BUD0];
        BUDH   = [BUD15..BUD8];
        RAD    = [RAD7..RAD0];
        ADD    = [ADD11..ADD0];
        ADDBITS = [0,BUD10..BUD0];
        SHFADDIN  = [ADD10..ADD0,MEMADD];
        SHFADDOUT = [MEMADD,ADD10..ADD0];
        BUC    = [BUC3..BUC0];
        RX_STATE = [RXS1..RXS0];
        IO_STATE = [IOS4..IOS0];

" T/D flip-flop rules.
" T flip-flop logic may only be used if all the inputs to the T are
" internal feedback lines, or guaranteed to be set up several clock
" cycles ahead of the switch (eg a DC control line like EMACC).

Declarations

WAIT_FOR_CMD = [0,0];
        WAIT_FOR_ADD = [0,1];
        WAIT_FOR_DB0 = [1,1];
        WAIT_FOR_DB1 = [1,0];

Equations

"CLOCK GENERATION

CLK12PH.oe = 0;

"CLK12RX is CLK25RX divide-by-2

CLK12RX.clk = CLK25RX;
        CLK12RX := !CLK12RX;

" CLK12PH and CLK25PH are in phase with the RX Taxi output.
" Generate the external flip-flop resets RXCRST.clk = CLK50;
        RXDRST.clk = CLK50;
        RXCRST := RXCSTRB & !RXCRST & !CLK25PH;
        RXDRST := RXDSTRB & !RXDRST & !CLK25PH;

" ********************** Taxi Input Command State Machine ****************

" This MACH decodes Taxi input commands
"     1 = WRITE REGISTER
"     2 = READ REGISTER
" for addresses
```

81

```
"     36 = MemoryAddress register
"     37 = MemoryData register

" Use the edge of the strobe to clock the Taxi command or data
" into a local buffer " Command data is used to start off state machine, after that it
" may be overwritten by the next command.

" Taxi data may also be overwritten by the next data. However timing
" messages have no data, so it won't be overwritten until the next
" read or write request BUDH.clk  = RXDSTRB;
        BUDL.clk  = RXDSTRB;
        RAD.clk   = RXDSTRB;
        BUC.clk   = RXCSTRB;

BUDH :=   (RXD  & (RX_STATE == WAIT_FOR_DB1))
                # (BUDH & (RX_STATE != WAIT_FOR_DB1));
        BUDL :=   (RXD  & (RX_STATE == WAIT_FOR_DB0))
                # (BUDL & (RX_STATE != WAIT_FOR_DB0));
        RAD  :=   (RXD  & (RX_STATE == WAIT_FOR_ADD))
                # (RAD  & (RX_STATE != WAIT_FOR_ADD));
        BUC  := RXC;

" Use the strobe resets to flag when command or data is received

" A state machine decodes the Taxi command and data inputs
" It sets flags for other state machines to handle the received data RX_STATE.clk = CLK50;
        HOSTREAD.clk = CLK50;
        MEMADDR.clk  = CLK50;
        MEMDATA.clk  = CLK50;
        GOWRITE.clk  = CLK50;

State_diagram [RXS1,RXS0]

state WAIT_FOR_CMD:
           if (RXCRST & (BUC == 1) & EMACC & !SNGFRA) " Write req
              then WAIT_FOR_ADD;
           else if (RXCRST & (BUC == 2) & EMACC & !SNGFRA) " Read req
              then WAIT_FOR_ADD;
           else WAIT_FOR_CMD;

state WAIT_FOR_ADD:
           if (RXDRST & (RAD == 36) & !HOSTREAD) " Mem addr write
              then WAIT_FOR_DB0;
           else if (RXDRST & (RAD == 37) & !HOSTREAD) " Mem data write
              then WAIT_FOR_DB0;
           else if RXDRST     " (Decode read addresses in flag logic)
              then WAIT_FOR_CMD;
           else WAIT_FOR_ADD;

state WAIT_FOR_DB0:      " DB0 data buffer loaded in this state
           if RXDRST
              then WAIT_FOR_DB1;
```

82

```
             else
                 WAIT_FOR_DB0;

state WAIT_FOR_DB1:     " DB1 data buffer loaded in this state
             if RXDRST       " Decode this transition to set GOWRITE
                then WAIT_FOR_CMD;
             else
                 WAIT_FOR_DB1;

" ******************** IO State Machine ***************************************

" This state machine watches for the MEMADDR, MEMDATA and GOWRITE flags
" HOSTREAD indicates the action to be taken. The flags are cleared
" when the read or write is complete (see flag decode logic).
" MEMADDR, MEMDATA and HOSTREAD are set as the information comes in
" from the Taxilink. GOWRITE is set when all the necessary information
" is latched and the write operation can be performed.

Declarations
        WAIT_FOR_FLG   = [0,0,0,0,0];
        WRITE_ADDRESS  = [0,0,0,0,1];
        WRITE_DATA     = [0,0,0,1,1];
        READ_ADDRESS   = [0,0,0,1,0];
        READ_DATA      = [0,0,1,1,0];
        MEMOUT_01      = [1,0,0,0,0];
        MEMOUT_02      = [1,0,0,0,1];
        MEMOUT_03      = [1,0,0,1,1];
        MEMOUT_04      = [1,0,0,1,0];
        MEMOUT_05      = [1,0,1,1,0];
        MEMOUT_06      = [1,0,1,1,1];
        MEMOUT_07      = [1,0,1,0,1];
        MEMOUT_08      = [1,0,1,0,0];
        MEMOUT_09      = [1,1,0,0,0];
        MEMOUT_10      = [1,1,1,1,1];
        MEMOUT_11      = [1,1,1,1,0];
        WRDATA_01      = [0,0,1,1,1];
        WRDATA_02      = [0,0,1,0,1];
        WRDATA_03      = [0,0,1,0,0];
        WRDATA_04      = [0,1,1,0,0];
        WRDATA_05      = [0,1,1,0,1];
        WRDATA_06      = [0,1,1,1,1];
        WRDATA_07      = [0,1,1,1,0];

Equations

IO_STATE.clk = CLK50;
        MEMADD.clk   = CLK50;
        GAMADS.clk   = CLK50;
        IMMADS.clk   = CLK50;
        NVMADS.clk   = CLK50;
        XCVRDIR.clk  = CLK50;    " A -> B = read, B -> A = write
        XCVRIEN.clk  = CLK50;
        XCVRGHEN.clk = CLK50;
        XCVRGLEN.clk = CLK50;
        IMIOSTRB.clk = CLK50;
        GAIOSTRB.clk = CLK50;
        INTIO.clk    = CLK50;
        INTIOEN.clk  = CLK50;
        OUTHI.clk    = CLK50;
        ADD.clk      = CLK50;
```

83

221/228
PATENT

```
        DGHEN.clk    = CLK50;

GAMADS := IOS4 & GOWRITE & (EMACC&!SNGFRA) & ADD11;
        IMMADS := IOS4 & GOWRITE & (EMACC&!SNGFRA) & !ADD11;

INTIO.oe = INTIOEN;
        INTIO := BODL & !OUTHI
               # BUDH & OUTHI;

State_diagram [IOS4,IOS3,IOS2,IOS1,IOS0]

state WAIT_FOR_FLG:
            if (GOWRITE & MEMADDR & !HOSTREAD ) " Write address
               then WRITE_ADDRESS;
            else if (MEMADDR & HOSTREAD ) " Read address
               then READ_ADDRESS;
            else if (GOWRITE & MEMDATA & !HOSTREAD ) " Write data
               then WRDATA_01
            else if (MEMDATA & HOSTREAD ) " Read data
               then READ_DATA;
            else WAIT_FOR_FLG;
    state WRITE_ADDRESS:
            goto MEMOUT_01;
    state MEMOUT_01:
            goto MEMOUT_02;
    state MEMOUT_02:
            goto MEMOUT_03;
    state MEMOUT_03:
            goto MEMOUT_04;
    state MEMOUT_04:
            goto MEMOUT_05;
    state MEMOUT_05:
            goto MEMOUT_06;
    state MEMOUT_06:
            goto MEMOUT_07;
    state MEMOUT_07:
            goto MEMOUT_08;
    state MEMOUT_08:
            goto MEMOUT_09;
    state MEMOUT_09:
            goto MEMOUT_10;
    state MEMOUT_10:
            goto MEMOUT_11;
    state MEMOUT_11:
            goto WAIT_FOR_FLG;
    state WRDATA_01:
            goto WRDATA_02;
    state WRDATA_02:
            goto WRDATA_03;
    state WRDATA_03:
            goto WRDATA_04;
    state WRDATA_04:
            goto WRDATA_05;
    state WRDATA_05:
            goto WRDATA_06;
    state WRDATA_06:
            goto WRDATA_07;
    state WRDATA_07:
" write data is complete (no handshake required) so reset everything
```

84

221/228
PATENT

```
         goto WAIT_FOR_FLG;
    state READ_ADDRESS:
         goto WAIT_FOR_FLG;
" state READ_DATA initiates all the reads but control then transfers
" to the return data strobes, LDIM, LDGA,
" which disable the transceivers when received.
    state READ_DATA:
         goto WAIT_FOR_FLG;

" *************** Control Line Decoding from State Machines ***************
"
" Flags.
" MEMADDR, MEMDATA, GOWRITE are used for communication between
" the state machines.
" The flag transitions are decoded from state machine states,
" hence will lag the states by one clock cycle.

Equations

MEMADDR.t = (RX_STATE == WAIT_FOR_ADD) & (RAD == 36) & RXDRST & !MEMADDR
          # (IO_STATE == MEMOUT_11) & MEMADDR
          # (IO_STATE == READ_ADDRESS) & MEMADDR;
MEMDATA.t = (RX_STATE == WAIT_FOR_ADD) & (RAD == 37) & RXDRST & !MEMDATA
          # (IO_STATE == WRDATA_07) & MEMDATA
          # (IO_STATE == READ_DATA) & MEMDATA;
GOWRITE.t = (RX_STATE == WAIT_FOR_DB1) & RXDRST & !GOWRITE
          # (IO_STATE == WRDATA_07) & GOWRITE
          # (IO_STATE == MEMOUT_11) & GOWRITE;

" If it is a memory address register write, catch it and shift it out

ADD11 := BUD11 & (IO_STATE == WRITE_ADDRESS)
              # ADD11 & (IO_STATE != WRITE_ADDRESS);

SHFADDOUT := ADDBITS & (IO_STATE == WRITE_ADDRESS)
              # SHFADDIN & IOS4 & GOWRITE
              # SHFADDOUT & !((IO_STATE == WRITE_ADDRESS) # IOS4 & GOWRITE);

" HOSTREAD
" HOSTREAD is used in this device and is also an output to the memory
" controllers to indicate IO direction.

HOSTREAD.t = (RX_STATE == WAIT_FOR_CMD) & (BGC == 2) & RXCRST & !HOSTREAD
               # (RX_STATE == WAIT_FOR_CMD) & (BGC == 1) & RXCRST & HOSTREAD;

"*********************** Memory Handshaking ***********************************

" Transceiver, strobes and INTIO enable control (memory data IO)
" XCVRDIR, XCVRIEN, XCVRGHEN, XCVRGLEN, INTIOEN, OUTHI
" IMIOSTRB, GAIOSTRB
" There are four cases to consider (read or write to either memory):
"
" ++++++ Image Memory Writes
" One byte transferred. HOSTREAD false. No interlock between strobes.
"
" CLK50   | |  | | | | | | | | |  | | | |
" state   WFF     X 1 X 2 X 3 X 4 X 5 X 6 X 7 X WFF
" XCVRIEN _____------------------------___
" INTIOEN _____------------------------___
                                                  85
```

```
" INTIO     IIIIIIIIIIIIIVVVVVVVVV\    /VVVVVVVIIII
" IHIOSTRB _____----_____

" ++++++ Image Memory Reads
" One byte transferred. HOSTREAD true. IHIOSTRB and LDIH are interlocked.
" This MACHs cycle is complete when byte is strobed into DOR by LDIH
"
" CLK50    |    |    |    |    |    |    |    |    |    |    |    |    |    |
" state    WFF      X RDX WFF      -
" MEMDATA  ____--------_____-_____
" XCVRIEN  _____--------------------_____
" INTIOEN  _____-_____
" IHIOSTRB _____-----------------____
" INTIO    IIIIIIIIIIIIIIIIIIIIIIII-IIIIVVVVVVVIIIIIIIIII
" LDIH     _____-___----_____
"                              ^
"                              INTIO data to DOR (RTEDA MACH)

" ++++++ GA Memory Writes
" Two bytes transferred. HOSTREAD false. No interlock between strobes.
"
" CLK50    |    |    |    |    |    |    |    |    |    |    |    |    |    |
" state    WFF      X 1 X 2 X 3 X 4 X 5 X 6 X 7 X WFF
" XCVRGLEN _____--------------------------____
" XCVRGHEN _____-------------------------____
" OUTHI    _____-----------____
" INTIOEN  _____--------------------____
" INTIO    IIIIIIIIIIIIIILLLLLLLLLLLLLXHHHHHHHHHHIIIII
" GAIOSTRB _____----_____----_____

" ++++++ GA Memory Reads
" Two bytes transferred. HOSTREAD true. GAIOSTRB and LDGA are interlocked.
" This MACHs cycle is complete when bytes are strobed into DOR by LDGA " CLK50    |    |    |    |    -|    |    |    |    |    |    |    |    |
" state    WFF      X RDX - WFF
" MEMDATA  ____--------__ -_____
" XCVRGLEN _____-- -------_____
" XCVRGHEN _____-- -_____
" (DGHEN)  _____ -_____--------_____
" INTIOEN  _____ -_____
" GAIOSTRB _____-- --------------------____
" INTIO    ZZZZZZZZZZZZZZLL -LLLLLLLZZZHHHHHHHHZZZZZZZZZZZZ
" LDGA     _____-____---------------_____
"                           ^                 ^
"                           L then H byte INTIO data to DOR (RTEDA MACH)
"                           (timed from LDGA goes high).
"
"
"
"

XCVRDIR := HOSTREAD;
        DGHEN := XCVRGHEN;

XCVRIEN.t = (IO_STATE == WRDATA_01) & !ADD11 & !XCVRIEN
                  / (IO_STATE == READ_DATA) & !ADD11 & !XCVRIEN
                                   86
```

```
                   # (IO_STATE == WR_    _07) & XCVRIEN
                   # LDIH & XCVRIEN
                   # PURST & XCVRIEN;

XCVRGLEN.t = (IO_STATE == WRDATA_01) & ADD11 & !XCVRGLEN
                   # (IO_STATE == READ_DATA) & ADD11 & !XCVRGLEN
                   # (IO_STATE == WRDATA_07) & XCVRGLEN
                   # LDGA & XCVRGLEN
                   # PURST & XCVRGLEN;

XCVRGHEN.t = (IO_STATE == WRDATA_01) & ADD11 & !XCVRGHEN   "Wr
                   # LDGA & !XCVRGLEN & !XCVRGHEN & GAIOSTRB     "Re
                   # (IO_STATE == WRDATA_07) & XCVRGHEN
                   # DGHEN & XCVRGHEN & HOSTREAD
                   # PURST & XCVRGHEN;

INTIOEN.t  = (IO_STATE == WRDATA_01) & !INTIOEN
                   # (IO_STATE == WRDATA_07) & INTIOEN;

IHIOSTRB.t = (IO_STATE == WRDATA_02) & !ADD11 & !IHIOSTRB
                   # (IO_STATE == WRDATA_03) & IHIOSTRB
                   # (IO_STATE == READ_DATA) & !ADD11 & !IHIOSTRB
                   # LDIH & IHIOSTRB;

GAIOSTRB.t = (IO_STATE == WRDATA_02) & ADD11 & !GAIOSTRB
                   # (IO_STATE == WRDATA_03) & GAIOSTRB
                   # (IO_STATE == WRDATA_05) & ADD11 & !GAIOSTRB
                   # (IO_STATE == WRDATA_06) & GAIOSTRB
                   # (IO_STATE == READ_DATA) & ADD11 & !GAIOSTRB
                   # LDGA & DGHEN & GAIOSTRB;

OUTHI.t    = (IO_STATE == WRDATA_04) & !OUTHI
                   # (IO_STATE == WRDATA_07) & OUTHI;

Test_vectors(
[CLK50,RXC,RXD,RXCSTRB,RXDSTRB,CLK25PH,EMACC]
                              ->[BUC,RX_STATE,RXCRST,RXDRST])

[.c.,  0,  0,  0,     0,    0,    0]  ->[0,WAIT_FOR_CMD,0,0];
[0,    1,  0,  1,     0,    1,    0]  ->[1,WAIT_FOR_CMD,0,0];
[0,    1,  0,  1,     0,    0,    0]  ->[1,WAIT_FOR_CMD,0,0];
[0,    1,  0,  1,     0,    1,    0]  ->[1,WAIT_FOR_CMD,0,0];
[.c.,  1,  0,  1,     0,    0,    0]  ->[1,WAIT_FOR_CMD,1,0];
[.c.,  1,  0,  0,     0,    1,    0]  ->[1,WAIT_FOR_ADD,0,0];
[.c.,  0,  0,  0,     0,    0,    0]  ->[1,WAIT_FOR_ADD,0,0];

END
```

221/228
PATENT

EXHIBIT 4

221/228
PATENT

```
module rtsctr title 'ALIGNMENT COUNTERS
      Ver. 0; 8/5/94'
      E1URO device 'I1032T08';

"inputs
      I1..I12 pin 35,80,84,68,90,87,36,83,22,40,30,81;
      DD1..DD12 pin 44,45,46,47,48,53,54,55,56,57,58,59;
      CGATE pin 93;
      FMHZ pin 62;
      SEL0,SEL1,SEL2,SEL3 pin 29,67,33,32;
      OE_,DIAG pin 78,69;
      TCLK pin 70;

"outputs
      O1..O12 pin 92,91,96,95,73,72,23,34,42,41,19,18 istype 'req_D,buffer';
      S0..S8 pin 97,98,3,4,5,6,7,8,9 istype 'req_D,buffer';

"nodes
      CA0..CA6 node istype 'req_T,buffer';
      CB0..CB6 node istype 'req_T,buffer';
      CC0..CC6 node istype 'req_T,buffer';
      EA0..EA2 node istype 'req_D,buffer';
      EB0..EB2 node istype 'req_D,buffer';
      EC0..EC2 node istype 'req_D,buffer';
      _I1.._I12 node istype 'req_D,buffer';
      FSCY1,FSCY2,FSCY3,FSCY4,SCY1,SCY2,SCY3 node;
      FS0..FS7,V1..V12,SCLK node;
      CGATEL,CAOVF,CBOVF,CCOVF node istype 'req_D,buffer';

PLSI PROPERTY 'TRY 3';
      PLSI PROPERTY 'ISP ON';
      PLSI PROPERTY 'PULLUP ON';
      PLSI PROPERTY 'STRONG_ROUTE EXTENDED';
      PLSI PROPERTY 'CLK SCLK CLK1';
      PLSI PROPERTY 'CLK FMHZ CLK2';

"constants
      H,L,X,C,Z = 1,0,.X.,.C.,.Z.;
      SEL = [SEL3..SEL0];
      S = [S8..S0];
      FS = [FS7..FS0];
      EA = [EA2..EA0];
      EB = [EB2..EB0];
      EC = [EC2..EC0];
      CA = [CA6..CA0];
      CB = [CB6..CB0];
      CC = [CC6..CC0];
      I = [I1..I12];
      IR = [I4..I1,I8..I5,I12..I9];
      O = [O1..O12];
      DD = [DD1..DD12];
      V = [V1..V12];
      FF = [V,EA,EB,EC,CA,CB,CC,O,_I,CGATEL,CAOVF,CBOVF,CCOVF];
      VA1 = [0,0,V1];
      VA2 = [0,0,V2];
      VA3 = [0,0,V3];
      VA4 = [0,0,V4];
      VB1 = [0,0,V5];
```

```
        VB2 = [0,0,V6];
        VB3 = [0,0,V7];
        VB4 = [0,0,V8];
        VC1 = [0,0,V9];
        VC2 = [0,0,V10];
        VC3 = [0,0,V11];
        VC4 = [0,0,V12];

ADD macro (Y,A,B,I,O)
        {?Y = ?A+?B+[0,?I];
         ?O = !?I&((?A==3)&(?B>=1) # (?A==2)&(?B>=2) # (?A==1)&(?B==3)) #
              ?I&((?A==3) # (?A==2)&(?B>=1) # (?A==1)&(?B>=2) # (?B==3));}

RADD macro (Y,A,B,I,O)
        {?Y := ?A+?B+[0,?I];
         ?O = !?I&((?A==3)&(?B>=1) # (?A==2)&(?B>=2) # (?A==1)&(?B==3)) #
              ?I&((?A==3) # (?A==2)&(?B>=1) # (?A==1)&(?B>=2) # (?B==3));}

RRADD macro (Y,A,B,I,O)
        {?Y := ?A+?B+[0,?I];
         ?O := !?I&((?A==3)&(?B>=1) # (?A==2)&(?B>=2) # (?A==1)&(?B==3)) #
               ?I&((?A==3) # (?A==2)&(?B>=1) # (?A==1)&(?B>=2) # (?B==3));}

COUNT macro (C,E)
        {?C.t = CGATE&CGATEL&!?COVF&((?C$(?C+1))&(?E==1) #
                (?C$(?C+2))&(?E==2) # (?C$(?C+3))&(?E==3) #
                (?C$(?C+4))&(?E==4)) # ?C&CGATE&!CGATEL;
         ?COVF := (?C>=120)&CGATE&CGATEL&!(?E==0) #
                  ?COVF&!(SCLK);} equations
"CLOCK GENERATION

FF.clk = FMHZ;
    SCLK = CGATE&!CGATEL;
    _I := I;
    O := (I$_I)&!DIAG # DD&DIAG&TCLK;
    V := O&([[(SEL==0),(SEL==1),(SEL==2),(SEL==3),(SEL==4),(SEL==5),(SEL==6),
             (SEL==7),(SEL==8),(SEL==9),(SEL==10),(SEL==11)] # (SEL==15));

"ENCODES

EA0 := (VA1+VA2+VA3+VA4 == [0,0,1]) # (VA1+VA2+VA3+VA4 == [0,1,1]);
    EA1 := (VA1+VA2+VA3+VA4 == [0,1,0]) # (VA1+VA2+VA3+VA4 == [0,1,1]);
    EA2 := (VA1+VA2+VA3+VA4 == [1,0,0]);

EB0 := (VB1+VB2+VB3+VB4 == [0,0,1]) # (VB1+VB2+VB3+VB4 == [0,1,1]);
    EB1 := (VB1+VB2+VB3+VB4 == [0,1,0]) # (VB1+VB2+VB3+VB4 == [0,1,1]);
    EB2 := (VB1+VB2+VB3+VB4 == [1,0,0]);

EC0 := (VC1+VC2+VC3+VC4 == [0,0,1]) # (VC1+VC2+VC3+VC4 == [0,1,1]);
    EC1 := (VC1+VC2+VC3+VC4 == [0,1,0]) # (VC1+VC2+VC3+VC4 == [0,1,1]);
    EC2 := (VC1+VC2+VC3+VC4 == [1,0,0]);

"COUNTERS
    CGATEL := CGATE;
    COUNT (CA,EA);
    COUNT (CB,EB);
    COUNT (CC,EC);
```

90

```
"adder
    ADD ([FS1,FS0],[CA1,CA0],[CB1,CB0],0,FSCY1);
    ADD ([FS3,FS2],[CA3,CA2],[CB3,CB2],FSCY1,FSCY2);
    ADD ([FS5,FS4],[CA5,CA4],[CB5,CB4],FSCY2,FSCY3);
    ADD ([FS7,FS6],[0,CA6],[0,CB6],FSCY3,FSCY4);

RADD ([S1,S0],[CC1,CC0],[FS1,FS0],0,SCY1);
    RADD ([S3,S2],[CC3,CC2],[FS3,FS2],SCY1,SCY2);
    RADD ([S5,S4],[CC5,CC4],[FS5,FS4],SCY2,SCY3);
    RRADD ([S7,S6],[0,CC6],[FS7,FS6],SCY3,S8);
    S.oe = !OE_;
    S.clk = SCLK;

END
```

221/228
PATENT

EXHIBIT 5

```
module rtegae title 'GAIN AND ALIGNMENT ENGINE
       Ver. 0; 8/11/94'
       R1U58R0 device 'MACH435A';

"inputs
    MAD,MAS,VSYNC_,HSYNC_,CGATE,CSYNC pin 3,4,6,7,41,8;
    SUM0..SUM2 pin 10,12,13;
    EACC,HRD,HSTB,ALNSEL,GACYC,DIAG,FSDIAG,VDIAG pin 15,17,18,24,25,27,28,29;
    FMHZ pin 65;
    EXTCLK pin 83;

"outputs
    BSY,WE_,OE_,CS1_,CS2_,!ALUENA,!ALUENB,ALUOE_,!ALUSB pin 31,34,35,36,37,70,69,71,73 istype 'reg_D,buffer';
    GOE0_,GOE1_,GOE2_,GOE3_,GOE4_,GOE5_,GOE6_,GOE7_ pin 75,76,77,78,79,80,81,82 istype 'reg_D,buffer';
    TCLK,LDGA pin 40,19 istype 'reg_D,buffer';
    TFMHZ pin 68 istype 'reg_D,buffer';
    SEL0..SEL3 pin 72,5,30,26;
    AC0..AC17 pin 45,46,47,48,49,50,51,52,54,55,56,57,58,59,60,61,66,67 istype 'reg_T,buffer';

"nodes
    DC0..DC4,T0,T1,TGC0..TGC4 node istype 'reg_T,buffer';
    HIGH,CNTACA,CNTACB,CNTACCD,RSTACAB,RSTACCD node istype 'reg_D,buffer';
    HCYCLE,LDSC,CNTSC,CNTDC,RSTDC,_FRAME node istype 'reg_D,buffer';
    FRAME pin 9 istype 'reg_D,buffer';
    SC0..SC1 pin 16,14 istype 'reg_T,buffer';
    SC2..SC6 node istype 'reg_T,buffer';
    _GACYC,_CGATE,_VSYNC_,_HSYNC_,_HSTB,_CSYNC node istype 'reg_D,buffer';
    CFB,CYC node;
    _CGLE2.._CGLE0 node istype 'reg_D,buffer';
    HOLDOFF node istype 'reg_D,buffer';

"constants
    H,L,X,C,Z = 1,0,.X.,.C.,.Z.;
    ACA = [AC2..AC0];
    ACB = [AC6..AC3];
    ACC = [AC12..AC7];
    ACD = [AC17..AC13];
    AC = [ACD,ACC,ACB,ACA];
    ACCS = [AC11..AC7,MAD];
    ACDS = [AC16..AC12];
    T = [T1,T0];
    SUM = [SUM2..SUM0];
    DC = [DC4..DC0];
    TGC = [TGC4..TGC0];
    GOE_ = [GOE0_,GOE1_,GOE2_,GOE3_,GOE4_,GOE5_,GOE6_,GOE7_];
    SEL = [SEL3..SEL0];
    SC = [SC6..SC0];
    _CGLE = [_CGLE2.._CGLE0];
    FF = [BSY,WE_,OE_,CS1_,CS2_,ALUENA,ALUENB,ALUOE_,ALUSB,GOE_,TCLK,LDGA,
          AC,DC,SC,T,TGC,HIGH,HCYCLE,CNTACA,CNTACB,CNTACCD,RSTACAB,
          RSTACCD,LDSC,CNTSC,CNTDC,RSTDC,_GACYC,_CGATE,_VSYNC_,_HSYNC_,
          _HSTB,_CSYNC,TFMHZ,FRAME,_FRAME,_CGLE,HOLDOFF];
    CGTE = !CGATE&_CGATE;
    CGLE = CGATE&!_CGATE;
    SBSY = GACYC&!_GACYC;
    FTE = !FRAME&_FRAME;
    FLE = FRAME&!_FRAME;
    HSTE = HSYNC_&!_HSYNC_;
```

93

```
VSTE = VSYNC_&!_VSYNC_;
HSLE = !HSYNC_&_HSYNC_;
VSLE = !VSYNC_&_VSYNC_;
HSTBTE = HACC&!HSTB&_HSTB;
CSTE = !CSYNC&_CSYNC;
V0   = [0,0,0,0,0,0,0];
V1   = [0,0,0,0,0,0,1];
V3   = [0,0,0,0,0,1,1];
V7   = [0,0,0,0,1,1,1];
V15  = [0,0,0,1,1,1,1];
V31  = [0,0,1,1,1,1,1];
V63  = [0,1,1,1,1,1,1];
V127 = [1,1,1,1,1,1,1];

"OVERALL ALIGNMENT CYCLE
"CGATE    __--__--__--__--_____--__--__--_____--__--__
"VSYNC  --_____------------_____----------_____----
"FRAME  _____------------_____------------_____----
"SCH      111111111111111110000000000000000000000000
"BSY    _------------------------------------_____

"OVERALL CALIBRATION CYCLE
"CGATE   __--__--__--__--_____--__--__--_____--__--__--__--__
"BSY    _------------------------------------_____
"CSYNC   __--_____--_____--_____
"FRAME  _____--------_____--------_____--------__
"SCH      1111110000000000000000111111000000000  000001111110000000000
"SEL      00000000000011111111111111111111122222  1111111111111111111
"                                                 111111111111112222

"FRAME TIMING
"FMBE  |||||||||||||||||||||||||||||||||||||||||||||||||||||
"TFMBE __-_-_-_-_-_-_-_-_-_-_-_-_-_-_-_-_-_-_-_-_-_-_-_-_-_-
"TWMBE _-__--__--__--__--__--__--__--__--__--__--__--__--__-
"CGATE -----_____------------------------------------___
"_CGATE-----_____------------------------------------___
"FRAME  _____--------------------------------------------___
"MCYCLE       _____
"T           0011220011220011220011220011220011220011220011220011220011220
"OE         ____--____--____--____--____--____--____--____--____
"WE           _-___-___-___-___-___-___-___-___-___-___-___-
"GOE0        ___---_____
"GOE1                ___---_____
"ENA/B         _-___-___-___-___-___-___-___-___-___-___-
"ALUOE       __--__--__--__--__--__--__--__--__--__--__--
"ADDRESS------_____0__---1--__2__---3--__4__---5--__6__---7--___
"ACNT                     _-___-___-___-___-___-___-___-___-___-

"HOST READ/WRITE
"HAS   _-----------_
"HAD   _19876543210---
"          0
"HACC    _____--------------------_____----------
"HMRD    _____------------------------_____----
"HMSTB   _____-----___---___-----_____---------_____---
"LDGA    _____--------_____
"HIGH    _____-------------_____
"CS1     _____------_____----------_____--------
"CS2     _____-----_____------_____
```

```
"OE     _____    _____    ----------_____
"WE     _____ ------    ------ _____
"ACNT   _____ -_____-__
``` equations

"CLOCK GENERATION

FF.clk = FMHZ;
    TFMHZ := !TFMHZ&!CGLE;

"TIMING CONTROL

_GACYC_ := GACYC;
    _CGATE_ := CGATE;
    _VSYNC_ := VSYNC_;
    _HSYNC_ := HSYNC_;
    _ESTB_  := ESTB;
    _FRAME_ := FRAME;
    _CSYNC_ := CSYNC;
" HOLDOFF holds off start of first FRAME until the start of a VSYNC_
    HOLDOFF := SBSY # HOLDOFF&!VSYNC_;
    BSY := GACYC&(SBSY # BSY&!(ALNSEL&FTE&(SC==0) # !ALNSEL&FTE&(ACB==11)));
    FRAME := BSY&(CGTE&ALNSEL&!VSYNC_&!HOLDOFF # !ALNSEL&CSTE #
                 FRAME&!(CGTE&(ALNSEL&VSYNC_ # !ALNSEL&CGTE&(SC==0))));

"MEMORY CONTROL

HCYCLE := FRAME&(CGLE # HCYCLE& !((ACA==7)&!WE_) );
    T.t = (T$(T+1))&HCYCLE&TFMHZ # T&!HCYCLE;
    !OE_  := HCYCLE&(T==0) # HACC&HSTB&HRD;
    !WE_  := HCYCLE&(T==2)&!TFMHZ # HACC&HSTB&!HRD;
    !GOE0_ := FRAME&(CGLE # !GOE0_&!(ALUENA));
    !GOE1_ := HCYCLE&(!WE_&(ACA==0) # !GOE1_&!(ALUENA));
    !GOE2_ := HCYCLE&(!WE_&(ACA==1) # !GOE2_&!(ALUENA));
    !GOE3_ := HCYCLE&(!WE_&(ACA==2) # !GOE3_&!(ALUENA));
    !GOE4_ := HCYCLE&(!WE_&(ACA==3) # !GOE4_&!(ALUENA));
    !GOE5_ := HCYCLE&(!WE_&(ACA==4) # !GOE5_&!(ALUENA));
    !GOE6_ := HCYCLE&(!WE_&(ACA==5) # !GOE6_&!(ALUENA));
    !GOE7_ := HCYCLE&(!WE_&(ACA==6) # !GOE7_&!(ALUENA));
    ALUENA := HCYCLE&!OE_&!ALUENA;
    ALUENB := HCYCLE&!OE_&!ALUENA;
    !ALUOE_ := HCYCLE&((T==1)&TFMHZ # (T==2)&!TFMHZ);
    ALUSB := ALNSEL&(SBSY # ALUSB&!(FTE)) # !ALNSEL&(FLE # ALUSB&!(CGTE));
    !CS1_ := HCYCLE # HACC&HSTB&(HRD # !HRD&!HIGH);
    !CS2_ := HCYCLE # HACC&HSTB&(HRD # !HRD&HIGH);

LDCA := HACC & HRD & HSTB & !CS1_;

"ADDRESS COUNTER
" *** Gain Cycle
" *** Alignment Cycle
" least significant 3 bits count up during !CGATE so eight addresses are
" written each hole. Most significant bits count CGATEs. LSBs reset
" every CGATE. MSBs reset every frame.
" *** Host IO
" least significant 7 bits count up every read or write operation
" most significant 11 bits are loaded when strobed in by HAS ACA.t = (ACA$(ACA+1))&CNTACA&!RSTACAB # ACA&RSTACAB;

95

```
        CNTACA := NCYCLE&!WE_ # !HRD&HS_&&HIGH # HRD&HSTBTE;
        ACB.t = (ACB$(ACB+1))&CNTACB&!RSTACAB # ACB&RSTACAB;
        CNTACB := !ALNSEL&FTE # ALNSEL&FRAME&CGTE # HSTBTE&(ACA==7)&(!HRD&HIGH # HRD);
        CYB = (ACB==15);
        ACC.t = (ACC$(ACC+1))&CYB&CNTACCD&!RSTACCD # ACC&RSTACCD # (ACC$ACCS)&HAS;
        CYC = (ACC==63);
        ACD.t = (ACD$(ACD+1))&CYC&CYB&CNTACCD&!RSTACCD # ACD&RSTACCD # (ACD$ACDS)&HAS;
        CNTACCD := ALNSEL&FRAME&CGTE;
        RSTACAB := !ALNSEL&SBSY # ALNSEL&FLE # HAS;
        RSTACCD := !ALNSEL&SBSY # ALNSEL&FLE;
        HIGH := HSTBTE&!HRD&!HIGH # HIGH&!(!HRD&HSTBTE # HAS);

" SENSOR SELECTS

SEL = ACB&!ALNSEL # [1,1,1,1]&ALNSEL;

"SUM COUNTER

SC.t = (SC$(SC-1))&CNTSC # ((V0&(SUM==0)#V1&(SUM==1)#V3&(SUM==2)#
                V7&(SUM==3)#V15&(SUM==4)#V31&(SUM==5)#V63&(SUM==6)#
                V127&(SUM==7))$SC)&LDSC;
        CNTSC := ALNSEL&FTE # !ALNSEL&FRAME&CGTE;
        LDSC := ALNSEL&SBSY # !ALNSEL&CSYNC;

"DIAGNOSTIC CONTROLLER

"OVERALL TIMING
"VSYNC_  --_____  ----_____  ------
"HSYNC_  --__-____-____-____  ------____-____-____-____  ----
"CGATE      _-_-_-_-__-_-_-_-__         _-_-_-_-__-_-_-_-__
"VDIAG   _____  ------------------------------
"DC      000000111111222222333333    001111001111001111001111

"            CGATE TIMING
"FMEI ||||||||||||||||||||||||||||||||||||||||||||||||||||||||||
"CGATE _____--------------------_____
"CGLE  _____-_____
"TGC   xxxxxxxxxx3210
"TGATE _____---_____

" Delay CGLE so it doesn't occur during VSLE and HSLE resets
_CGLE0 := CGLE;
_CGLE1 := _CGLE0;
_CGLE2 := _CGLE1;
DC.t = (DC$(DC+1))&CNTDC # DC&RSTDC;
CNTDC := VDIAG&CGTE # !VDIAG&HSTE;
RSTDC := VSLE # VDIAG&HSLE;
TGC.t := (TGC$(TGC-1))&TCLK # (DC$TGC)&_CGLE1;
TCLK := EXTCLK # DIAG&FSDIAG&CGATE&(_CGLE2&!(DC==0) # TCLK&!(TGC==1));

END
```

What is claimed is:

1. An x-ray detection apparatus comprising:

a plurality of detection portions, said plurality of detection portions arranged in a two-dimensional array comprising at least one row and at least one column;

each of said plurality of detection portions comprised of an x-ray detecting material, said x-ray detecting material comprising a material that converts x-rays into signals indicative of the x-ray flux detected, said detection portions outputting signals corresponding to an amount of x-ray flux detected by said x-ray detecting material; and alignment circuitry, said alignment circuitry capable of providing signals indicative of the alignment of the detection apparatus with respect to a source of detected x-rays.

2. The apparatus of claim 1 wherein said plurality of detection portions is arranged in a pseudo-circular array approximating the shape of a circle.

3. The apparatus of claim 1 wherein said plurality of detection portions is arranged in a rectangular array.

4. The apparatus of claim 1 wherein said x-ray detecting material is a scintillating material.

5. The apparatus of claim 1 wherein said signals output by said detection portions are electrical signals.

6. The apparatus of claim 5 wherein said x-ray detecting material comprises a material selected from the group consisting of: YSO, LSO, BGO, and plastic.

7. The apparatus of claim 1 wherein said x-ray detecting material converts x-rays into optical signals when excited by said x-rays; and each of said detection portions further comprises a photodetector element, said photodetector element comprising an optical signal to electrical signal converter, said output signals from said detection portions comprising electrical signals.

8. The apparatus of claim 7 further comprising an optical element coupled between said x-ray detecting material and said photodetector element.

9. The apparatus of claim 7 wherein said optical element comprises a fiber optic taper.

10. The apparatus of claim 1 further comprising an alignment structure comprising a detector housing to which said detection portions are secured and one or more alignment screws movably coupled to said detector housing.

11. An x-ray detection apparatus comprising:

a plurality of detection portions, said plurality of detection portions arranged in a two-dimensional array;

each of said plurality of detection portions comprised of an x-ray detecting material, said x-ray detecting material comprising a material that converts x-rays into signals indicative of the x-ray flux detected, said detection portions outputting signals corresponding to an amount of x-ray flux detected by said x-ray detecting material; and a first subset of detection portions comprising some of said plurality of detection portions, each detection portion of said first subset of detection portions providing output signals indicative of an alignment of the x-ray detection apparatus with respect to a source of detected x-rays.

12. The apparatus of claim 11 wherein said plurality of detection portions are arranged in a substantially pseudo-circular shape.

13. The apparatus of claim 11 wherein said plurality of detection portions are arranged in a substantially rectangular shape.

14. The apparatus of claim 11 wherein said x-ray detecting material comprises a scintillating material.

15. The apparatus of claim 11 wherein said signals output by said detection portions are electrical signals.

16. The apparatus of claim 15 wherein said x-ray detecting material comprises a material selected from the group consisting of: YSO, LSO, BGO, and plastic.

17. The apparatus of claim 11 wherein said x-ray detecting material converts x-rays into optical signals when excited by said x-rays; and each of said detection portions further comprising a photodetector element, said photodetector element comprising an optical signal to electrical signal converter, said output signals from said detection portion comprising electrical signals.

18. The apparatus of claim 17 further comprising an optical element coupled between said x-ray detecting material and said photodetector element.

19. The apparatus of claim 18 wherein said optical element comprises a fiber optic taper.

20. The apparatus of claim 11 further comprising an x-ray shield disposed opposing a first surface of a second subset of said plurality of detection portions.

21. The apparatus of claim 20 wherein said second subset of detection portions comprises each of said plurality of detection portions excluding said first subset of detection portions.

* * * * *

UNITED STATES PATENT AND TRADEMARK OFFICE
CERTIFICATE OF CORRECTION

PATENT NO. : 5,808,306
DATED : September 15, 1998
INVENTOR(S) : Brian Skillicorn, Giovanni Pastrone It is certified that error appears in the above-identified patent and that said Letters Patent is hereby corrected as shown below:

Column 4, line 47 – delete "an/or" and insert --and/or--.

Column 10, line 26 – delete ",".

Column 13, line 24 – delete "give" and insert --given--.

Column 14, line 66 – delete "$v_{TLi}$" and insert --$V_{TLi}$--.

Column 14, line 67 – delete "$AF_{y-axis}$" and insert --$AF_{x-axis}$--.

Column 15, line 67 – delete "13S4" and insert --1354--.

Fig 3 – replace "P" in the center square with a --5--.

Fig 7 – the horizontal "Y" is missing.

Fig 13 – reference numeral "1360" should be --360--.

Signed and Sealed this

Tenth Day of August, 1999

Attest:

Q. TODD DICKINSON

*Attesting Officer*   *Acting Commissioner of Patents and Trademarks*